United States Patent
Cui et al.

(10) Patent No.: US 9,944,944 B2
(45) Date of Patent: *Apr. 17, 2018

(54) AAD-12 EVENT 416, RELATED TRANSGENIC SOYBEAN LINES, AND EVENT-SPECIFIC IDENTIFICATION THEREOF

(75) Inventors: Yunxing C. Cui, Carmel, IN (US); Thomas Hoffman, Zionsville, IN (US); Ning Zhou, Zionsville, IN (US); Gregory J. Gilles, Alpharetta, GA (US); Terry R. Wright, Carmel, IN (US); Julissa Colon, West Lafayette, IN (US); Ricardo A. Barnes, Ponce, PR (US); Nathan J. VanOpdorp, Geneseo, IL (US); Yonghe Bai, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1240 days.

This patent is subject to a terminal disclaimer.

(21) Appl. No.: 13/511,990

(22) PCT Filed: Nov. 24, 2010

(86) PCT No.: PCT/US2010/058001
§ 371 (c)(1),
(2), (4) Date: Aug. 21, 2013

(87) PCT Pub. No.: WO2011/066384
PCT Pub. Date: Jun. 3, 2011

(65) Prior Publication Data
US 2013/0324408 A1 Dec. 5, 2013

Related U.S. Application Data

(60) Provisional application No. 61/263,950, filed on Nov. 24, 2009.

(51) Int. Cl.
| | | |
|---|---|---|
| *C12N 15/82* | (2006.01) |
| *A01H 1/02* | (2006.01) |
| *A01H 5/10* | (2006.01) |
| *A01H 1/04* | (2006.01) |
| *C12N 9/02* | (2006.01) |
| *C12Q 1/68* | (2018.01) |

(52) U.S. Cl.
CPC ........... *C12N 15/8274* (2013.01); *A01H 1/02* (2013.01); *A01H 1/04* (2013.01); *A01H 5/10* (2013.01); *C12N 9/0069* (2013.01); *C12N 9/0071* (2013.01); *C12Q 1/6895* (2013.01); *C12Q 2600/156* (2013.01)

(58) Field of Classification Search
CPC . C12N 15/82; A01H 5/10; A01H 1/02; A01H 1/04
See application file for complete search history.

(56) References Cited

U.S. PATENT DOCUMENTS

| 6,235,974 | B1 | 5/2001 | Qiu et al. |
| 7,838,733 | B2 | 11/2010 | Wright et al. |
| 8,685,677 | B2 | 4/2014 | Novak et al. |
| 2003/0135879 | A1 | 7/2003 | Weeks et al. |
| 2004/0016025 | A1 | 1/2004 | Budworth et al. |
| 2006/0101535 | A1 | 5/2006 | Forster et al. |
| 2006/0127889 | A1 | 6/2006 | Dotson et al. |
| 2008/0051288 | A1* | 2/2008 | Cressman, Jr. .......... A01H 5/10 504/198 |
| 2008/0119361 | A1 | 5/2008 | Feng et al. |
| 2009/0093366 | A1 | 4/2009 | Wright et al. |
| 2010/0251432 | A1 | 9/2010 | Lira et al. |

FOREIGN PATENT DOCUMENTS

| WO | WO 2006/081669 | | 8/2006 | |
| WO | WO 2007/053482 | * | 5/2007 | ............... A01H 5/00 |
| WO | WO 2008/077892 | * | 7/2008 | ............. C12N 15/82 |
| WO | WO 2011/066360 | | 6/2011 | |
| WO | WO 2011/066382 | | 6/2011 | |

OTHER PUBLICATIONS

GenomeWalker kit user mannual, retrieved from www.clontech.com, published on Apr. 25, 2007.*
Heck, G. R., et al. "Development and characterization of a CP4 EPSPS-based, glyphosate-tolerant corn event." Crop Science 45.1 (2005): 329-339.*
Zeng, P., et al. "Refined glufosinate selection in Agrobacterium-mediated transformation of soybean [*Glycine max* (L.) Merrill]." Plant cell reports 22.7 (2004): 478-482.*
Samac, Deborah A., et al. "A comparison of constitutive promoters for expression of transgenes in alfalfa (*Medicago sativa*)." Transgenic research13.4 (2004): 349-361.*

(Continued)

*Primary Examiner* — Lee A Visone
*Assistant Examiner* — Weihua Fan
(74) *Attorney, Agent, or Firm* — C. Philip Poirier; Barnes & Thornburg LLP

(57) ABSTRACT

This invention includes a novel aad-12 transformation event for herbicide tolerance in soybean plants—referred to herein as pDAB4468-0416. This invention includes a heterologous polynucleotide inserted into a specific site within the genome of a soybean cell. In some embodiments, said event/polynucleotide can be "stacked" with other traits, including, for example, other herbicide tolerance gene(s) and/or insect-inhibitory proteins. Additionally, the subject invention provides assays for detecting the presence of the subject event in a sample (a soybean, for example). The assays can be based on the DNA sequence of the recombinant construct, inserted into the soybean genome, and on the genomic sequences flanking the insertion site. Kits and conditions useful in conducting the assays are also provided.

24 Claims, 6 Drawing Sheets

(56) References Cited

OTHER PUBLICATIONS

GenomeWalker kit user manual, Apr. 2007, retrieved from clontech.com.*
Corporation obtaining approval, the name of its representative, and the address of its main office, obtained online at: http://www.bch.biodic.go.jp/download/en_lmo/DAS68416enUR.pdf (2009).
Choi et al., "Glycine max young leaves DNA Glycine max STS genomic, sequence tagged Site," GenBank GF092905 44607 (Dec. 2, 2008).
Cregan, "Glycine max young leaves DNA Glycine max STS genomic", Database Genbank GF093418 19093 (Dec. 2, 2008).
JPN6015004045; sae51e08.y2 Gm-c1051 Glycine max cDNA clone Genome Systems Clone ID: Gm-c1051-8679 5- similar to TR: , 2004.
JPN6015004047; GM_WBb0129F01.r GM_WBb Glycine max genomic clone GM_WBb0129F01 3-, genomic survey sequence , 2006.
Krieger, "Petition for determination of nonregulated status for herbicide tolerant DAS-68416-4 Soybean; OECD Unique Identifier: DAS-68416-4," USDA Petition for Nonregulated Status of DAS-68416-4 Soybean ( Dec. 8, 2009).
Schmidt et al., "Quantitative detection of transgenes in soybean [*Glycine max* (L.) Merrill] and peanut (*Arachis hypogaea* L.) by real-time polymerase chain reaction," *Plant Cell Rep.*, 20(5):422-428 (2001).
Shoemaker et al., "Glycine max genomic clone GM_WBb0129F01 3',genomic survey sequence", Database Genbank ED759286 (Nov. 1, 2006).
GeneBank AccessionK00545.
GeneBank AccessionK00547.
GeneBank AccessionK00549.
GeneBank Accession Y18556.
GeneBank AccessionM35007.
GeneBank Accession AF184978.
GeneBank AccessionAJ277272.
GeneBank AccessionAJ414108.
GeneBank AccessionAY147202.
GeneBank AccessionAJ506207.
GeneBank Accession AJ506239.
GeneBank Accession EU099579.
GeneBank Accession CG515574.
GeneBank Accession CG515575.
GeneBank Accession DM163293.
GeneBank Accession DM159825.
GeneBank Accession DM159826.
GeneBank Accession K00821 M30884.
GeneBank Accession DM199655.
GeneBank Accession AC235254.
GeneBank Accession AY456904.
GeneBank Accession DQ156557.
GeneBank AccessionAY123624.
GeneBank Accession HB838877.
GeneBank Accession FB873185.
GeneBank Accession AF145349.
GeneBank Accession AR014675.
GeneBank Accession AR157937.
GeneBank Accession AX417132.
GeneBank Accession U67919.
GeneBank Accession GQ497217.1 (Sep. 28, 2009).
Shoemaker et al., "Glycine max genomic clone GM_WBb0085K19 5',genomic survey sequence", Database Genbank ED729286 (Nov. 1, 2006).

* cited by examiner

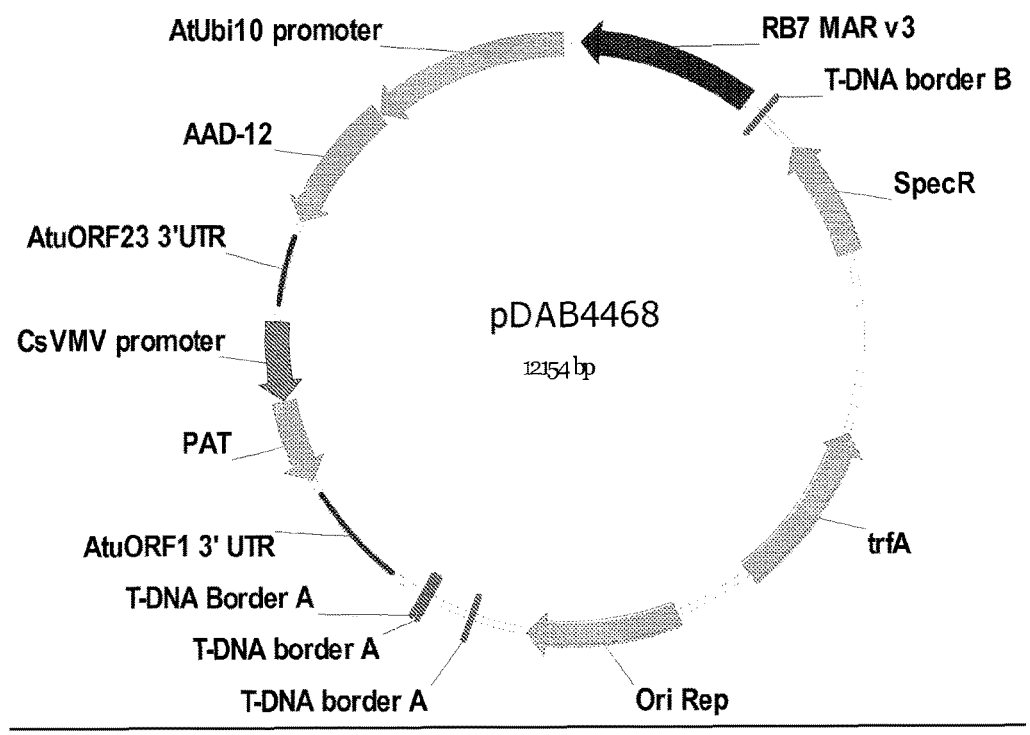
Figure 1. Plasmid Map of pDAB4468 containing the *aad*-12 and *pat* Expression Cassettes.

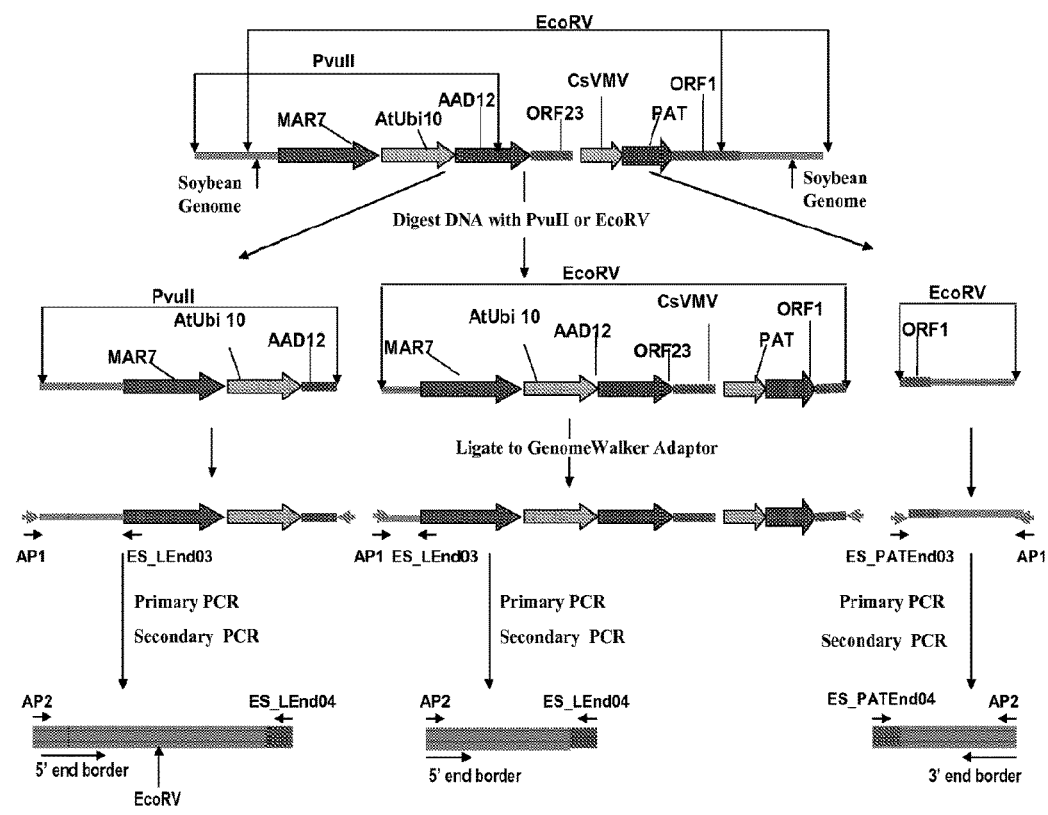
Figure 2. Genomic DNA of the soybean event DAS-68416-4 was digested with *Eco*RV, or *Pvu* II and used to generate corresponding GENOMEWALKER™ libraries, which were used as templates to amplify the target DNA sequences.

Figure 3. The schematic diagram depicts the primer locations and cloning strategy for full length sequencing of the soybean Event DAS-68416-4 from 5' to 3' borders.
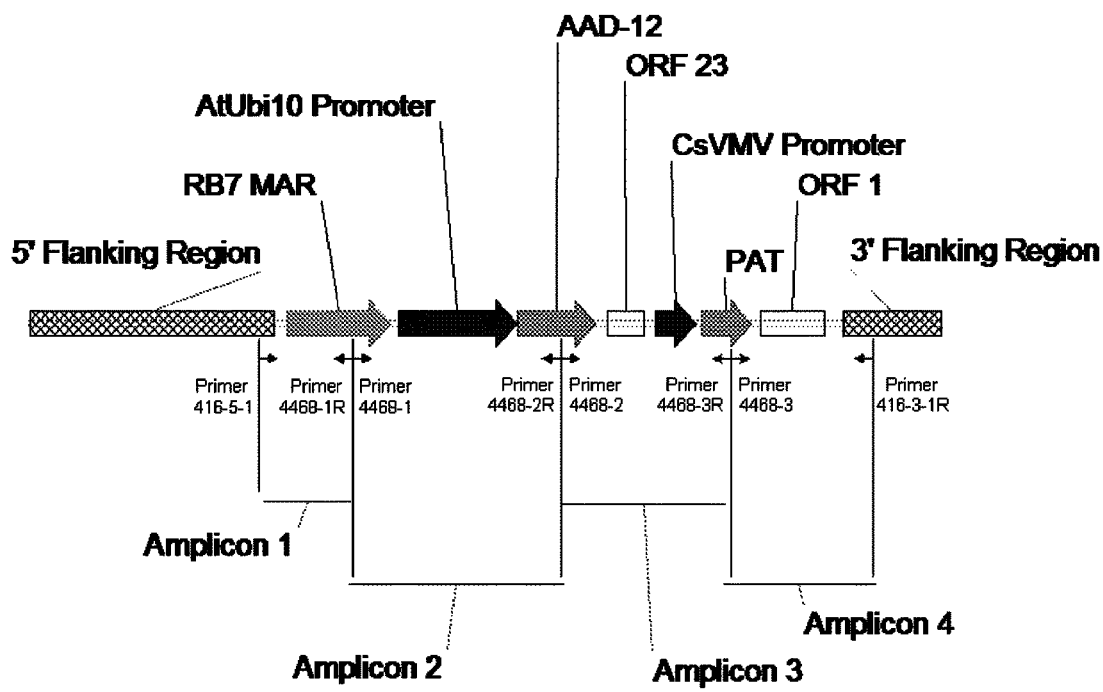

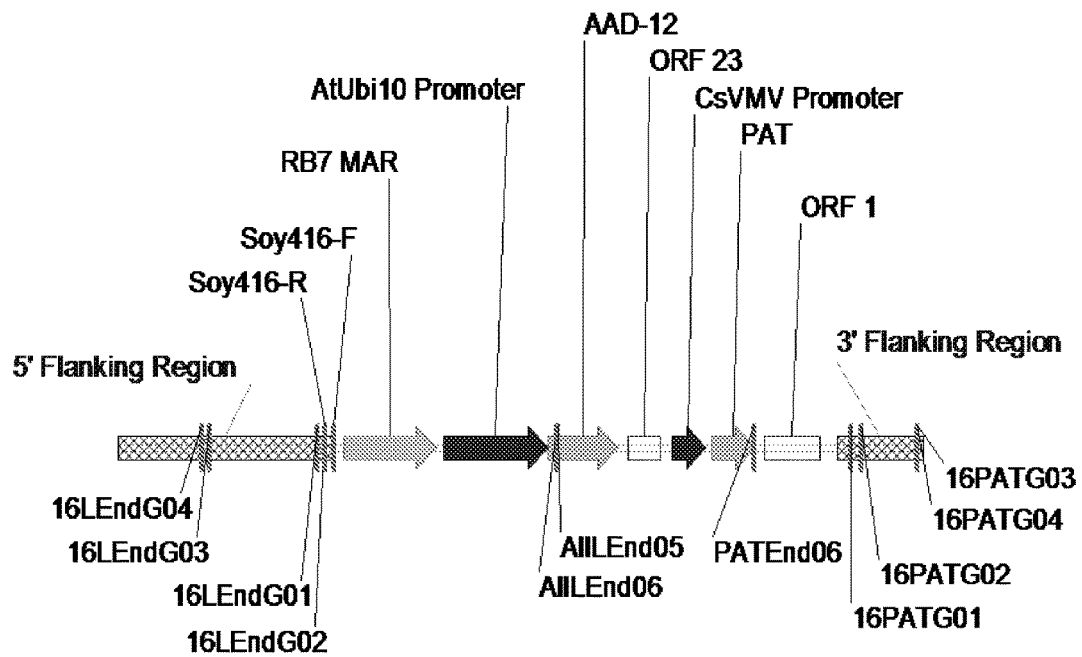
Figure 4. The schematic diagram depicts the primer locations for confirming the full length sequence of the soybean Event DAS-68416-4 from 5' to 3' borders.

Figure 5. The schematic diagram depicts the primer locations for confirming the insertion site sequence of the AAD-12 soybean event DAS-68416-4.
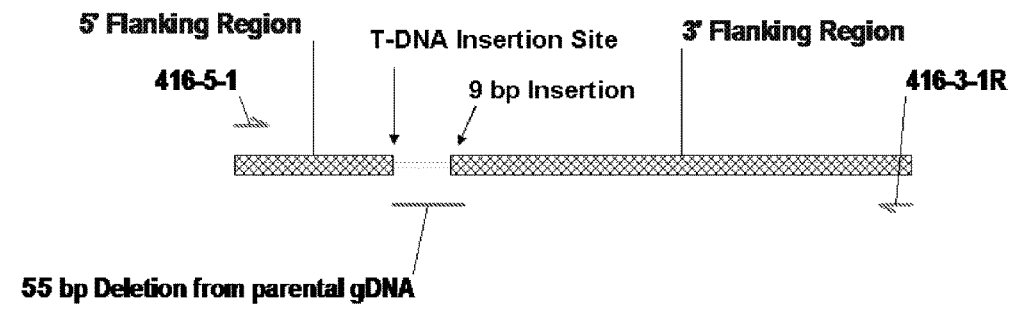

Figure 6: Expression levels through the plant lifecycle.
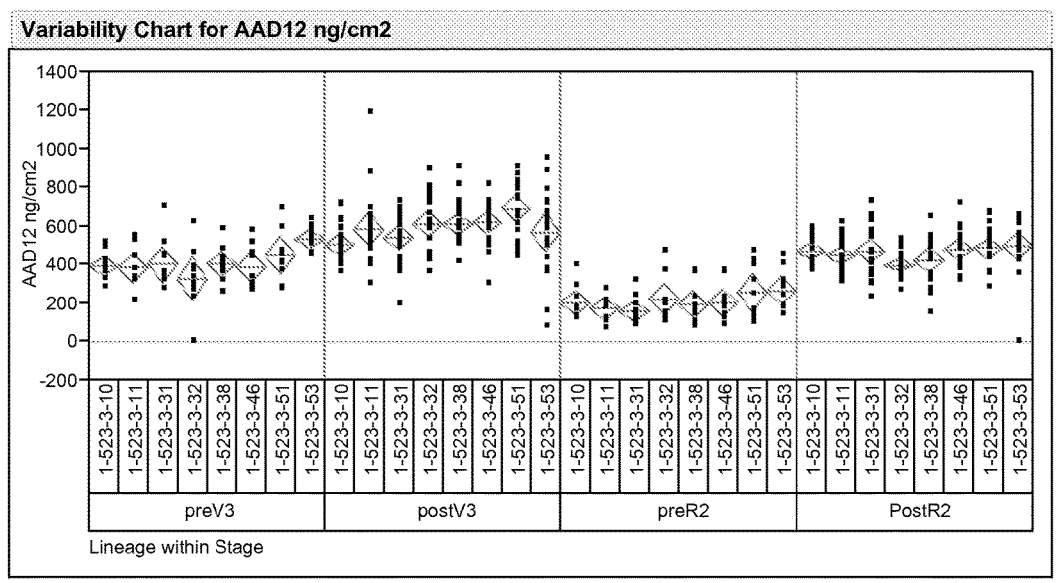

SEQUENCE LISTING

```
<160> NUMBER OF SEQ ID NOS: 30

<210> SEQ ID NO 1
<211> LENGTH: 10212
<212> TYPE: DNA
<213> ORGANISM: Artificial Sequence
<220> FEATURE:
<223> OTHER INFORMATION: Insert and flanking sequences for soybean
      Event DAS-68416-4

<400> SEQUENCE: 1
ctgtcgttgg attcacagaa cattgacgcc agttttcact tcgttatctt tgaattcatt      60
aaaatcgaat ctctcaccta tacccccca tttttctaat ccatcataat caaaattcat     120
aaatgaatca gttaccatta ccataatacc tttttgaaaa tgagtttgaa taatcagtat     180
ctttagaaaa ctaattaaga aattaaataa aaaatattta tcatgaagat gagtgtaaga     240
aaaattatga aaagtataac tttatacatt tctataaaat tatttttct tttaatttct      300 taattaatat cctaagtaaa tgagttaata tttatctttc aaaaattctt atagtcgcca     360
attaattttc ccatgcaatg acaacttgtc cgtattctac gtggtaggtt aggctacctg     420
ccgagacaaa ttgccttgag acaaattcaa tagagaaccc ttccaaggga ccattataaa     480
tagagaactt tcattaaccg ataagccaca ccctttcaat caaacacaaa cacttgaagt     540
actaagttag tgtgtttgag caaattaact atggcttcgt tttgttctag attgacaatt     600
tgtttggctc tgtttgtcct catatggggg agtgccaatg cacaactttc tacaaacttt     660
tactaccatt catgtccaaa cctcttctcc tctgtgaaat ccacagtgca atctgccata     720
tctaaggaga cccgcatggg tgcttctctc cttcgcttgt tcttccacga ttgctttgtc     780
aatgtaattt atttgcacct tctcccactt acatacaaat atgctaagct tacatatagc     840
tcctctttct accacttgca tgcatcatct aatttgttt gaaacaacac ttgttccttt     900
tattatacac atcatctttg ataaatttt gtcgtgtgca actttttttt agtgtgttaa     960
tcagttctat gatgatacta ttagttaaga aatttaatg cacttaataa accattttaa    1020
gtactttaac cgttcaatga tattatatat ttaaagataa taaatatttc tgcttttgtt    1080
tctatattag tgtagttaag aaccttctta cttcttagct agctaaatat taatgagtaa    1140
acattaacaa atgcagggat gtgatggttc aattctattg gatgacacat caagcttcac    1200
cggagagaag aacgcaaacc ccaacaggaa ctctgctcgt ggattcgagg ttattgacaa    1260
cattaaatca gccgtggaga aagtgtgtcc aggagttgtt tcctgcgcag atatccttgc    1320
catcgctgcc agagactctg ttcagattgt aagtggtcaa acaaccaaca aaaacacatt    1380
aaactaaatc attaaattgt acatatcaaa attaattacc aatttagtac cacacatgca    1440
attaaagaga acattttgtt gattttgatc aatatagctt ggaggcccta catggaatgt    1500
taaacttgga agaagagacg ctagaactgc tagccaatct gctgctaaca atggcatccc    1560
```

```
tgcacccact tcaaaccttta accaactcat ctcaagattt agcgctcttg gactttccac   1620
caaggacttg gtcgccttgt ccggtacaaa acatatatca cataattttc caattaatta   1680
catttcaatc atatagtaaa atttctcaat taattaggaa catgagaaac ttatagtcac   1740
acgttctttt gttgaggaat attgcatggt ttaattttgc tttcattagg tggtcacaca   1800
attggacaag caaggtgcac aaacttcaga gcccgcatct acaacgagac caacatagaa   1860
accgcatttg caaggactag gcagcaaagc tgccctagaa catcagggtc aggggacaac   1920
aatctggcac cacttgatct tcaaactcca accagctttg acaactacta cttcaagaac   1980
ctcgttcaga agaagggtct cctccactct gatcagcaac tgttcaacgg tgggtccacc   2040
gactccattg tgcgtggcta cagcaccaac ccgggcacct tctcctctga tttcgccgcc   2100
gccatgatca agatgggaga cattagtcct ctcactggct ccaatggaga aatcaggaag   2160
aattgtagaa ggattaacta atttgattca gtcttgaata ttaagggtcc tacacatacg   2220
caagcaattt aattgtgttt aataagttgt taaaacatgt tttggttgta ttttggattc   2280
ctagtgtagt ttcggtgatc aatgccgtct actttagtgt gttctacttc cctttatttt   2340
tgtttctttt ttacttttttc cttaactata ttgtaggaaa aaaaaaatcc tttatcaagc   2400
atttatcaag aacggagttt gctttttaat tttcccttca taacattcca tcagaattca   2460 gttttgctttt tgcttctaaa ttacgttcaa atcagggatg ataatcggtt aggtaatata   2520
tacagtaccc cttgcatagt cacgtttgaa aaatataatc atacttagtt cggtaacaat   2580
ttaaattatc attctcgtaa tcattagcta cttatgcact catatccgta tccgctactt   2640
gctcttgtcg taagtcaata aattaatata aaaaaatact taaaacttgt tacaactaaa   2700
ttaaaaattt atttttaaat cattcaagca ccagtcagca tcatcacacc aaaagttagg   2760
cccgaatagt ttgaaattag aaagctcgca attgaggtct acaggccaaa ttcgctctta   2820
gccgtacaat attactcacc ggatcctaac cggtgtgatc atgggccgcg attaaaaatc   2880
tcaattatat ttggtctaat ttagtttggt attgagtaaa acaaattcga accaaaccaa   2940
aatataaata tatagttttt atatatatgc ctttaagact ttttatagaa ttttctttaa   3000
aaaatatcta gaaatatttg cgactcttct ggcatgtaat atttcgttaa atatgaagtg   3060
ctccattttt attaacttta ataattggt tgtacgatca ctttcttatc aagtgttact   3120
aaaatgcgtc aatctctttg ttcttccata ttcatatgtc aaaacctatc aaaattctta   3180
tatatctttt tcgaatttga agtgaaattt cgataattta aaattaaata gaacatatca   3240
ttatttaggt atcatattga tttttatact taattactaa atttggttaa ctttgaaagt   3300
gtacatcaac gaaaaattag tcaaacgact aaaataaata aatatcatgt gttattaaga   3360
aaattctcct ataagaatat tttaatagat catatgtttg taaaaaaaat taattttac   3420 taacacatat atttacttat caaaaatttg acaaagtaag attaaaataa tattcatcta   3480
acaaaaaaaa aaccagaaaa tgctgaaaac ccggcaaaac cgaaccaatc caaaccgata   3540
tagttggttt ggtttgattt tgatataaac cgaaccaact cggtccattt gcaccctaa   3600 tcataatagc tttaatattt caagatatta ttaagttaac gttgtcaata tcctggaaat   3660
tttgcaaaat gaatcaagcc tatatggctg taatatgaat ttaaaagcag ctcgatgtgg   3720
tggtaatatg taatttactt gattctaaaa aaatatccca agtattaata atttctgcta   3780
ggaagaaggt tagctacgat ttacagcaaa gccagaatac aatgaaccat aaagtgattg   3840
aagctcgaaa tatacgaagg aacaaatatt tttaaaaaaa tacgcaatga cttggaacaa   3900
aagaaagtga tatatttttt gttcttaaac aagcatcccc tctaaagaat ggcagttttc   3960
```

| | |
|---|---|
| ctttgcatgt aactattatg ctcccttcgt tacaaaaatt ttggactact attgggaact | 4020 |
| tcttctgaaa atagtggcca ccgcttaatt aaggcgcgcc atgcccgggc aagcggccgc | 4080 |
| acaagtttgt acaaaaaagc aggctccgcg gtgactgact gaaaagcttg tcgacctgca | 4140 |
| ggtcaacgga tcaggatatt cttgtttaag atgttgaact ctatggaggt ttgtatgaac | 4200 |
| tgatgatcta ggaccggata agttcccttc ttcatagcga acttattcaa agaatgtttt | 4260 |
| gtgtatcatt cttgttacat tgttattaat gaaaaaatat tattggtcat tggactgaac | 4320 |
| acgagtgtta aatatggacc aggcccccaaa taagatccat tgatatatga attaaataac | 4380 |
| aagaataaat cgagtcacca aaccacttgc cttttttaac gagacttgtt caccaacttg | 4440 |
| atacaaaagt cattatccta tgcaaatcaa taatcataca aaaatatcca ataacactaa | 4500 |
| aaaattaaaa gaaatggata atttcacaat atgttatacg ataaagaagt tacttttcca | 4560 |
| agaaattcac tgattttata agcccacttg cattagataa atggcaaaaa aaaacaaaaa | 4620 |
| ggaaaagaaa taaagcacga agaattctag aaaatacgaa atacgcttca atgcagtggg | 4680 |
| acccacggtt caattattgc caattttcag ctccaccgta tatttaaaaa ataaaacgat | 4740 |
| aatgctaaaa aaatataaat cgtaacgatc gttaaatctc aacggctgga tcttatgacg | 4800 |
| accgttagaa attgtggttg tcgacgagtc agtaataaac ggcgtcaaag tggttgcagc | 4860 |
| cggcacacac gagtcgtgtt tatcaactca aagcacaaat acttttcctc aacctaaaaa | 4920 |
| taaggcaatt agccaaaaac aactttgcgt gtaaacaacg ctcaatacac gtgtcatttt | 4980 |
| attattagct attgcttcac cgccttagct ttctcgtgac ctagtcgtcc tcgtcttttc | 5040 |
| ttcttcttct tctataaaac aatacccaaa gcttcttctt cacaattcag atttcaattt | 5100 |
| ctcaaaatct taaaaacttt ctctcaattc tctctaccgt gatcaaggta aatttctgtg | 5160 |
| ttccttattc tctcaaaatc ttcgattttg ttttcgttcg atcccaattt cgtatatgtt | 5220 |
| ctttggttta gattctgtta atcttagatc gaagacgatt ttctgggttt gatcgttaga | 5280 |
| tatcatctta attctcgatt agggtttcat aaatatcatc cgatttgttc aaataatttg | 5340 |
| agttttgtcg aataattact cttcgatttg tgatttctat ctagatctgg tgttagtttc | 5400 |
| tagtttgtgc gatcgaattt gtcgattaat ctgagttttt ctgattaaca gagatctcca | 5460 |
| tggctcagac cactctccaa atcacaccca ctggtgccac cttgggtgcc acagtcactg | 5520 |
| gtgttcacct tgccacactt gacgatgctg gtttcgctgc cctccatgca gcctggcttc | 5580 |
| aacatgcact cttgatcttc cctgggcaac acctcagcaa tgaccaacag attacctttg | 5640 |
| ctaaacgctt tggagcaatt gagaggattg gcggaggtga cattgttgcc atatccaatg | 5700 |
| tcaaggcaga tggcacagtg cgccagcact ctcctgctga gtgggatgac atgatgaagg | 5760 |
| tcattgtggg caacatggcc tggcacgccg actcaaccta catgccagtc atggctcaag | 5820 |
| gagctgtgtt cagcgcagaa gttgtcccag cagttggggg cagaacctgc tttgctgaca | 5880 |
| tgagggcagc ctacgatgcc cttgatgagg caacccgtgc tcttgttcac caaaggtctg | 5940 |
| ctcgtcactc ccttgtgtat tctcagagca agttgggaca tgtccaacag gccgggtcag | 6000 |
| cctacatagg ttatggcatg gacaccactg caactcctct cagaccattg gtcaaggtgc | 6060 |
| atcctgagac tggaaggccc agcctcttga tcggccgcca tgcccatgcc atccctggca | 6120 |
| tggatgcagc tgaatcagag cgcttccttg aaggacttgt tgactgggcc tgccaggctc | 6180 |
| ccagagtcca tgctcaccaa tgggctgctg gagatgtggt tgtgtgggac aaccgctgtt | 6240 |
| tgctccaccg tgctgagccc tgggatttca agttgccacg tgtgatgtgg cactccagac | 6300 |
| tcgctggacg cccagaaact gagggtgctg ccttggtttg agtagttagc ttaatcacct | 6360 |

```
agagctcggt caccagcata atttttatta atgtactaaa ttactgtttt gttaaatgca    6420
attttgcttt ctcgggattt taatatcaaa atctatttag aaatacacaa tattttgttg    6480
caggcttgct ggagaatcga tctgctatca taaaaattac aaaaaaattt tatttgcctc    6540
aattatttta ggattggtat taaggacgct taaattattt gtcgggtcac tacgcatcat    6600
tgtgattgag aagatcagcg atacgaaata ttcgtagtac tatcgataat ttatttgaaa    6660
attcataaga aaagcaaacg ttacatgaat tgatgaaaca atacaaagac agataaagcc    6720
acgcacattt aggatattgg ccgagattac tgaatattga gtaagatcac ggaatttctg    6780
acaggagcat gtcttcaatt cagcccaaat ggcagttgaa atactcaaac cgccccatat    6840
gcaggagcgg atcattcatt gtttgtttgg ttgcctttgc caacatggga gtccaaggtt    6900
gcggccgcgc gccgacccag ctttcttgta caaagtggtt gcggccgctt aattaaattt    6960
aaatgcccgg gcgtttaaac gcggccgctt aattaaggcc ggcctgcagc aaacccagaa    7020
ggtaattatc caagatgtag catcaagaat ccaatgttta cgggaaaaac tatggaagta    7080
ttatgtaagc tcagcaagaa gcagatcaat atgcggcaca tatgcaacct atgttcaaaa    7140
atgaagaatg tacagataca agatcctata ctgccagaat acgaagaaga atacgtagaa    7200
attgaaaaag aagaaccagg cgaagaaaag aatcttgaag acgtaagcac tgacgacaac    7260
aatgaaaaga agaagataag gtcggtgatt gtgaaagaga catagaggac acatgtaagg    7320
tggaaaatgt aagggcggaa agtaaccttat tcacaaagga atcttatccc ccactactta    7380
tccttttata ttttttccgtg tcattttttgc ccttgagttt tcctatataa ggaaccaagt    7440
tcggcatttg tgaaaacaag aaaaaaattttg gtgtaagcta ttttctttga agtactgagg    7500
atacaacttc agagaaattt gtaagtttgt agatctccat gtctccggag aggagaccag    7560
ttgagattag gccagctaca gcagctgata tggccgcggt ttgtgatatc gttaaccatt    7620
acattgagac gtctacagtg aactttagga cagagccaca acaccacaa gagtggattg    7680 atgatctaga gaggttgcaa gatagatacc cttggttggt tgctgaggtt gagggtgttg    7740
tggctggtat tgcttacgct gggccctgga aggctaggaa cgcttacgat tggacagttg    7800
agagtactgt ttacgtgtca cataggcatc aaaggttggg cctaggatcc acattgtaca    7860
cacatttgct taagtctatg gaggcgcaag gttttaagtc tgtggttgct gttataggcc    7920
ttccaaacga tccatctgtt aggttgcatg aggcttggg atacacagcc cggggtacat    7980
tgcgcgcagc tggatacaag catggtggat ggcatgatgt tggttttggg caaagggatt    8040
ttgagttgcc agctcctcca aggccagtta ggccagttac ccagatctga ggtaccctga    8100
gcttgagctt atgagcttat gagcttagag ctcggatcca ctagtaacgg ccgccagtgt    8160 gctgaattc gcccttgact agataggcgc ccagatcggc ggcaatagct tcttagcgcc    8220
atcccgggtt gatcctatct gtgttgaaat agttgcggtg ggcaaggctc tctttcagaa    8280
agacaggcgg ccaaaggaac ccaaggtgag gtgggctatg gctctcagtt ccttgtggaa    8340
gcgcttggtc taaggtgcag aggtgttagc gggatgaagc aaaagtgtcc gattgtaaca    8400
agatatgttg atcctacgta aggatattaa agtatgtatt catcactaat ataatcagtg    8460
tattccaata tgtactacga tttccaatgt ctttattgtc gccgtatgta atcggcgtca    8520
caaaataatc cccggtgact ttctttttaat ccaggatgaa ataatatgtt attataattt    8580
ttgcgatttg gtccgttata ggaattgaag tgtgcttgcg gtcgccacca ctcccatttc    8640
ataattttac atgtatttga aaaataaaaa tttatggtat tcaatttaaa cacgtatact    8700
tgtaaagaat gatatcttga aagaaatata gtttaaatat ttattgataa aataacaagt    8760
```

```
caggtattat agtccaagca aaaacataaa tttattgatg caagtttaaa ttcagaaata    8820
tttcaataac tgattatatc agctggtaca ttgccgtaga tgaaagactg agtgcgatat    8880
tatggtgtaa tacatagcgg ccgggtttct agtcaccggt taggatccgt ttaaactcga    8940
ggctagcgca tgcacataga cacacacatc atctcattga tgcttggtaa taattgtcat    9000
tagattgttt ttatgcatag atgcactcga aatcagccaa ttttagacaa gtatcaaacg    9060
gatgtgactt cagtacatta aaaacgtccg caatgtgtta ttaagttgtc taagcgtcaa    9120
tatttaatt cttaacaatc aatattttaa ttcttaaact ttattaaatc taacaataaa     9180
ctgtaagaac taattcttaa acttcaataa acaatactgc gttttagtaa ttaaattaat    9240
aatatataga tatagatata taatttgtca acatattctt acctatttt ccattgaaat     9300
atgttagcaa gttcaaaaaa agttttgaca aaaaactcta ctatcttttg tttcatttac    9360
tttatgtgag ggatataata gtaatataac atttagttta tttaaagaaa ataaaaaagt    9420
taatttctct ttctgccact gatactctat ggtggagaga tccgatgcag tggtggagcc    9480
tggcctcgac acataagtgt gacgacgcag ctgttgaaga gatctgattc gacggtgggg    9540
taatgcatgg tggttgacag gttgatgggt ggagaagacg taattgctac cgccgtcaac    9600
ggaggaagga gcaaagatgt ctcgtatgtg aaaattatgc ggttgagatg ccgtttcatt    9660
cccttttaaaa aaatccctttg atggttgcaa tgcaaattaa aaattgaaaa ataattaat    9720
tgttcaaatt aaagatttag catgaaaaaa aaaacactta attgtgccca tgactccatg    9780
acctgcgtaa cttgggaagg aaaggaattt ttttgctaaa ggaaggcatg ggaagatgag    9840
agaggagaga gaatcagtgg aagtgagaga aattaacttt ttgtttttta aaaactaaat    9900
attatattac tattatatat atatatatat atatataaaa gatttttttag ctggattctt   9960
gatataaaaa atttctcacc atatttatta ttatatattt ttttggagat ctcaaaaaag   10020
gaagttggat ttcttctcaa taactctaaa aaattattcc tatttcaaaa aatatttttt   10080
atgtctttct ctaattgatg aataatatct atttaagtat attttattgt gaaatccaca   10140
aaagtgactg ataaatctaa tttaggatct accattagag aaaaataaat aaattcttat   10200
attatatgtg at                                                      10212

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
tggaagaaca aagagattga cgca                                            24

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
gtaatacgac tcactatagg gc                                              22

<210> SEQ ID NO 4
<211> LENGTH: 28
<212> TYPE: DNA
<213> ORGANISM: Artificial Sequence
```

```
<220> FEATURE:
<223> OTHER INFORMATION: Primer

<400> SEQUENCE: 4
acgaaatatt acatgccaga agagtcgc                                              28

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
actatagggc acgcgtggt                                                        19

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ccgtagatga aagactgagt gcga                                                  24

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
ccgtagatga aagactgagt gcgatattat                                            30

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cccttgcata gtcacgtttg                                                       20

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
gtgttgccca gggaaga                                                          17

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
gctacttgct cttgtcgtaa gtca                                                  24
```

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
atgttgaagc caggctgc                                                    18

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gggcctaact tttggtgtga tg                                               22

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
tacttgctct tgtcgtaagt caataaatt                                        29

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
gaacttgcta acatatttca atgga                                            25

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ccagttaggc cagttaccca                                                  20

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
gagtatcagt ggcagaaaga gaaat                                            25

<210> SEQ ID NO 17
<211> LENGTH: 20
<212> TYPE: DNA
<213> ORGANISM: Artificial Sequence
<220> FEATURE:
<223> OTHER INFORMATION: Primer

```
<400> SEQUENCE: 17
cagggatgtg atggttcaat                                              20

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
ttagatttat cagtcacttt tgtggat                                      27

<210> SEQ ID NO 19
<211> LENGTH: 32
<212> TYPE: DNA
<213> ORGANISM: Artificial Sequence
<220> FEATURE:
<223> OTHER INFORMATION: Primer

<400> SEQUENCE: 19
ttctgctttt gtttctatat tagtgtagtt aa                                32

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
tggtagatcc taaattagat ttatcagtca                                   30

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
cttatgcact catatccgta tccg                                         24

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
atggaccgag ttggttcggt ttat                                         24

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
ataaaccgaa ccaactcggt ccat                                         24
```

```
<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
tcccaacttg ctctgagaat acac                                          24

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
gtgtattctc agagcaagtt ggga                                          24

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
caatcgtaag cgttcctagc cttc                                          24

<210> SEQ ID NO 27
<211> LENGTH: 24
<212> TYPE: DNA
<213> ORGANISM: Artificial Squence
<220> FEATURE:
<223> OTHER INFORMATION: Primer

<400> SEQUENCE: 27
gaaggctagg aacgcttacg attg                                          24

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
ccactgcatc ggatctctcc acca                                          24

<210> SEQ ID NO 29
<211> LENGTH: 710
<212> TYPE: DNA
<213> ORGANISM: Artificial Sequence
<220> FEATURE:
<223> OTHER INFORMATION: Flanking SNP Marker
<220> FEATURE:
<221> NAME/KEY: misc_feature
<222> LOCATION: (59)..(59)
<223> OTHER INFORMATION: n is c or g

<400> SEQUENCE: 29
tcatcgaagt tgagggcccc cgcggaaaat tggtgcgaga cttcaagcac ttgaatctng    60
attttcagct catcactgac gaaaacggta aaaggaagct gaaggtggag gcctggttcg   120
gttctcggaa aacatccgcc gccattcgca ccgccctgag ccacgtggag aatctgatca   180
```

```
ccggcgtcac caagggctac cgctacaaaa tgaggttcgt ttatgcccat tttcccatca      240
acgcaagcat cggcaacgac aacaagtcta ttgagatcag aaatttcctt ggcgaaaaga      300
aggtacttta ctctcttcat ctctatttct tttaattart ttatttattt tcttaatctt      360
ttgctactag gaaataaatt gtgrtattag gtttagtgat tgatttgstt attacgtgta      420
tcattaggtg agaaaagtgg accttcttaa cggtgtttcc gttgttcgat ctgaaaaagt      480
taaagatgaa ttgattttgg atgggaacga cattgaactt gtttctaggt cctgtgctct      540
cattaaccag gtttaatctt tctmcatgcr catgtttcca tacaattttt tctcaattt      600 ggtattggtt tagggtttaa ttaattgttt atttatttgt ttgttacaga aatgccatgt      660 taaaagaag gatatcagga aatttctcga tggcatttat gttagtgaga               710
```

<210> SEQ ID NO 30
<211> LENGTH: 786
<212> TYPE: DNA
<213> ORGANISM: Artificial Sequence
<220> FEATURE:
<223> OTHER INFORMATION: Flanking SNP Marker
<220> FEATURE:
<221> NAME/KEY: misc_feature
<222> LOCATION: (116)..(116)
<223> OTHER INFORMATION: n is a or c

<400> SEQUENCE: 30

```
acagaatttc tgatcacact agccttgatt ttcactatct aaaacacatt tctttgtcct      60
acattctttc ctttcttcta ctcctcatct tgggtactca aactctcttc cctaanaagg     120
attacaaaaa caaagtata tcgagttgtt agaaaagca agaaatagaa actccacctc      180
tacaacgttt tcttaattgc gtccatgagc atcacttcct gcagttttgc ggttcaggta      240
acgaatgaca gcatcctcaa ccctgaagat attacaaaaa agaacacaaa caaattagaa      300 aatatttga caaaaaatat tatataatat tgtttgccct acatgacaca tatatcaatt      360
aaggattggg atgaaggggg ggcatacagc ctacagggta tccatgtcat aacttataat      420
ttctctgtat gataaataat ctatccaaca atttcatagt gaagccctat ggtattgtat      480
tacaattcct accagttgcc acttaagaat ggacacgcct gacacatcaa aatctgaaat      540
gaaatgtctt ggttttttc tgagtcacgt tgtgtctaac acaagtgtct ggtatagatg      600
cagcttcttt tttatgtgta tgattgtcaa catattaaac tcccaacttt agcaagtaaa      660
tactcacatt caggtcacaa ccgtactaaa caaacaagtg tattatggat atatatacct      720
aacaacaaaa agagaaaagg tcaagtgtca tcataatgct taccatggtt gatgaagaat      780
cagaac                                                                786
```

AAD-12 EVENT 416, RELATED TRANSGENIC SOYBEAN LINES, AND EVENT-SPECIFIC IDENTIFICATION THEREOF

CROSS-REFERENCE TO RELATED APPLICATIONS

This application is a national phase application, filed pursuant to 35 U.S.C. § 371, of PCT application No. PCT/US2010/058001, filed on Nov. 24, 2010, which claims the benefit of U.S. Provisional Application No. 61/263,950, filed on Nov. 24, 2009. The prior applications are incorporated herein by reference in their entirety.

BACKGROUND OF THE INVENTION

The aad-12 gene (originally from *Delftia acidovorans*) encodes the aryloxyalkanoate dioxygenase (AAD-12) protein. The trait confers tolerance to 2,4-dichlorophenoxyacetic acid, for example, and to pyridyloxyacetate herbicides. The aad-12 gene, itself, for herbicide tolerance in plants was first disclosed in WO 2007/053482.

The expression of heterologous or foreign genes in plants is influenced by where the foreign gene is inserted in the chromosome. This could be due to chromatin structure (e.g., heterochromatin) or the proximity of transcriptional regulation elements (e.g., enhancers) close to the integration site (Weising et al., Ann. Rev. Genet 22:421-477, 1988), for example. The same gene in the same type of transgenic plant (or other organism) can exhibit a wide variation in expression level amongst different events. There may also be differences in spatial or temporal patterns of expression. For example, differences in the relative expression of a transgene in various plant tissues may not correspond to the patterns expected from transcriptional regulatory elements present in the introduced gene construct.

Thus, large numbers of events are often created and screened in order to identify an event that expresses an introduced gene of interest to a satisfactory level for a given purpose. For commercial purposes, it is common to produce hundreds to thousands of different events and to screen those events for a single event that has desired transgene expression levels and patterns. An event that has desired levels and/or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

U.S. Patent App. 20090130071 relates to soybean event MON87701 and methods for detection. U.S. Patent Apps. 20090036308 and 20080051288 relate to soybean event 3560.4.3.5 and methods for detection. U.S. Patent App. 20080312082 relates to soybean event DP-305423-1 and methods for detection. U.S. Patent App. 20060282915 relates to soybean event MON89788 and methods for detection.

AAD-12 soybeans having the specific event disclosed herein have not previously been disclosed.

BRIEF SUMMARY OF THE INVENTION

The present invention is related to the AAD-12 soybean (*Glycine max*) event designated DAS-68416-4 having seed deposited with American Type Culture Collection (ATCC) with Accession No. PTA-10442, and progeny derived thereof. Other aspects of the invention comprise the progeny plants, soybeans, seeds, and/or regenerable parts of the plants and seeds and progeny of soybean event DAS-68416-4, as well as food or feed products made from any thereof. The invention also includes plant parts of soybean event DAS-68416-4 that include, but are not limited to, pollen, ovule, flowers, shoots, roots, and leaves, and nuclei of vegetative cells, pollen cells, and egg cells. The invention further relates to soybean plants having tolerance to phenoxy auxinic and/or aryloxyalkanoate herbicides (whether those herbicides are applied over-the-top of the soybean plants, to the adjacent or nearby soil, or to adjacent or nearby weeds), novel genetic compositions of soybean event DAS-68416-4, and aspects of agronomic performance of soybean plants comprising soybean event DAS-68416-4.

This invention relates in part to plant breeding and herbicide tolerant plants. This invention includes a novel aad-12 transformation event in soybean plants comprising a polynucleotide sequence, as described herein, inserted into a specific site within the genome of a soybean cell.

In some embodiments, said event/polynucleotide sequence can be "stacked" with other traits, including, for example, other herbicide tolerance gene(s) and/or insect-inhibitory proteins. However, the subject invention includes plants having the single event, as described herein. In a particular embodiment of the invention, one or more herbicide tolerant traits are stacked with soybean event DAS-68416-4 for purposes of controlling various herbicide resistant weeds (e.g., glyphosate resistant weeds).

Additionally, the subject invention provides assays for detecting the presence of the subject event in a sample (of soybeans, for example). The assays can be based on the DNA sequence of the recombinant construct, inserted into the soybean genome, and on the genomic sequences flanking the insertion site. Kits and conditions useful in conducting the assays are also provided.

Thus, the subject invention relates in part to the cloning and analysis of the DNA sequences of a whole aad-12 insert, and the border regions thereof (in transgenic soybean lines). These sequences are unique. Based on these insert and border sequences, event-specific primers were generated. PCR analysis demonstrated that these events can be identified by analysis of the PCR amplicons generated with these event-specific primer sets. Thus, these and other related procedures can be used to uniquely identify soybean lines comprising the event of the subject invention.

BRIEF DESCRIPTION OF THE FIGURES

FIG. 1 shows a plasmid map of pDAB4468.

FIG. 2 shows a diagram of Genomic DNA of the soybean event where DAS-68416-4 was digested with EcoRV, or Pvu II and used to generate corresponding GENOMEWALKER™ libraries, which were used as templates to amplify the target DNA sequences.

FIG. 3 depicts the primer locations for confirming the full length sequence of the soybean Event DAS-68416-4 from 5' to 3' borders.

FIG. 4 depicts the primer locations for confirming the full length sequence of the soybean Event DAS-68416-4 from 5' to 3' borders.

FIG. 5 depicts the primer locations for confirming the insertion site sequence of the AAD-12 soybean event DAS-68416-4.

FIG. 6 shows expression levels through the plant life-cycle.

BRIEF DESCRIPTION OF THE TABLES

Table 1 provides the residue numbering with respect to SEQ ID NO:1 of the insert and flanking sequences for Event DAS-68416-4.

Table 2 provides the location and length of probes used in Southern analysis.

Table 3 provides the predicted and observed hybridizing fragments in Southern blot analysis.

Table 4 provides the conditions for genome walking soybean Event DAS-68416-4 to amplify the flanking border regions.

Table 5 provides the conditions for standard PCR amplification of the border regions and event-specific sequences in soybean Event DAS-68416-4.

Table 6 provides the primer description for amplicons 1-4 for T-strand insert.

Table 7 provides the PCR mixture for standard PCR amplification of the border regions and event specific sequences in soybean Event DAS-68416-4.

Table 8 provides the summary of AAD-12 protein levels in tissues collected from soybean Event DAS-68416-4 produced in the U.S. and Canada during 2008.

Table 9 provides the location and length of probes used in Southern analysis.

Table 10 provides the predicted and observed hybridizing fragments in Southern blot analysis.

Table 11 provides the agronomic parameters evaluated in Experiment 1.

Table 12 provides the analysis of agronomic characteristics from Experiment 1.

Table 13 provides the data collected in agronomic and yield trials, 2009.

Table 14 provides a summary of the 2009 agronomic characteristics results across locations.

Table 15 provides the analysis of disease incidence and insect damage from Experiment 1.

Table 16 provides the disease and insect stressors observed in trials of DAS-68416-4 and conventional soybean.

Table 17 provides the germination of soybean Event DAS-68416-4 seeds under warm and cold conditions.

Table 18 provides the summary of the proximate, fiber and mineral analysis of soybean forage.

Table 19 provides the summary of the proximate and fiber analysis of soybean grain.

Table 20 provides the summary of the mineral analysis of soybean grain.

Table 21 provides the summary of the amino acid analysis of soybean grain.

Table 22 provides the summary of the fatty acid analysis of soybean grain.

Table 23 provides the summary of vitamin analysis of soybean grain.

Table 24 provides the summary of isoflavone analysis of soybean grain.

Table 25 provides the summary of anti-nutrient analysis of soybean grain.

Table 26 provides site and treatment information for 2,4-D preemergence tolerance trials.

Table 27 illustrates DAS-68416-4 Soybean Tolerance to Preemergence Applications of 2,4-D.

BRIEF DESCRIPTION OF THE SEQUENCES

SEQ ID NO:1 provides insert and flanking sequences for the subject soybean Event DAS-68416-4.

SEQ ID NOs:2-28 are primers as described herein.

SEQ ID NOs:29 and 30 are flanking SNP markers BARC-019093-03299 and BARC-044607-08736 as described herein.

DETAILED DESCRIPTION OF THE INVENTION

This invention relates in part to plant breeding and herbicide tolerant plants. This invention includes novel transformation events of soybean plants (soybean) comprising a subject aad-12 polynucleotide sequences, as described herein, inserted into specific site within the genome of a soybean cell. In some embodiments, said polynucleotide sequence can be "stacked" with other traits (such as other herbicide tolerance gene(s) and/or gene(s) that encode insect-inhibitory proteins, for example. However, the subject invention includes plants having a single event, as described herein.

Additionally, the subject invention provides assays for detecting the presence of the subject event in a sample. Aspects of the subject invention include methods of designing and/or producing any diagnostic nucleic acid molecules exemplified or suggested herein, particularly those based wholly or partially on the subject flanking sequences.

More specifically, the subject invention relates in part to transgenic soybean event DAS-68416-4, plant lines comprising these events, and the cloning and analysis of the DNA sequences of this insert, and/or the border regions thereof. Plant lines of the subject invention can be detected using sequences disclosed and suggested herein.

In some embodiments, this invention relates to herbicide-tolerant soybean lines, and the identification thereof. The subject invention relates in part to detecting the presence of the subject event in order to determine whether progeny of a sexual cross contain the event of interest. In addition, a method for detecting the event is included and is helpful, for example, for complying with regulations requiring the pre-market approval and labeling of foods derived from recombinant crop plants, for example. It is possible to detect the presence of the subject event by any well-known nucleic acid detection method such as polymerase chain reaction (PCR) or DNA hybridization using nucleic acid probes. An event-specific PCR assay is discussed, for example, by Windels et al. (Med. Fac. Landbouww, Univ. Gent 64/5b: 459462, 1999). This related to the identification of glyphosate tolerant soybean event 40-3-2 by PCR using a primer set spanning the junction between the insert and flanking DNA. More specifically, one primer included sequence from the insert and a second primer included sequence from flanking DNA.

Soybean was modified by the insertion of the aad-12 gene, derived from *Delftia acidovorans*, which encodes the aryloxyalkanoate dioxygenase (AAD-12) protein. The trait confers tolerance to 2,4-dichlorophenoxyacetic acid and pyridyloxyacetate herbicides and may be used as a selectable marker during plant transformation and in breeding nurseries.

More specifically, described herein is the AAD12 event pDAB4468-0416, and its selection and characterization for stability and expression at whole plant and molecular levels from generation to generation.

The subject synthetic gene (aad-12) used according to the subject invention was derived from *Delftia acidovorans* and encodes an enzyme capable of deactivating several herbicides with an aryloxyalkanoate moiety, including phenoxy auxin (e.g., 2,4-D, MCPA), as well as pyridyloxy auxins (e.g., fluroxypyr, triclopyr). The aad-12 gene, driven by atUbi10 promoters, was introduced into the soybean line Maverick via *Agrobacterium tumefaciens* techniques. The transgenic T0 plants were self-pollinated for 4-6 generations. In parallel, the aad-12 gene was also introgressed into elite soybean varieties. All transgenic events were characterized for 4-5 generations in contained and regulated field nursery and lab settings.

Both ends of event pDAB4468-0416 insertion have been sequenced and characterized. Event specific assays were developed. It has also been mapped onto the soybean genome (soybean chromosome 4); flanking SNP markers are described herein as SEQ ID NOS: 29 and 30. The event is being introgressed into further elite lines. The event provides tolerance to 2,4-D and glufosinate.

Driven by atUbi10 promoter, over 100 AAD12 T1 Maverick soybean events were generated via *Agrobacterium tumefaciens* techniques. Event pDAB4468-0416 was selected through single lineage selection of five self-pollinated generations and a few backcrossing generations. It was morphologically normal and was tolerant to 2240 g ae/ha of 2,4-D spray at V3 through every self-pollinated generation. The event was inherited as a single dominated gene and had normal Mendelian segregations in self-pollinated generations and backcross generations as well.

The event pDAB4468-0416 was found to have single integration with a full-length plant transcription unit (PTU). There were no anti-biotic resistance gene sequence found from the vector backbone, and no gene silencing detected through several generations at aad-12 gene homozygous and hemizygous status. The aad-12 gene was expressing at expected levels that led to the levels of 2,4-D tolerances. The event has been expressing the aad-12 gene stably throughout generations and among sibling lineages within a given generation.

As alluded to above in the Background section, the introduction and integration of a transgene into a plant genome involves some random events (hence the name "event" for a given insertion that is expressed). That is, with many transformation techniques such as *Agrobacterium* transformation, the "gene gun," and WHISKERS, it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

As "events" are originally random events, as part of this disclosure at least 2500 seeds of a soybean line comprising the event have been deposited and made available to the public without restriction (but subject to patent rights), with the American Type Culture Collection (ATCC), 10801 University Boulevard, Manassas, Va., 20110. The deposit has been designated as ATCC Deposit No. PTA-10442. 25 vials of *Glycine max* seeds (AAD-12 event pDAB4468-0416) were deposited on behalf of Dow AgroSciences LLC on Oct. 22, 2009. The deposit was tested on Nov. 2, 2009, and on that date, the seeds were viable. This deposit was made and will be maintained in accordance with and under the terms of the Budapest Treaty with respect to seed deposits for the purposes of patent procedure. The deposit will be maintained without restriction at the ATCC depository, which is a public depository, for a period of 30 years, or five years after the most recent request, or for the effective life of the patent, whichever is longer, and will be replaced if it becomes nonviable during that period.

The deposited seeds are part of the subject invention. Clearly, soybean plants can be grown from these seeds, and such plants are part of the subject invention. The subject invention also relates to DNA sequences contained in these soybean plants that are useful for detecting these plants and progeny thereof. Detection methods and kits of the subject invention can be directed to identifying any one, two, or even all three of these events, depending on the ultimate purpose of the test.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR § 1.822 is used.

As used herein, the term "progeny" denotes the offspring of any generation of a parent plat which comprises AAD-12 soybean event DAS-68416-4.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the soybean native genome flanking the insertion point, the identification or detection of one or the other junction sequences in a plant's genetic material being sufficient to be diagnostic for the event. Included are the DNA sequences that span the insertions in herein-described soybean events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates to the identification of such flanking, junction, and insert sequences. Related PCR primers and amplicons are included in the invention. According to the subject invention, PCR analysis methods using amplicons that span across inserted DNA and its borders can be used to detect or identify commercialized transgenic soybean varieties or lines derived from the subject proprietary transgenic soybean lines.

During the process of introducing an insert into the genome of plant cells, it is not uncommon for some deletions or other alterations of the insert and/or genomic flanking sequences to occur. Thus, the relevant segment of the plasmid sequence provided herein might comprise some minor variations. The same would be true for the flanking sequences provided herein. Thus, a plant comprising a polynucleotide having some range of identity with the subject flanking and/or insert sequences is within the scope of the subject invention. Identity to the sequence of the present invention can be a polynucleotide sequence having at least 65% sequence identity, more preferably at least 70% sequence identity, more preferably at least 75% sequence identity, more preferably at least 80% identity, and more preferably at least 85% 86%, 87%, 88%, 89%, 90%, 91%, 92%, 93%, 94%, 95%, 96%, 97%, 98%, 99% sequence identity with a sequence exemplified or described herein. Hybridization and hybridization conditions as provided herein can also be used to define such plants and polynucleotide sequences of the subject invention. The sequence of the flanking sequences plus insert sequence can be confirmed with reference to the deposited seed.

The entire sequences of each of these inserts, together with portions of the respective flanking sequences, are provided herein as SEQ ID NO:1. The coordinates of the insert and flanking sequences for this event with respect to SEQ ID NO:1 (10,212 basepairs total) are printed below in Table 1. This is discussed in more detail in Example 3, for example.

TABLE 1

Residue numbering, with respect to SEQ ID NO: 1, of the insert and flanking sequences for Event DAS-68416-4.

|  | 5' Flanking | Insert | 3' Flanking |
| --- | --- | --- | --- |
| residue #s (SEQ: 1): | 1-2730 | 2731-9121 | 9122-10,212 |
| length (bp): | 2730 bp | 6391 bp | 1091 bp |

These sequences (particularly the flanking sequences) are unique. Based on these insert and border sequences, event-specific primers were generated. PCR analysis demonstrated that these soybean lines can be identified in different soybean genotypes by analysis of the PCR amplicons generated with these event-specific primer sets. Thus, these and other related procedures can be used to uniquely identify these soybean lines. The sequences identified herein are unique.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit soybean breeding programs as well as quality control, especially for commercialized transgenic soybean seeds. PCR detection kits for these transgenic soybean lines can also now be made and used. This can also benefit product registration and product stewardship.

Furthermore, flanking soybean/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that the subject invention includes seeds available under ATCC Deposit No. PTA-10442. The subject invention also includes a herbicide-resistant soybean plant grown from a seed deposited with the ATCC under accession number PTA-10442. The subject invention further includes parts of said plant, such as leaves, tissue samples, seeds produced by said plant, pollen, and the like.

Still further, the subject invention includes descendant and/or progeny plants of plants grown from the deposited seed, preferably a herbicide-resistant soybean plant wherein said plant has a genome comprising a detectable wild-type genomic DNA/insert DNA junction sequence as described herein. As used herein, the term "soybean" means *Glycine max* and includes all varieties thereof that can be bred with a soybean plant.

This invention further includes processes of making crosses using a plant of the subject invention as at least one parent. For example, the subject invention includes an $F_1$ hybrid plant having as one or both parents any of the plants exemplified herein. Also within the subject invention is seed produced by such $F_1$ hybrids of the subject invention. This invention includes a method for producing an $F_1$ hybrid seed by crossing an exemplified plant with a different (e.g. in-bred parent) plant and harvesting the resultant hybrid seed. The subject invention includes an exemplified plant that is either a female parent or a male parent. Characteristics of the resulting plants may be improved by careful consideration of the parent plants.

A herbicide-tolerant soybean plant can be bred by first sexually crossing a first parental soybean plant consisting of a soybean plant grown from seed of any one of the lines referred to herein, and a second parental soybean plant, thereby producing a plurality of first progeny plants; and then selecting a first progeny plant that is resistant to a herbicide (or that possesses at least one of the events of the subject invention); and selfing the first progeny plant, thereby producing a plurality of second progeny plants; and then selecting from the second progeny plants a plant that is resistant to a herbicide (or that possesses at least one of the events of the subject invention). These steps can further include the back-crossing of the first progeny plant or the second progeny plant to the second parental soybean plant or a third parental soybean plant. A soybean crop comprising soybean seeds of the subject invention, or progeny thereof, can then be planted.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The DNA molecules of the present invention can be used as molecular markers in a marker assisted breeding (MAB) method. DNA molecules of the present invention can be used in methods (such as, AFLP markers, RFLP markers, RAPD markers, SNPs, and SSRs) that identify genetically linked agronomically useful traits, as is known in the art. The herbicide-resistance trait can be tracked in the progeny of a cross with a soybean plant of the subject invention (or progeny thereof and any other soybean cultivar or variety) using the MAB methods. The DNA molecules are markers for this trait, and MAB methods that are well known in the art can be used to track the hebicide-resistance trait(s) in soybean plants where at least one soybean line of the subject invention, or progeny thereof, was a parent or ancestor. The methods of the present invention can be used to identify any soybean variety having the subject event.

Methods of the subject invention include a method of producing a herbicide-tolerant soybean plant wherein said method comprises breeding with a plant of the subject invention. More specifically, said methods can comprise crossing two plants of the subject invention, or one plant of the subject invention and any other plant. Preferred methods further comprise selecting progeny of said cross by analyzing said progeny for an event detectable according to the subject invention. For example, the subject invention can be used to track the subject event through breeding cycles with plants comprising other desirable traits, such as agronomic traits such as those tested herein in various Examples. Plants comprising the subject event and the desired trait can be detected, identified, selected, and quickly used in further rounds of breeding, for example. The subject event/trait can also be combined through breeding, and tracked according to the subject invention, with an insect resistant trait(s) and/or with further herbicide tolerance traits. One preferred embodiment of the latter is a plant comprising the subject event combined with a gene encoding resistance to the herbicide dicamba.

Thus, the subject invention can be combined with, for example, traits encoding glyphosate resistance (e.g., resistant plant or bacterial EPSPS, GOX, GAT), glufosinate resistance (e.g., Pat, bar), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Regarding additional herbicides, some additional preferred ALS (also known as AHAS) inhibitors include the triazolopyrimidine sulfonanilides (such as cloransulam-methyl, diclosulam, florasulam, flumetsulam, metosulam, and penoxsulam), pyrimidinylthiobenzoates (such as bispyribac and pyrithiobac), and flucarbazone. Some preferred HPPD inhibitors include mesotrione, isoxaflutole, and sulcotrione. Some preferred PPO inhibitors include flumiclorac, flumioxazin, flufenpyr, pyraflufen, fluthiacet, butafenacil, carfentrazone, sulfentrazone, and the diphenylethers (such as acifluorfen, fomesafen, lactofen, and oxyfluorfen).

Additionally, AAD-12 alone or stacked with one or more additional HTC traits can be stacked with one or more additional input (e.g., insect resistance, fungal resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

The subject AAD-12 enzyme enables transgenic expression resulting in tolerance to combinations of herbicides that would control nearly all broadleaf and grass weeds. AAD-12 can serve as an excellent herbicide tolerant crop (HTC) trait to stack with other HTC traits (e.g., glyphosate resistance, glufosinate resistance, imidazolinone resistance, bromoxynil resistance, et al.), and insect resistance traits (Cry1F, Cry1Ab, Cry 34/45, et al.) for example. Additionally, AAD-12 can serve as a selectable marker to aid in selection of primary transformants of plants genetically engineered with a second gene or group of genes.

The AAD-12 gene of the subject invention also provides resistance to compounds that are converted to phenoxyacetate auxin herbicides (e.g. 2,4-DB, MCPB, etc.). The butyric acid moiety present in the 2,4-DB herbicide is converted through β-oxidation to the phytotoxic 2,4-dichlorophenoxyacetic acid. Likewise, MCPB is converted through β-oxidation to the phytotoxic MCPA. The butanoic acid herbicides are themselves nonherbicidal. They are converted to their respective acid from by β-oxidation within susceptible plants, and it is the acetic acid form of the herbicide that is phytotoxic. Plants incapable of rapid β-oxidation are not harmed by the butanoic acid herbicides. However, plants that are capable of rapid β-oxidation and can convert the butanoic acid herbicide to the acetic form are subsequently protected by AAD-12.

Methods of applying herbicides are known in the art. Such applications can include tank mixes of more than one herbicide. Some preferred herbicides for use according to the subject invention include phenoxy auxin herbicide such as 2,4-D; 2,4-DB; MCPA; MCPB. These can be stacked with one or more additional herbicide tolerance gene(s) and a corresponding herbicide (e.g. glyphosate and/or glufosinate). One, two, three, or more herbicides can be used in advantageous combinations that would be apparent to one skilled in the art having the benefit of the subject disclosure. One or more of the subject herbicides can be applied to a field/area prior to planting it with seeds of the subject invention. Such applications can be within 14 days, for example, of planting. One or more of the subject herbicides can also be applied at-plant and/or post-plant but pre-emergence. One or more of the subject herbicides can also be applied to the ground (for controlling weeds) or over the top of the weeds and/or transgenic plants of the subject invention. The subject herbicides can be rotated or used in combination to, for example, control or prevent weeds that might to tolerant to one herbicide but not another. Various application times for the subject three types of herbicides can be used in various ways as would be known in the art. The subject invention also provides methods for controlling AAD-12 volunteer plants. See concurrently filed PCT application entitled "CONTROL OF AAD DICOT VOLUNTEERS IN MONOCOT CROPS".

HTC traits of the subject invention can be used in novel combinations with other HTC traits (including but not limited to glyphosate tolerance). These combinations of traits give rise to novel methods of controlling weed (and like) species, due to the newly acquired resistance or inherent tolerance to herbicides (e.g., glyphosate). Thus, in addition to the HTC traits, novel methods for controlling weeds using herbicides, for which herbicide tolerance was created by said enzyme in transgenic crops, are within the scope of the invention.

Additionally, glyphosate tolerant crops grown worldwide are prevalent. Many times in rotation with other glyphosate tolerant crops, control of glyphosate-resistant volunteers may be difficult in rotational crops. Thus, the use of the subject transgenic traits, stacked or transformed individually into crops, provides a tool for controlling other HTC volunteer crops.

A preferred plant, or a seed, of the subject invention comprises in its genome the insert sequences, as identified herein, together with at least 20-500 or more contiguous flanking nucleotides on both sides of the insert, as identified herein. Unless indicated otherwise, reference to flanking sequences refers to those identified with respect to SEQ ID NO:1 (see Table 1 above). Again, SEQ ID NO:1 includes the heterologous DNA inserted in the original transformant and illustrative flanking genomic sequences immediately adjacent to the inserted DNA. All or part of these flanking sequences could be expected to be transferred to progeny that receives the inserted DNA as a result of a sexual cross of a parental line that includes the event.

The subject invention includes tissue cultures of regenerable cells of a plant of the subject invention. Also included is a plant regenerated from such tissue culture, particularly where said plant is capable of expressing all the morphological and physiological properties of an exemplified variety. Preferred plants of the subject invention have all the physiological and morphological characteristics of a plant grown from the deposited seed. This invention further comprises progeny of such seed and seed possessing the quality traits of interest.

Manipulations (such as mutation, further transfection, and further breeding) of plants or seeds, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when (i) it is predominantly derived from the initial variety, or from a variety that is itself predominantly derived from the initial variety, while retaining the expression of the essential characteristics that result from the genotype or combination of genotypes of the initial variety;

(ii) it is clearly distinguishable from the initial variety; and (iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial canola variety without the premium value traits grown in the same region.

"Agronomically elite" means that a line has desirable agronomic characteristics such as yield, maturity, disease resistance, and the like, in addition to the insect resistance due to the subject event(s). Agronomic traits, taken individually or in any combination, as set forth in Examples, below, in a plant comprising an event of the subject invention, are within the scope of the subject invention. Any and all of these agronomic characteristics and data points can be used to identify such plants, either as a point or at either end or both ends of a range of chracteristics used to define such plants.

As one skilled in the art will recognize in light of this disclosure, preferred embodiments of detection kits, for example, can include probes and/or primers directed to and/or comprising "junction sequences" or "transition sequences" (where the soybean genomic flanking sequence meets the insert sequence). For example, this includes a polynucleotide probes, primers, and/or amplicons designed to identify one or both junction sequences (where the insert meets the flanking sequence), as indicated in Table 1 above. One common design is to have one primer that hybridizes in the flanking region, and one primer that hybridizes in the insert. Such primers are often each about at least ~15 residues in length. With this arrangement, the primers can be used to generate/amplify a detectable amplicon that indicates the presence of an event of the subject invention. These primers can be used to generate an amplicon that spans (and includes) a junction sequence as indicated above.

The primer(s) "touching down" in the flanking sequence is typically not designed to hybridize beyond about 200 bases or beyond the junction. Thus, typical flanking primers would be designed to comprise at least 15 residues of either strand within 200 bases into the flanking sequences from the beginning of the insert. That is, primers comprising a sequence of an appropriate size from (or hybridizing to) residues ~2530-2730 and/or ~9122-9322 of SEQ ID NO:1 are within the scope of the subject invention. Insert primers can likewise be designed anywhere on the insert, but residues ~2731-2931 and ~8921-9121, can be used, for example, non-exclusively for such primer design.

One skilled in the art will also recognize that primers and probes can be designed to hybridize, under a range of standard hybridization and/or PCR conditions, to a segment of SEQ ID NO:1 (or the complement), and complements thereof, wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

It should be noted that errors in PCR amplification can occur which might result in minor sequencing errors, for example. That is, unless otherwise indicated, the sequences listed herein were determined by generating long amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice than any adjustments needed due to these types of common sequencing errors or discrepancies are within the scope of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the "insert" are illustrated in the Figures and are discussed in more detail below in the Examples. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a soybean plant. DNA sequences are provided that comprise the subject transgene/genomic insertion region junction sequence provided herein (between residues 2730-2731 and 9121-9122 of SEQ ID NO:1), segments thereof, and complements of the exemplified sequences and any segments thereof. The insertion region junction sequence spans the junction between heterologous DNA inserted into the genome and the DNA from the soybean cell flanking the insertion site. Such sequences can be diagnostic for the given event.

Based on these insert and border sequences, event-specific primers can be generated. PCR analysis demonstrated that soybean lines of the subject invention can be identified in different soybean genotypes by analysis of the PCR amplicons generated with these event-specific primer sets. These and other related procedures can be used to uniquely identify these soybean lines. Thus, PCR amplicons derived from such primer pairs are unique and can be used to identify these soybean lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of soybean genomic sequence from one or more of the three aforementioned soybean plants and/or sequences that are useful as primer sequences for the production of an amplicon product diagnostic for one or more of these soybean plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:1 and segments thereof), or complements thereof, and a similar length of flanking soybean DNA sequence from these sequences, or complements thereof. Such sequences are useful as DNA primers in DNA amplification methods. The amplicons produced using these primers are diagnostic for any of the soybean events referred to herein. Therefore, the invention also includes the amplicons produced by such DNA primers and homologous primers.

This invention also includes methods of detecting the presence of DNA, in a sample, that corresponds to the soybean event referred to herein. Such methods can comprise: (a) contacting the sample comprising DNA with a primer set that, when used in a nucleic acid amplification reaction with DNA from at least one of these soybean events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to at least one of said events, wherein said method comprises: (a) contacting the sample comprising DNA with a probe that hybridizes under stringent hybridization conditions with DNA from at least one of said soybean events and which does not hybridize under the stringent hybridization conditions with a control soybean plant (non-event-of-interest DNA); (b) subjecting the sample and probe to stringent hybridization conditions; and (c) detecting hybridization of the probe to the DNA.

In still further embodiments, the subject invention includes methods of producing a soybean plant comprising the aad-12 event of the subject invention, wherein said method comprises the steps of: (a) sexually crossing a first parental soybean line (comprising an expression cassettes of the present invention, which confers said herbicideresistance trait to plants of said line) and a second parental soybean line (that lacks this herbicide tolerance trait) thereby producing a plurality of progeny plants; and (b) selecting a progeny plant by the use of molecular markers. Such methods may optionally comprise the further step of back-crossing the progeny plant to the second parental soybean line to producing a true-breeding soybean plant that comprises said insect tolerance trait.

According to another aspect of the invention, methods of determining the zygosity of progeny of a cross with any one (or more) of said three events are provided. Said methods can comprise contacting a sample, comprising soybean DNA, with a primer set of the subject invention. Said primers, when used in a nucleic-acid amplification reaction with genomic DNA from at least one of said soybean events, produces a first amplicon that is diagnostic for at least one of said soybean events. Such methods further comprise performing a nucleic acid amplification reaction, thereby producing the first amplicon; detecting the first amplicon; and contacting the sample comprising soybean DNA with said primer set (said primer set, when used in a nucleic-acid amplification reaction with genomic DNA from soybean plants, produces a second amplicon comprising the native soybean genomic DNA homologous to the soybean genomic region; and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject soybean event DNA in a sample and can be applied to methods for breeding soybean plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said soybean events, whether from a soybean plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence as set forth herein in one of the exemplified sequences, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject soybean event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of the present invention. Following this method, an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the soybean genome that is excellent for an insertion, the subject invention also comprises a soybean seed and/or a soybean plant comprising at least one non-aad12 insert in the general vicinity of this genomic location. One option is to substitute a different insert in place of the aad-12 insert exemplified herein. In these generally regards, targeted homologous recombination, for example, can be used according to the subject invention. This type of technology is the subject of, for example, WO 03/080809 A2 and the corresponding published U.S. application (U.S. 2003/0232410). Thus, the subject invention includes plants and plant cells comprising a heterologous insert (in place of or with multi-copies of aad-12), flanked by all or a recognizable part of the flanking sequences identified herein (e.g. residues 1-2730 and 9122-10,212 of SEQ ID NO:1). An additional copy (or additional copies) of an aad-12 gene could also be targeted for insertion in this/these manners.

Methods to integrate a polynucleotide sequence within a specific chromosomal site of a plant cell via homologous recombination have been described within the art. For instance, site specific integration as described in U.S. Patent Application Publication No. 2009/0111188 A1 describes the use of recombinases or integrases to mediate the introduction of a donor polynucleotide sequence into a chromosomal target. In addition, International Patent Application No. WO 2008/021207 describes zinc finger mediated-homologous recombination to integrate one or more donor polynucleotide sequences within specific locations of the genome. The use of recombinases such as FLP/FRT as described in U.S.

Pat. No. 6,720,475 or CRE/LOX as described in U.S. Pat. No. 5,658,772 can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060.

Other various methods for site specific integration within plant cells are generally known and applicable (Kumar et al., Trands in Plant Sci. 6(4) (2001) pp. 155-159). Furthermore, site-specific recombination systems which have been identified in several prokaryotic and lower eukaryotic organisms may be applied to use in plants. Examples of such systems include, but are not limited too: the R/RS recombinase system from the pSR1 plasmid of the yeast *Zygosaccharomyces rouxii* (Araki et al. (1985) J. Mol. Biol. 182: 191-203), and the Gin/gix system of phage Mu (Maeser and Kahlmann (1991) Mol. Gen. Genet. 230: 170-176).

In some embodiments of the present invention, it can be desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. The newly integrated transgenes should maintain the transgene expression characteristics of the existing transformants. Moreover, the development of assays for the detection and confirmation of the newly integrated event would be overcome as the genomic flanking sequences and chromosomal location of the newly integrated event are already identified. Finally, the integration of a new transgene into a specific chromosomal location which is linked to an existing transgene would expedite the introgression of the transgenes into other genetic backgrounds by sexual out-crossing using conventional breeding methods.

In some embodiments of the present invention, it can be desirable to excise polynucleotide sequences from a transgenic event. For instance transgene excision as described in Provisional U.S. Patent Application No. 61/297,628 describes the use of zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

The subject invention discloses herein a specific site on chromosome 4 in the soybean genome that is excellent, for insertion of heterologous nucleic acids. Also disclosed is a 5' molecular marker, a 3' molecular marker, a 5' flanking sequence, and a 3' flanking sequence useful in identifying the location of a targeting site on chromosome 4. Thus, the subject invention provides methods to introduce heterologous nucleic acids of interest into this pre-established target site or in the vicinity of this target site. The subject invention also encompasses a soybean seed and/or a soybean plant comprising any heterologous nucleotide sequence inserted at the disclosed target site or in the general vicinity of such site. One option to accomplish such targeted integration is to excise and/or substitute a different insert in place of the pat expression cassette exemplified herein. In this general regard, targeted homologous recombination, for example and without limitation, can be used according to the subject invention.

As used herein gene, event or trait "stacking" is combining desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while, homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.

AAD-12 aryloxyalkanoate dioxygenase-1
bp base pair
° C. degrees Celcius
DNA deoxyribonucleic acid
DIG digoxigenin
EDTA ethylenediaminetetraacetic acid
kb kilobase
µg microgram
µL microliter
mL milliliter
M molar mass
OLP overlapping probe
PCR polymerase chain reaction
PTU plant transcription unit
SDS sodium dodecyl sulfate
SOP standard operating procedure
SSC a buffer solution containing a mixture of sodium chloride and sodium citrate, pH 7.0
TBE a buffer solution containing a mixture of Tris base, boric acid and EDTA, pH 8.3
V volts

EXAMPLES

Example 1

Transformation and Selection of the aad-12 Soybean Event DAS-68416-4

Transgenic soybean (*Glycine max*) Event DAS-68416-4 was generated through *Agrobacterium*-mediated transformation of soybean cotyledonary node explants. The disarmed *Agrobacterium* strain EHA101 (Hood et al., 2006), carrying the binary vector pDAB4468 (FIG. 1) with the selectable marker (pat) and the gene of interest (aad-12) within the T-strand DNA region, was used to initiate transformation.

*Agrobacterium*-mediated transformation was carried out using a modified procedure of Zeng et al. (Zeng et al., 2004). Briefly, soybean seeds (cv Maverick) were germinated on basal media and cotyledonary nodes were isolated and infected with *Agrobacterium*. Shoot initiation, shoot elongation, and rooting media were supplemented with cefotaxime, timentin and vancomycin for removal of *Agrobacterium*. Glufosinate selection was employed to inhibit the growth of non-transformed shoots. Selected shoots were transferred to rooting medium for root development and then transferred to soil mix for acclimatization of plantlets.

Terminal leaflets of selected plantlets were leaf painted with glufosinate to screen for putative transformants. The screened plantlets were transferred to the greenhouse, allowed to acclimate and then leaf-painted with glufosinate to reconfirm tolerance and deemed to be putative transformants. The screened plants were sampled and molecular analyses for the confirmation of the selectable marker gene and/or the gene of interest were carried out. $T_0$ plants were allowed to self fertilize in the greenhouse to give rise to $T_1$ seed.

The $T_1$ plants were backcrossed and introgressed into elite germplasm (Maverick). This event, soybean Event DAS-68416-4, was generated from an independent transformed isolate. The event was selected based on its unique characteristics such as single insertion site, normal Mendelian segregation and stable expression, and a superior combination of efficacy, including herbicide tolerance and agronomic performance in broad genotype backgrounds and across multiple environmental locations. The following examples contain the data which were used to characterize soybean Event DAS-68416-4.

Example 2

Soybean Event DAS-68416-4 Characterization via Southern Blot

Southern blot analysis was used to establish the integration pattern of soybean Event DAS-68418-4. These experiments generated data which demonstrated the integration and integrity of the aad-12 transgene within the soybean genome. Soybean Event DAS-68418-4 was characterized as a full length, simple integration event containing a single copy of the aad-12 PTU from plasmid pDAB4468.

Southern blot data suggested that a pDAB4468 T-strand fragment inserted into the genome of soybean Event DAS-68418-4. Detailed Southern blot analysis was conducted using a probe specific to the aad-12 gene, contained in the T-strand integration region of pDAB4468, and descriptive restriction enzymes that have cleavage sites located within the plasmid and produce hybridizing fragments internal to the plasmid or fragments that span the junction of the plasmid with soybean genomic DNA (border fragments). The molecular weights indicated from the Southern hybridization for the combination of the restriction enzyme and the probe were unique for the event, and established its identification patterns. These analyses also showed that the plasmid fragment had been inserted into soybean genomic DNA without rearrangements of the aad-12 PTU.

Example 2.1

Soybean Leaf Sample Collection and Genomic DNA (gDNA) Isolation

Genomic DNA was extracted from leaf tissue harvested from individual soybean plants containing soybean Event DAS-68416-4. In addition, gDNA was isolated from a conventional soybean plant, Maverick, which contains the genetic background that is representative of the substance line, absent the aad-12 gene.

Individual genomic DNA was extracted from lyophilized leaf tissue following the standard CTAB method. Following extraction, the DNA was quantified spectrofluorometrically using Pico Green reagent (Invitrogen, Carlsbad, Calif.). The DNA was then visualized on an agarose gel to confirm values from the Pico Green analysis and to determine the DNA quality.

Example 2.2

DNA Digestion and Separation

For Southern blot molecular characterization of soybean Event DAS-68416-4, ten micrograms (10 µg) of genomic DNA was digested. Genomic DNA from the soybean Event DAS-68416-4 and non-transgenic soybean line Maverick was digested by adding approximately five units of selected restriction enzyme per µg of DNA and the corresponding reaction buffer to each DNA sample. Each sample was incubated at approximately 37° C. overnight. The restriction enzymes SpeI, KpnI, and PacI were used individually for the digests (New England Biolabs, Ipswich, Mass.). In addition, a positive hybridization control sample was prepared by combining plasmid DNA, pDAB4468, with genomic DNA from the non-transgenic soybean variety, Maverick. The plasmid DNA/genomic DNA cocktail was digested using the same procedures and restriction enzyme as the test samples. After the digestions were incubated overnight, NaCl was added to a final concentration of 0.1M and the digested DNA samples were precipitated with isopropanol. The precipitated DNA pellet was resuspended in 20 ul of 1× loading buffer (0.1% bromophenol blue, 100 mM EDTA, 50% glycerol, 10 mM Tris pH 7.5). The DNA samples and molecular size markers were then electrophoresed through 0.85% agarose gels with 0.4×TAE buffer (Fisher Scientific, Pittsburgh, Pa.) at 35 volts for approximately 18-22 hours to achieve fragment separation. The gels were stained with ethidium bromide (Invitrogen, Carlsbad, Calif.) and the DNA was visualized under ultraviolet (UV) light Example 2.3

Southern Transfer and Membrane Treatment

Southern blot analysis was performed as described by Severson et al. (1997). Following electrophoretic separation and visualization of the DNA fragments under UV light, the gels were submerged in a denaturing solution (150 mM NaOH, 3 mM EDTA) for approximately 20 minutes and then transferred to a neutralizing solution (150 mM NaPO4, pH 7.8) for at least 20 minutes. Southern transfer onto nylon membranes (Roche Diagnostics, Indianapolis, Ind.) was performed overnight using a wicking system with transfer buffer (25 mM Sodium Pyrophosphate, pH 10). After transfer, the DNA was bound to the membrane by baking the membrane at 65° C. for about 2 hours. This process resulted in Southern blot membranes ready for hybridization.

Example 2.4

DNA Probe Labeling and Hybridization

The DNA fragments bound to the nylon membrane were detected using a labeled probe.

The probe used for this experiment was generated by PCR amplification using primers to a specific nucleotide region of plasmid pDAB4468. The amplified PCR fragment was isolated and purified from an agarose gel and used as a template for a hybridization probe. The Southern blot hybridization probe was labeled with $\alpha^{32}$P-specific nucleotide by random priming using the GE Healthcare READY-TO-GO™ DNA Labeling Beads (GE Healthcare, Piscataway, N.J.) following the manufacturer's instruction, and purified by PROBEQUANT™ G-50 micro-columns (Amersham/Pharmacia, Piscataway, N.J., USA). A table describing the probe used for this experiment is described in Table 2. Pre-hybridization was carried out at 65° C. for 4 hr using hybridization buffer (Sigma-Aldrich, St. Louis, Mo.). The pre-hybridization solution was then decanted and replaced with a hybridization solution containing a desired amount of specific probe pre-denatured by boiling in water for 5 minutes. The hybridization/probe mixture was incubated with the nylon membrane overnight at 65° C.

After hybridization, the membrane was washed at 65° C. in washing buffer (10 mM sodium phosphate, 2.5 mM sodium pyrophosphate, 0.5 mM EDTA, 0.1% SDS, adjust pH to 7.8 with phosphoric acid.) for 20 minutes, three times. The washed filters were exposed to Phosphorimager screen for autoradiography and images were scanned. The number and sizes of detected bands were documented for the probe. In addition, a molecular weight marker was used to determine hybridizing fragment size on the Southern blots.

TABLE 2

Location and Length of Probes used in Southern Analysis.

| Probe Name | Genetic Element | Position on pDAB4468 (bp) | Length (bp) |
|---|---|---|---|
| aad-12 | aad-12 | 10118-10768 | 671 |

Example 2.5

Southern Blot Results

Expected and observed fragment sizes with a particular digest and probe, based on the known restriction enzyme sites of the aad-12 PTU, are given in Table 3. Expected fragment sizes are based on the plasmid map of pDAB4468 (FIG. 1) and observed fragment sizes are approximated from these analyses and are based on the indicated sizes of the $\alpha^{32}$P-labeled DNA Molecular Weight Marker II fragments.

Two types of fragments were identified from these digests and hybridizations: internal fragments where known enzyme sites flank the probe region and are completely contained within the insertion region of the aad-12 PTU, and border fragments where a known enzyme site is located at one end of the probe region and a second site is expected in the soybean genome. Border fragment sizes vary by event because, in most cases, DNA fragment integration sites are unique for each event. The border fragments provide a means to locate a restriction enzyme site relative to the integrated DNA and to evaluate the number of DNA insertions. Southern blot analyses completed on three generations of soybean containing Event DAS-68416-4 produced data which suggested that a low copy, intact aad-12 PTU from plasmid pDAB4468 was inserted into the soybean genome of soybean Event DAS-68416-4.

TABLE 3

Predicted and Observed Hybridizing Fragments in Southern Blot Analysis.

| DNA Probe | Restriction Enzymes | | Expected Fragment Sizes (bp)[1] | Observed Fragment Size (bp)[2] |
|---|---|---|---|---|
| aad-12 | SpeI | pDAB4468 | 12,154 | 12,154 |
| | | Maverick | None | none |
| | | DAS-68416-4 | >5,436 (border) | ~12,000 |
| | KpnI | pDAB4468 | 12,154 | 12,154 |
| | | Maverick | None | none |
| | | DAS-68416-4 | >5,383 (border) | ~16,000 |
| | PacI | pDAB4468 | 2,904 | 2,904 |
| | | Maverick | None | none |
| | | DAS-68416-4 | 2,904 | 2,904 |

The restriction enzymes SpeI and KpnI contain unique restriction sites in plasmid pDAB4468. Subsequently, these enzymes were selected to characterize the aad-12 gene insert in soybean Event DAS-68416-4. Border fragments of >5,436 bp or >5,383 bp were predicted to hybridize with the aad-12 gene probe following SpeI and KpnI digest respectively (Table 3). Single aad-12 hybridization bands of ~12,000 bp and ~16,000 bp were observed when SpeI and KpnI were used, respectively. The hybridization of the probe to bands of this size suggests the presence of a single site of insertion for the aad-12 gene in the soybean genome of soybean Event DAS-68416-4. Restriction enzyme PacI was selected to release a fragment of 2,904 bp which contains the aad-12 plant transcription unit (PTU, promoter/gene/terminator) (Table 3). The predicted 2,904 bp fragment was observed with the aad-12 gene probe following PacI digestion. Results obtained with all three enzyme digestion of the DAS-68416-4 sample followed by aad-12 gene probe hybridization indicated that a single copy of an intact aad-12 PTU from plasmid pDAB4468 was inserted into the soybean genome of soybean Event DAS-68416-4.

Example 2.6

Absence of Backbone Sequences

To monitor the presence or absence of the spectinomycin resistance gene in soybean Event DAS-68416-4, a multiplex PCR assay was performed. The experiment was designed for detection of five different regions of the spectinomycin resistance gene coding sequence and a 407 bp region in the endogenous soybean lectin gene (GenBank ID No: K00821 M30884) sequence as an internal control. In addition, the following controls were included: (i) a positive control with plasmid DNA carrying the spectinomycin resistance gene added to non-transformed soybean genomic DNA; (ii) a negative control using genomic DNA from non-transformed soybean, Maverick; and (iii) a blank with no genomic DNA.

Genomic DNA from soybean was isolated using the CTAB method and quantified using Pico Green. The DNA concentration of each sample was normalized to 100 ng/ul. PCR reactions were performed using primer sequences specific for the spectinomycin resistance gene coding sequence and the lectin gene sequence. The reactions were analyzed by loading 20 µl of PCR product per sample on a 2% E-gel.

The presence of multiple amplicons (bands of 100 bp, 150 bp, and 407 bp) on the E-gel would indicate that soybean Event DAS-68416-4 contained the spectinomycin resistance gene coding sequence (amplified bands of 100 bp and 150 bp are expected for spectinomycin resistance gene coding sequences). If only the 407 bp amplicon, corresponding to the internal control lectin gene sequence, is present this indicates that soybean Event DAS-68416-4 does not contain a spectinomycin resistance coding sequence.

DNA samples from the soybean Event DAS-68416-4 did not amplify fragments of 100 bp or 150 bp. Only the 407 bp fragment was amplified. However, the 100 bp, 150 bp, and 407 bp amplification fragments were present in the positive control where plasmid DNA carrying the spectinomycin resistance gene was added to soybean genomic DNA. The negative control containing DNA from non-transformed soybean amplified a single 407 bp fragment. Finally, the reactions that did not contain any genomic DNA did not produce any amplification fragments. As such no spectinomycin resistance coding sequence was detected in soybean Event DAS-68416-4.

Example 3

Cloning and Characterization of DNA Sequence in the Insert and the Flanking Border Regions of Soybean Event DAS-68416-4

To characterize and describe the genomic insertion site, the sequence of the T-strand DNA insert and flanking genomic DNA border regions of soybean Event DAS-68416-4 were determined. In total, 10,212 bp of soybean Event DAS-68416-4 genomic sequence was confirmed, comprising 2,730 bp of 5' flanking border sequence, 1,091 bp of 3' flanking border sequence, and 6,391 bp of T-strand insert (SEQ ID NO:1). Sequence analysis verified that soybean Event DAS-68416-4 contains a single-copy of an intact transgene containing the MAR element, the aad-12 expression cassette, and the pat expression cassette with no sequence variation from the expected T-strand insert.

PCR amplification based on the soybean Event DAS-68416-4 insert and border sequences validated that the border regions were of soybean origin and that the junction regions could be used for event-specific identification of soybean Event DAS-68416-4. Analysis of the sequence spanning the junction regions, including the flanking border sequences, did not identify any novel open reading frames (ORF>=150 codons) resulting from the T-strand insertion. In addition, the T-strand insertion site was characterized by cloning a genomic fragment corresponding to the region of the identified flanking border sequences from the genome of non-transgenic soybean. Comparison of soybean Event DAS-68416-4 with the wild type genomic sequence revealed a 55 bp deletion from the original locus and a 9 bp insertion at the 3' integration junction of the event. Overall, the characterization of the insert and border sequence of soybean Event DAS-68416-4 indicated that a single, intact copy of the T-strand was present in the soybean genome.

Example 3.1

Genomic DNA Extraction and Quantification

Genomic DNA was extracted from lyophilized or freshly ground leaf tissues using a modified CTAB method. Following genomic DNA extraction, DNA samples were dissolved in 1× TE (10 mM Tris pH8.0, 1 mM EDTA) (Fluka, Sigma, St. Louis, Mo.) and quantified using the Pico Green method according to manufacturer's instructions (Molecular Probes, Eugene, Oreg.). For PCR analysis, DNA samples were diluted with molecular biology grade water (5 PRIME, Gaithersburg, Md.) to result in a concentration of 10-100 ng/µL.

Example 3.2

PCR Primers

Table 4 lists the primer sequences that were used to clone and confirm the DNA insert and the flanking border regions of soybean Event DAS-68416-4, with positions and descriptions marked in FIG. 2. All primers were synthesized by Integrated DNA Technologies, Inc. (Coralville, Iowa). Primers were dissolved in water (5 PRIME, Gaithersburg, Md.) to a concentration of 100 µM for the stock solution and diluted with water to a concentration of 10 µM for the working solution.

TABLE 4

Conditions for genome walking soybean Event DAS-68416-4 to amplify the flanking border regions

| Target Sequence | Primer Set | PCR Mixture | Pre-denature (° C./min) | Denature (° C./sec.) | Anneal (° C./sec.) | Extension (° C./min:sec) | Denature (° C./sec.) | Anneal (° C./sec.) | Extension (° C./min:sec) | Final Extension (° C./min) |
|---|---|---|---|---|---|---|---|---|---|---|
| 5' border | ES_LEnd03 (SEQ ID NO: 2)/ AP1 (SEQ ID NO: 3) | F | 95/3 | 95/30 | 68$^{-0.5/cycle}$→64/30 8 cycles | 68/10:00 | 95/30 | 64/30 22 cycles | 68/10:00 | 72/10 |

TABLE 4-continued

Conditions for genome walking soybean Event DAS-68416-4 to amplify the flanking border regions

| Target Sequence | Primer Set | PCR Mixture | Pre-denature (° C./min) | Denature (° C./sec.) | Anneal (° C./sec.) | Extension (° C./min:sec) | Denature (° C./sec.) | Anneal (° C./sec.) | Extension (° C./min:sec) | Final Extension (° C./min) |
|---|---|---|---|---|---|---|---|---|---|---|
| 5' border (nested) | ES_LEnd04 (SEQ ID NO: 4)/ AP2 (SEQ ID NO: 5) | F | 95/3 | 95/30 | $68^{-0.5/cycle} \rightarrow 64/30$ 8 cycles | 68/10:00 | 95/30 | 64/30 24 cycles | 68/10:00 | 72/10 |
| 3' border | ES_PATEnd03 (SEQ ID NO: 6)/ AP1 (SEQ ID NO: 1) | F | 95/3 | 95/30 | $68^{-0.5/cycle} \rightarrow 64/30$ 8 cycles | 68/10:00 | 95/30 | 64/30 22 cycles | 68/10:00 | 72/10 |
| 3'border (nested) | ES_PATEnd04 (SEQ ID NO: 7)/ AP2 (SEQ ID NO: 5) | F | 95/3 | 95/30 | $68^{-0.5/cycle} \rightarrow 64/30$ 8 cycles | 68/10:00 | 95/30 | 64/30 24 cycles | 68/10:00 | 72/10 |

TABLE 5

Conditions for standard PCR amplification of the border regions and event-specific sequences in soybean Event DAS-68416-4

| Target Sequene | Primer Set | PCR Mixture | Pre-denature (° C./min) | Denature (° C./sec.) | Anneal (° C./sec.) | Extension (° C./min:sec) | Final Extension (° C./min) |
|---|---|---|---|---|---|---|---|
| 5' border | 16LEndG01 (SEQ ID NO: 8)/ AIILEnd05 (SEQ ID NO: 9) | B | 95/3 | 95/30 | 60/30 35 cycles | 68/5:00 | 72/10 |
| 5' border | 16LEndG02 (SEQ ID NO: 10)/ AIILEnd06 (SEQ ID NO: 11) | B | 95/3 | 95/30 | 60/30 35 cycles | 68/5:00 | 72/10 |
| specific sequence in 5' end insert junction | Soy416-F (SEQ ID NO: 12)/ Soy416-R (SEQ ID NO: 13) | C | 95/15 | 94/30 | 60/30 35 cycles | 72/1:00 | 72/10 |
| 3'border | 16PATG01 (SEQ ID NO: 14)/ PATEnd06 (SEQ ID NO: 15) | B | 95/3 | 95/30 | 60/30 35 cycles | 68/5:00 | 72/10 |
| 3' border | 16PATG02 (SEQ ID NO: 16)/ PATEnd06 (SEQ ID NO: 15) | B | 95/3 | 95/30 | 60/30 35 cycles | 68/5:00 | 72/10 |
| Across the insert locus | 16LEndG03 (SEQ ID NO: 17)/ 16PATG03 (SEQ ID NO: 18) | A | 95/3 | 95/30 | 60/30 35 cycles | 68/5:00 | 72/10 |
| Across the insert locus | 16LEndG04 (SEQ ID NO: 19)/ 16PATG04 (SEQ ID NO: 20) | A | 95/3 | 95/30 | 60/30 35 cycles | 68/5:00 | 72/10 |

TABLE 6

Primer description for amplicons 1-4 for T-strand insert

| Target Sequence | Primer Set | PCR Mixture | Pre-denature (° C./min) | Denature (° C./sec.) | Anneal (° C./sec.) | Extension (° C./min:sec) | Final Extension (° C./min) |
|---|---|---|---|---|---|---|---|
| 5' Genomic DNA/DNA insert (978bp) | 416-5-1 (SEQ ID NO: 21)/ 4468-1R (SEQ ID NO: 22) | D | 95/2 | 94/60 | 55/60 35 cycles | 72/2:00 | 72/15 |
| DNA insert (2414bp) | 4468-1 (SEQ ID NO: 23)/ 4468-2R (SEQ ID NO: 24) | E | 95/2 | 94/60 | 55/60 35 cycles | 72/2:00 | 72/15 |
| DNA insert (1834bp) | 4468-2 (SEQ ID NO: 25)/ 4468-3R (SEQ ID NO: 26) | E | 95/2 | 94/60 | 55/60 35 cycles | 72/2:00 | 72/15 |
| DNA insert/ 3' Genomic DNA (1705bp) | 4468-3 (SEQ ID NO: 27)/ 416-3-1R (SEQ ID NO: 28) | E | 95/2 | 94/60 | 55/60 35 cycles | 72/2:00 | 72/15 |
| DNA Insertion Site (~470bp) | 416-5-1 (SEQ ID NO: 21)/ 416-3-1R (SEQ ID NO: 28) | E | 95/2 | 94/60 | 55/60 35 cycles | 72/1:30 | 72/15 |

TABLE 7

PCR mixture for standard PCR amplification of the border regions and event specific sequences in soybean Event DAS-68416-4.

| PCR Mixture A | | PCR Mixture B | | PCR Mixture C | |
|---|---|---|---|---|---|
| Reagent | 1 × reaction (μL) | Reagent | 1 × reaction (μL) | PCR Mix | 1 × reaction (μL) |
| H20 | 29 | H20 | 30.5 | H2O | 31 |
| 10X PCR buffer II (Mg-plus) | 5 | 10X PCR buffer II (Mg-plus) | 5 | 10 × QIA buffer | 5 |
| MgCl2[25 mM] | 1.5 | MgCl2[25 mM] | 0 | MgCl2 | 1.5 |
| dNTP[2.5 mM] | 8 | dNTP[2.5 mM] | 8 | dNTP[2.5 mM] | 8 |
| primer1 (10 μM) | 1 | primer1 (10 μM) | 1 | primer1 (10 μM) | 1 |
| primer2 (10 μM) | 1 | primer2 (10 μM) | 1 | primer2 (10 μM) | 1 |
| DNA[10 ng/uL] | 4 | DNA[10 ng/uL] | 4 | DNA[10 ng/uL] | 4 |
| LA Taq (5 U/ul) | 0.5 | LA Taq (5 U/ul) | 0.5 | QIA Hstaq(5 U/ul) | 0.5 |
| rxn vol: | 50 | rxn vol: | 50 | rxn vol: | 50 |

| PCR Mixture D | | PCR Mixture E | | PCR Mixture F | |
|---|---|---|---|---|---|
| Reagent | 1 × reaction (μL) | PCR Mix | 1 × reaction (μL) | Reagent | 1 × reaction (μL) |
| H20 | 40.25 | H2O | 22 | H20 | 32 |
| 10X PCR buffer II (Mg-plus) | 5 | Easy-A 2x Master Mix | 25 | 10X PCR buffer II (Mg-plus) | 5 |
| MgCl2 | 0 | MgCl2 | 0 | MgCl2[25 mM] | 1.5 |
| dNTP[10 mM] | 1 | dNTP[2.5 mM] | 0 | dNTP[2.5 mM] | 8 |
| primer1 (100 μM) | 1 | primer1 (100 μM) | 1 | primer1 (10 μM) | 1 |
| primer2 (100 μM) | 1 | primer2 (100 μM) | 1 | primer2 (10 μM) | 1 |
| DNA[100 ng/uL] | 1 | DNA[10 ng/uL] | 1 | DNA Template | 1 |
| Expand High Fidelity Taq (5 U/ul) | 0.75 | rxn vol: | 50 | LA Taq (5 U/ul) | 0.5 |
| rxn vol: | 50 | | | rxn vol: | 50 |

Example 3.3

Genome Walking

The GENOMEWALKER™ Universal Kit (Clontech Laboratories, Inc., Mountain View, Calif.) was used to clone the 5' and 3' flanking border regions of the pDAB4468 T-strand insert for soybean Event DAS-68416-4 following manufacturer's instructions. Approximately 2 µg of genomic DNA from soybean Event DAS-68416-4 was digested overnight with EcoRV and PvuII (FIG. 2). DNA digests were purified using the DNA CLEAN & CONCENTRATOR™-25 (ZYMO Research, Orange, Calif.) followed by ligation to GENOMEWALKER™ adaptors to construct GENOMEWALKER™ libraries. Each GENOMEWALKER™ library was used as a DNA template for primary PCR amplification with adaptor primer AP1 (provided in the kit) and a construct-specific primer ES_LEnd03 or ES_PATEnd03 (Table 4). One microliter (1 µL) of 1:25 dilution of primary PCR reaction was then used as template for the secondary PCR amplification with the nested adaptor primer AP2 provided in the kit and a nested construct-specific primer ES_LEnd04 or ES_PATEnd04 (Tables 4, 7, and FIG. 2).

Example 3.4

Conventional PCR

Standard PCR was used to clone and confirm the insert and border sequence of soybean Event DAS-68416-4. TaKaRa LA TAQ™ (Takara Bio Inc, Shiga, Japan), HOT-STARTAQ™ DNA Polymerase (Qiagen, Valencia, Calif.), HIGH FIDELITY™ PCR Kit (Roche Diagnostics, Inc), or the EASY-A™ High Fidelity Polymerase Kit (Stratagene, LaJolla, Calif.) were used for conventional PCR amplification according to the manufacturer's recommended procedures. Specific PCR conditions and amplicon descriptions are listed in Tables 5, 6, and 7.

Example 3.5

PCR Product Detection, Purification, Sub-Cloning of PCR Products, and Sequencing PCR products were inspected by electrophoresis using a 1.2% or 2% E-GEL® (Invitrogen, Carlsbad, Calif.) according to product instruction. Fragment size was estimated by comparison with the DNA markers. If necessary, PCR fragments were purified by excising the fragments from a 1% agarose gel in 1×TBE (89 mM Tris-Borate, 2 mM EDTA, pH 8.3) stained with ethidium bromide using the QIAquick Gel Extraction Kit (Qiagen, Valencia, Calif.).

PCR fragments were sub-cloned into the PCR®4-TOPO® vector using the TOPO TA CLONING® KIT for Sequencing (Invitrogen, Carlsbad, Calif.) according to the product instructions. Specifically, two to five microliters of the TOPO® cloning reaction was transformed into the One Shot chemically competent TOP10 cells following manufacturer's instruction. Cloned fragments were verified by minipreparation of the plasmid DNA (QIAprep Spin Miniprep Kit, Qiagen, CA) followed by restriction digestion with EcoRI or by direct colony PCR using T3 and T7 primers. Plasmid DNA or glycerol stock of selected colonies were then outsourced for sequencing.

After sub-cloning, putative target PCR products were sequenced initially to confirm that the expected DNA fragments had been cloned. The colonies containing the expected DNA fragments were selected to complete double-strand full length sequencing by primer walking All sequencing was performed by Cogenics (Houston, Tex.).

Final assembly of insert and border sequences was completed using SEQUENCHER® software (Gene Codes Corporation, Ann Arbor, Mich.). Annotation of the insert and its flanking border sequences of soybean Event DAS-68416-4 was performed using Vector NTI (Version 10 and 11, Invitrogen, Carlsbad, Calif.).

Homology searching was performed using the BLAST program against the GenBank non-redundant nucleotide database. Open reading frame (ORF) analysis using Vector NTI (Version 11, Invitrogen) was performed to identify ORFs (>=150 codons) in the full insert and flanking border sequences of soybean Event DAS-68416-4, and the original locus of the wildtype Maverick soybean line.

Example 3.6

5' End Border Sequence

A DNA fragment was amplified from each soybean Event DAS-68416-4 GENOMEWALKER™ library using the specific nested primer set for the 5' end of transgene. A ~1.8 kb fragment from the EcoRV GENOMEWALKER™ library and a ~3 kb fragment from the PvuII GENOMEWALKER™ library were observed. These fragments were cloned into PCR® 4-TOPO® vector. Five colonies for each library were randomly picked for end sequencing to generate nucleotide sequence data. The colonies containing the sequences of both PCR primers were selected to obtain the full sequences by primer walking Sequence analysis revealed that the clone amplified from soybean Event DAS-68416-4 EcoRV GENOMEWALKER™ library contained a 1,744 bp DNA fragment and the clone amplified from soybean Event DAS-68416-4 PvuII GENOMEWALKER™ library contained a 3,047 bp DNA fragment. Sequence analysis revealed that the DNA fragment obtained from the EcoRV GENOMEWALKER™ library overlapped with the DNA fragment obtained from the PvuII GENOMEWALKER™ library clone at regions between primer ES_LEnd04 and the EcoRV site. These DNA fragments all contained the 5' end junction of T-strand border B in the transgene, indicating that they were amplified from the same region of the 5' end transgene insert and its flanking border in soybean Event DAS-68416-4. The resultant 2,730 bp soybean genomic sequence was found to have no significant homologies with the sequences in GenBank.

Example 3.7

3' End Border Sequence

A DNA fragment with size of about 1.3 kb was amplified from soybean Event DAS-68416-4 EcoRV GENOMEWALKER™ library using the specific nested primer set for the 3' end of the transgene. The DNA fragment was then cloned into a PCR®4-TOPO® vector. Five colonies were randomly picked for end sequencing. All five clones contained the sequences of both Primer AP2 and Primer ES_PATEnd04. Complete sequencing of these clones resulted in a 1,359 bp consensus DNA fragment. Sequence analysis disclosed that the 1,359 bp fragment comprised of a 268 bp fragment from the 3' end region of T-strand Border A and a 1,091 bp fragment from soybean genomic DNA. BLAST search did not identify any significant homologies between this 1,091 bp soybean DNA sequence and the sequences in GenBank.

Example 3.8

DNA Insert and Junction Sequence

The DNA insert and flanking border regions were cloned from soybean Event DAS-68416-4 using PCR based methods as previously described. The 5' and 3' flanking border sequences and the expected transgene sequence were used to design the PCR primers listed in Table 6. In total, four overlapping DNA fragments (Amplicon 1 of 978 bp, Amplicon 2 of 2,414 bp, Amplicon 3 of 1,834 bp, and Amplicon 4 of 1,705 bp) were cloned and sequenced (FIG. 3). The whole insert and flanking border sequences were assembled based on overlapping sequence among the four fragments. Analysis of the final assembled sequence confirmed the presence of a 6,391 bp fragment derived from the transgene of pDAB4468, and no base changes of the inserted DNA sequence were encountered when compared to the expected sequences from plasmid pDAB4468.

Example 3.9

Confirmation of Soybean Genomic Sequences

To confirm the insertion site of soybean Event DAS-68416-4 transgene in the soybean genome, PCR was carried out with different pairs of primers (FIG. 4 and Table 5). Genomic DNA from soybean Event DAS-68416-4 and other transgenic or non-transgenic soybean lines was used as templates. Thus, to confirm if the obtained 5' end border sequences are correct, two aad-12 specific primers, for example AIIILEnd05 and AIIILEnd06, and two primers designed according to the 5' end border sequence, designated 16LEndG01 and 16LEndG02, were used for amplifying the DNA segment that spans the aad-12 gene to 5' end border sequence. Similarly, for confirmation of the cloned 3' end border sequence, a pat specific primer, for example PAT-End06, and two primers designed according to the 3' end border sequence, designated 16PATG01 and 16PATG02, were used for amplifying DNA segments that span the pat gene to 3' end border sequence. DNA fragments with predicted sizes were amplified only from the genomic DNA of soybean Event DAS-68416-4 with each primer pair, one primer located on the flanking border of soybean Event DAS-68416-4 and one transgene specific primer, but not from DNA samples from other transgenic soybean lines or non-transgenic control. The results indicate that the cloned 5' and 3' border sequences are the flanking border sequences of the T-strand insert in soybean Event DAS-68416-4.

To further confirm the DNA insertion in the soybean genome, a PCR amplification spanning the two soybean sequences was completed. Two primers designed according to the 5' end border sequence, 16LEndG03 and 16LEndG04, and two primers for the 3' end border sequence, 16PATG03 and 16PATG04, were used to amplify DNA segments that contain the entire transgene, the 5' end border sequence, and the 3' border sequence. As expected, PCR amplification with the primer pair of 16LEndG03 and 16PATG03 amplified an approximately 9 kb DNA fragment from the genomic DNA of soybean Event DAS-68416-4 and a 2.7 kb DNA fragment from the non-transgenic soybean controls and other soybean transgenic lines. Similarly, PCR reactions completed with the primer pair of 16LEndG04 and 16PATG04 produced an approximately 9 kb DNA fragment from the sample of soybean Event DAS-68416-4 and a 2.8 kb DNA fragment from all the other soybean control lines, correspondingly. It was noted that a faint band with size of about 6 kb was visible in all the soybean samples except soybean Event DAS-68416-4 when both primer pairs were used for PCR, suggesting that this faint band resulted from nonspecific amplification in soybean genome with this pair of primers.

Example 3.10

Confirmation of Soybean Genomic Sequences

The 2.7 kb and 2.8 kb amplified DNA fragments, using the primer pair of 16LEndG03 and 16PATG03 or the primer pair of 16LEndG04 and 16PATG04, from non-transgenic soybean line Maverick were cloned and sequenced. Their sequences were matched with each other and aligned with the cloned 5' and 3' border sequences from soybean Event DAS-68416-4. This demonstrated that the cloned DNA sequence contained the locus where the T-strand of pDAB4468 was integrated into soybean Event DAS-68416-4. Alignment analysis also revealed a 55 bp deletion from the original locus and a 9 bp insertion at 3' integration junction (FIG. 5). No open reading frames (>/=450 bp, 150 aa) were identified in the soybean genomic region of the original locus that was cloned.

Example 4

Genomic Characterization Via Flanking SNP Markers of Soybean Event DAS-68416-4

To characterize and describe the genomic insertion site, marker sequences located in proximity to the insert were determined. A panel of polymorphic Single Nucleotide Polymorphism (SNP) markers were used to identify and map the transgene location. Soybean Event DAS-68416-42 is located at 119.6 cM on chromosome 4. This location is between the two flanking SNP markers BARC-044607-08736 and BARC-019093-03299. More specifically, the location of the transgene was mapped 1.3 cM (480 kb) away from SNP marker BARC-019093-03299.

Example 4.1

BLAST with Flanking Border Region Sequences

The flanking border region sequences for soybean Event DAS-68416-4 (SEQ ID NO:1) were used to BLAST the soybean whole genome sequence. The BLAST results showed that both border sequences of soybean Event DAS-68416-4 were located on chromosome 4 (Gm04) which is linkage group C1.

Example 4.2

SNP Mapping and BLAST Results

Based on results from BLAST with border sequences and mapping, the event was assigned to chromosome 4. As such, ten SNP markers were selected from the soybean genetic linkage maps. The SNP sequences were selected from SNP markers developed by Dr. Cregan, the Beltsville Agricultural Research Center, and USDA. These SNP markers are associated with linkage group C1 which corresponds to chromosome 4. The SNP sequences were used to BLAST the soybean whole genome sequence to determine the physical positions of the T-strand insert for soybean Event DAS-68416-4.

Example 4.3

SNP Marker Results

Soybean Event DAS-68416-4 is mapped at 119.6 cM on chromosome 4. The two flanking SNP markers are BARC-044607-08736 and BARC-019093-03299. The transgene is 1.3 cM (480 kb) away from SNP marker BARC-019093-03299, approximately 119.6 cM between SNP markers BARC-044607-08736 and BARC-019093-03299.

Example 5

Characterization of AAD-12 Protein in Soybean Event DAS-68416-4

The biochemical properties of the recombinant AAD-12 protein derived from the transgenic soybean Event DAS-68416-4 were characterized. Quantitative enzyme-linked immunosorbent assay (ELISA), sodium dodecyl sulfate polyacrylamide gel electrophoresis (SDS-PAGE, stained with Coomassie blue and glycoprotein detection methods), and Western blot methods were used to characterize the biochemical properties of the protein and confirm expression of AAD-12 protein.

Example 5.1

Expression of the AAD-12 Protein in Plant Tissues

Levels of AAD-12 protein were determined in soybean Event DAS-68416-4. The soluble, extractable AAD-12 protein was measured using a quantitative enzyme-linked immunosorbent assay (ELISA) method in the soybean leaf.

Samples of soybean tissues were isolated from the test plants and prepared for expression analysis. The AAD-12 protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an AAD-12 ELISA kit in a sandwich format. The kit was used following the manufacture's suggested protocol.

Detection analysis was performed to investigate the expression stability and inheritability both vertically (between generations) and horizontally (between lineages) in soybean Event DAS-68416-4. At the T5 generation soybean Event DAS-68416-4 expression was stable (not segregating) and consistent across all lineages (FIG. 6).

Field expression level studies at various plant stages were performed on soybean Event DAS-68416-4 at pre V3, post V3, pre R2, and post R2. Expression values were similar for all the sprayed treatments as well as for the plots sprayed and unsprayed with 2,4-D herbicide. A 2 X spray rate (2,240 gm ae/ha of 2,4-D) was applied and no injury was observed on the plants at any point of the study. Average expression across all lineages in pre v3 plant stage was 300 ug/cm². After spraying 2,4-D the expression remained stable averaging 400 ug/cm² across lineages. By the time the soybeans reached pre R2 the average expression had dropped slightly to an average of 200 ug/cm². After spraying 2,4-D the expression post R2 had returned to the previous average of 400 ug/cm². See FIG. 6.

Example 5.2

Expression of the AAD-12 Protein in Plant Tissues

An additional field expression study was conducted at six locations in U.S. and Canada during 2008. Four treatments of the soybean Event DAS-68416-4 (unsprayed, sprayed with 2,4-D, sprayed with glufosinate, or sprayed with both 2,4-D and glufosinate) were tested. Plant tissues sampled included leaf, grain, root, and forage. Leaf tissues were collected at V5 and V10 stage, and root and forage were collected at the R3 stage of development. The grain was collected at the R8 stage of development (Gaska, 2006). The soluble, extractable AAD-12 protein was measured using a validated enzyme-linked immunosorbent assay (ELISA) method as previously described in Example 5.1. AAD-12 protein levels for all tissue types were calculated on ng/mg dry weight basis.

A summary of the AAD-12 protein concentrations (averaged across sites) in the various soybean matrices is shown in Table 8. Average expression values ranged from 15.5 ng/mg dry weight in R3 stage root to 66.1 ng/mg in V5 stage leaf tissue. Expression values were similar for all sprayed treatments as well as for the plots sprayed and unsprayed with 2,4-D and glufosinate herbicides. No AAD-12 protein was detected in the control tissues across the six locations.

TABLE 8

Summary of AAD-12 protein levels in tissues collected from soybean Event DAS-68416-4 produced in the U.S. and Canada during 2008.

| Soybean Tissue | Treatment | AAD-12 ng/mg Tissue Dry Weight | | |
|---|---|---|---|---|
| | | Mean | Std. Dev. | Range |
| V5 Leaf | DAS-68416-4 Unsprayed | 51.4 | 25.2 | 26.4-97.7 |
| | DAS-68416-4 + Glufosinate | 50.6 | 23.7 | 28.0-94.0 |
| | DAS-68416-4 + 2,4-D | 51.7 | 25.4 | 27.2-101 |
| | DAS-68416-4 + Glufosinate and 2,4-D | 66.1 | 37.8 | 25.1-165 |
| V10 Leaf | DAS-68416-4 Unsprayed | 54.0 | 20.9 | 29.8-90.9 |
| | DAS-68416-4 + Glufosinate | 56.1 | 22.0 | 25.1-92.0 |
| | DAS-68416-4 + 2,4-D | 55.2 | 20.6 | 30.8-91.8 |
| | DAS-68416-4 + Glufosinate and 2,4-D | 57.1 | 23.0 | 32.0-95.2 |
| Root | DAS-68416-4 Unsprayed | 17.1 | 5.68 | 8.80-27.6 |
| | DAS-68416-4 + Glufosinate | 15.5 | 4.58 | 6.30-23.1 |
| | DAS-68416-4 + 2,4-D | 16.0 | 6.64 | 3.16-27.9 |
| | DAS-68416-4 + Glufosinate and 2,4-D | 16.7 | 6.81 | 1.84-26.5 |
| Forage | DAS-68416-4 Unsprayed | 41.1 | 25.7 | 5.70-91.2 |
| | DAS-68416-4 + Glufosinate | 39.4 | 24.5 | 5.49-88.0 |
| | DAS-68416-4 + 2,4-D | 40.6 | 25.6 | 5.02-88.0 |
| | DAS-68416-4 + Glufosinate and 2,4-D | 39.7 | 22.4 | 4.96-69.6 |
| Grain | DAS-68416-4 Unsprayed | 16.5 | 3.55 | 9.40-21.9 |
| | DAS-68416-4 + Glufosinate | 16.9 | 3.15 | 11.9-22.7 |
| | DAS-68416-4 + 2,4-D | 16.5 | 3.78 | 9.71-22.0 |
| | DAS-68416-4 + Glufosinate and 2,4-D | 16.2 | 3.62 | 9.91-23.4 |

Example 5.3

SDS PAGE and Western Blot Analysis of the AAD-12 Protein

The AAD-12 protein was extracted from lyophilized leaf tissue of soybean Event DAS-68416-4 in a PBST (Phosphate Buffered Saline with 0.05% Tween 20, pH 7.4) based buffer with added stabilizers, and the soluble proteins were collected by centrifugation. The supernatant was filtered and the soluble proteins were allowed to bind to Phenyl Sepharose (PS) beads (GE Healthcare, Piscataway, N.J.). After an hour of incubation, the PS beads were washed with PBST and the bound proteins were eluted with Milli-Q water. Sodium chloride was added to increase the conductivity and the PS purified proteins were loaded onto an anti-AAD-12 immunoaffinity column which had been conjugated with an AAD-12 specific polyclonal antibody. The non-bound proteins were collected from the column and the column was washed extensively with pre-chilled PBS (phosphate buffered saline, pH 7.4). The bound proteins were eluted from the column with a 3.5 M NaSCN, 50 mM Tris, pH 8.0 buffer and examined by SDS-PAGE and western blotting. The same protocol was used to isolate protein from leaf tissue of the control soybean line Maverick. Maverick does not contain the aad-12 gene but has a genetic background representative of the soybean event DAS-68416-4 plants.

Lyophilized leaf tissue from soybean Event DAS-68416-4 and Maverick were mixed with PBST buffer containing ~2.0% protease inhibitor cocktail (Sigma, St. Louis, Mo.) and the protein was extracted by grinding with ball bearings in a Geno-Grinder. The samples were centrifuged and the supernatants were mixed with Laemmli sample buffer, heated, and briefly centrifuged. The samples were loaded directly on to a Bio-Rad Criterion SDS-PAGE gel. The positive reference standard, microbe-derived AAD-12 protein, was also mixed with sample buffer and loaded on to the gel. Electrophoresis was conducted with Tris/glycine/SDS buffer (Bio-Rad, Hercules, Calif.). Following electrophoresis, the gel was cut in half, with one half stained with Pierce GelCode Blue protein stain and the other gel half was electro-blotted onto a nitrocellulose membrane. The nitrocellulose membrane was then probed with an AAD-12 specific polyclonal rabbit antibody. A chemiluminescent substrate was used to visualize the immunoreactive bands. In the microbe-derived AAD-12, the major protein band, as visualized on the Coomassie stained SDS-PAGE gel, was approximately 32 kDa. As expected, the corresponding plant-derived AAD-12 protein was identical in size to the microbe-derived protein. Predictably, the plant purified fractions contained a minor amount of non-immunoreactive impurities in addition to the AAD-12 protein. The co-purified proteins were likely retained on the column by weak interactions with the column matrix (Williams, et. al., 2006, Kennedy and Barnes, 1983 and Holroyde et al., 1976).

The microbe-derived AAD-12 and DAS-68416-4 plant tissue extract showed a positive signal of the expected size on the western blot using the anti-AAD-12 polyclonal antibody. In the AAD-12 western blot analysis, no immunoreactive proteins were observed in the control Maverick extract and no alternate size proteins (aggregates or degradation products) were seen in the samples from the transgenic plant. The monoclonal antibody did detect a small amount of the AAD-12 dimer in the microbe-derived protein. These results add to the evidence that the AAD-12 protein is expressed in soybean.

Example 6

Methylation Detection Analysis of Soybean Event DAS-68416-4 Via Southern Blot Introduced transgenes can undergo silencing after integration into the plant genome. Transgene expression can be inhibited at the transcriptional level and/or the post-transcriptional level. Transcriptional gene silencing has been reported to be associated with methylation of the transgene, its promoter and other relevant sequences (Stem et al, 1997). To detect methylation in specific sequences, one method utilizes methylation-sensitive restriction enzymes to digest DNA followed by Southern blot analysis of the DNA products. When specific restriction enzyme sites are methylated the enzymes will not cleave the DNA. The methylation of the restriction sites results in higher molecular weight DNA fragments which are detectable on Southern blots. The Southern-blot based methylation analysis was performed to determine methylation status of the T-strand insert for soybean Event DAS-68416-4. This assay was conducted using probes specific to aad-12 gene and its promoter and two methylation-sensitive restriction enzymes. Methylation of the aad-12 expression cassette was not detected.

6.1

Soybean Leaf Sample Collection and Genomic DNA (gDNA) Isolation

Genomic DNA was prepared from leaf of the individual plants of the soybean Event DAS-68416-4 and non-transgenic soybean line Maverick. Genomic DNA was isolated from lyophilized leaf samples using a traditional CTAB method. Following extraction, the DNA was quantified using Pico Green reagent (Invitrogen, Carlsbad, Calif.).

6.2

DNA Digestion and Separation

For molecular characterization of the DNA, ten micrograms (10 µg) of genomic DNA from the soybean Event DAS-68416-4 and non-transgenic soybean line Maverick were digested by adding approximately five units of selected restriction enzyme per µg of DNA and the corresponding reaction buffer to each DNA sample. Each sample was incubated at approximately 37° C. overnight. The restriction enzymes AciI and Hyp188III were used for the digests (New England Biolabs, Ipswich, Mass.). DNA from the non-transgenic soybean Maverick was digested using the same procedures and restriction enzymes as the test samples to serve as a negative control. The digested DNA samples were precipitated with isopropanol after adding NaCl to a final concentration of 0.1 M and resuspended in 20 ul of 1× loading buffer (0.1% bromophenolblue, 100 mM EDTA, 50% glycerol, 10 mM Tris pH 7.5). The DNA samples and molecular size markers were then electrophoresed through 0.85% agarose gels with 0.4×TAE buffer (Fisher Scientific, Pittsburgh, Pa.) at 35 volts for approximately 18-22 hours to achieve fragment separation. The gels were stained with ethidium bromide (Invitrogen, Carlsbad, Calif.) and the DNA was visualized under ultraviolet (UV) light.

6.3

Southern Transfer and Membrane Treatment

Southern blot analysis was performed as described by Severson et al., (1997). Briefly, following electrophoretic separation and visualization of the DNA fragments under UV light, the gels were exposed to a denaturing solution (150 mM NaOH, 3 mM EDTA) for approximately 20 minutes followed by neutralizing solution (150 mM NaPO4, pH 7.8) for at least 20 minutes. Southern transfer was performed overnight onto nylon membranes (Roche Diagnostics, Indianapolis, Ind.) using a wicking system with transfer buffer (25 mM Sodium Pyrophosphate, pH 10). After transfer the membranes were baked at 65° C. for about 2 hours. This process resulted in Southern blot membranes ready for hybridization.

6.4

DNA Probe Labeling and Hybridization

The DNA fragments bound to the nylon membrane were detected using a labeled probe. The probes were generated as PCR fragments amplified with specific primers from plasmid pDAB4468. These PCR amplified fragments were excised and purified from the agarose gel. The purified DNA fragments were used as templates for making hybridization probes. Hybridization probes were labeled with $\alpha^{32}P$-specific nucleotide by random priming using the GE Healthcare READY-TO-GO™ DNA Labeling Beads (GE Healthcare, Piscataway, N.J.) following the manufacturer's instruction, and purified by PROBEQUANT™ G-50 micro columns (Amersham/Pharmacia, Piscataway, N.J., USA). A list of probes used for the study is described in Table 9.

Prehybridization and hybridization were carried out at 65° C. for 4 hr and overnight, respectively, using hybridization buffer (Sigma, St. Louis, Mo.). After hybridization, the membrane was washed at 65° C. in washing buffer (10 mM sodium phosphate, 2.5 mM sodium pyrophosphate, 0.5 mM EDTA, 0.1% SDS, adjust pH to 7.8 with phosphoric acid.) for 20 min three times. The washed filters were exposed to phosphorimager screen for autoradiography and images were scanned.

TABLE 9

Location and Length of Probes used in Southern Analysis.

| Probe Name | Genetic Element | Position on pDAB4468 (bp) | Length (bp) |
| --- | --- | --- | --- |
| ProAU10-a | ubiquitin promoter (AtUbi10) | 10827-11905 | 1100 |
| ProAU10-b | ubiquitin promoter (AtUbi10) | 10942-12020 | 1100 |
| aad-12 | aad-12 | 10118-10768 | 671 |

6.5

Probe Stripping

DNA probes were stripped off the membrane blots after the Southern hybridization data were obtained, and the membrane blots could be reused for hybridization with a different DNA probe. Briefly, after exposure, membrane blots were washed in Regeneration Solution 1 (30 mM NaOH, 1 mM Na2EDTA) at room temperature for 10 minutes and in Regeneration Solution 2 (5 mM NaPO4, 1 mM Na2EDTA, 0.1% SDS) at 65° C. for 30 minutes. The membrane blots were then briefly washed in 2×SSC and were ready for hybridization with another DNA probe. The membrane blots were exposed to a Phosphorimager screen for autoradiography to ensure all the DNA probes were stripped of before proceeding to the next hybridization.

6.6

Southern Blot Results

Methylation-sensitive restriction enzymes AciI and Hyp188III were used in this study to determine the methylation status of aad-12 gene and its promoter AtUbi10. Expected fragment sizes with a particular digest and probe, based on the known restriction enzyme sites of the T-strand DNA of pDAB4468, are given in Table 10. Detection of higher molecular weight fragments on the Southern blot would indicate the methylation of cytosine in the recognition sequence of the AciI and Hyp188III restriction enzymes sites. As such, the methylation would result in the inability of the restriction enzymes to digest the genomic DNA.

Restriction enzymes AciI and Hyp188III were used to examine aad-12 gene methylation status. Hybridization bands with the expected size were observed using the aad-12 probe. This data suggests no methylation occurred in the recognition site of AciI and Hyp188III in soybean Event DAS-68416-4. Similarly, bands of the predicted molecular weight were detected in DNA samples of soybean Event DAS-68416-4 digested with Hyp188III using the AtUbi10 probe. This data indicates that the recognition site was not methylated in the aad-12 promoter sequence.

TABLE 10

Predicted and Observed Hybridizing Fragments in Southern Blot Analysis.

| DNA Probe | Restriction Enzymes | | Expected Fragment Sizes (bp)[1] | Observed Fragment Size (bp)[2] |
| --- | --- | --- | --- | --- |
| ProAU10 | Hyp188III | pDAB4468 | 495, 368, 279, 210, and 87 | ~200bp* |
| | | Maverick | none | none |
| | | DAS-68416-4 | 495, 368, 279, 210, and 87 | ~500 bp and ~300 bp |
| aad-12 | Aci I | pDAB4468 | 673, 597, 422, 138 | Too weak to see |
| | | Maverick | none | none |
| | | DAS-68416-4 | 673, 597, 422, 138 | ~700bp and ~600bp |
| | Hyp188III | pDAB4468 | 472, 211, 209 | Too weak to see |
| | | Maverick | none | none |
| | | DAS-68416-4 | 472, 211, 209 | ~500bp and ~200bp |

Example 7

Agronomic Data

Agronomic trials were conducted with soybean Event DAS-68416-4 as part of a 2008 composition study at 6 locations in the U.S. and Canada, and also in a separate study conducted in 2009 at 8 locations in the U.S. and Canada.

These studies compared Event DAS-68416-4 soybeans (with and without the application of 2,4-D and/or glufosinate herbicides) with its non-transgenic near-isogenic control (Maverick). The results across both studies showed the agronomic parameters were within the range obtained for conventional soybean lines.

Example 7.1

Generation of 2008 Agronomic Data

An agronomic study with Event DAS-68416-4 soybean and a non-transgenic control (var. Maverick) was conducted in 2008 at six sites located in Iowa, Illinois, Indiana, Nebraska and Ontario, Canada (2 sites). Agronomic determinants, including stand/population count, seedling/plant vigor, plant height, lodging, disease incidence, insect damage, and days to flowering were evaluated to investigate the equivalency of the soybean Event DAS-68416-4 (with and without herbicide treatments) as compared to the control line Maverick. This study is referred to as Experiment 1.

The test and control soybean seed were planted at a seeding rate of approximately 112 seeds per 25 ft row with a row spacing of approximately 30 inches (75 cm). At each site, three replicate plots of each treatment were established, with each plot consisting of 2-25 ft rows. Plots were arranged in a randomized complete block (RCB) design, with a unique randomization at each site. Each soybean plot was bordered by two rows of a non-transgenic soybean of similar maturity. The entire trial site was surrounded by a minimum of 10 ft of a non-transgenic soybean of similar relative maturity.

Herbicide treatments were applied with a spray volume of approximately 20 gallons per acre (187 L/ha). These applications were designed to replicate maximum label rate commercial practices. 2,4-D was applied as three broadcast over-the-top applications for a seasonal total of 3 lb ae/A. Individual applications of 1.0 lb ae A (1,120 g/ha) were made at pre-emergence and approximately V4 and R2 growth stages. Glufosinate was applied as two broadcast over-the-top applications for a seasonal total of 0.74 lb ai/A (828 g ai/ha). Individual applications of 0.33 lb ai/A and 0.41 lb ai/A (374 and 454 g ai/ha) were made at approximately V6 and R1 growth stages.

Analysis of variance was conducted across the field sites for the agronomic data using a mixed model (SAS Version 8; SAS Institute 1999). Entry was considered a fixed effect, and location, block within location, location-by-entry, and entry-by-block within location were designated as random effects. The significance of an overall treatment effect was estimated using an F-test. Paired contrasts were made between the control and unsprayed soybean Event DAS-68416-4 (unsprayed), soybean Event DAS-68416-4 sprayed with glufosinate (soybean Event DAS-68416-4+glufosinate), soybean Event DAS-68416-4 sprayed with 2,4-D (soybean Event DAS-68416-4+2,4-D) and soybean Event DAS-68416-4 sprayed with both glufosinate and 2,4-D (soybean Event DAS-68416-4+both) transgenic entries using t-tests. Adjusted P-values were also calculated using the False Discovery Rate (FDR) to control for multiplicity (Benjamini and Hochberg, 1995).

TABLE 11

Agronomic parameters evaluated in Experiment 1.

| Trait | Evaluation Timing | Description of Data | Scale |
|---|---|---|---|
| Early population | VC-V2 | Number of plants emerged in rows of each plot | Actual count per plot |
| Seedling vigor | VC-V2 | Visual estimate of average vigor of emerged plants per plot | 1-10 scaled based on growth of the non-transformed soybeans 10 = Growth equivalence to non-transformed 9 = Plant health is 90% as compared to non-transformed, etc. |
| Plant vigor/injury | After post-emergent herbicide applications | Injury from herbicide applications | 1-10 scale based on growth of the non-transformed soybeans 10 = Growth equivalence to non-transformed 9 = Plant health is 90% as compared to non-transformed, etc. |
| Plant height | Approximately R6 | Height from soil surface to the tip of the highest leaf when extended by hand | Height in cm (average of 10 plants per plot) |
| Lodging | Approximately R8 | Visual estimate of lodging severity | Visual estimate on 0-100% scale based on the number of plants lodged |
| Final population | Approximately R8 | The number of plants remaining in rows of each plot | Actual count per plot, including plants removed during previous sampling |
| Stand count | R2 | Number of plants in one meter section of row | — |
| Days to Flower | | Number of days from planting to when 50% of plants are at R1 | Days |

An analysis of the agronomic data collected from the control, soybean Event DAS-68416-4 unsprayed, soybean Event DAS-68416-4+2,4-D, soybean Event DAS-68416-4+glufosinate, and soybean Event DAS-68416-4+both herbicides was conducted. No statistically significant differences were observed for stand count, early population, seedling vigor, injury after application, lodging, final stand count or days to flowering (Table 12). For height, a significant paired t-test was observed between the control and the soybean Event DAS-68416-4+2,4-D spray. However, no significant overall treatment effect was observed, differences were very small between the soybean Event DAS-68416-4 treatment and the control, and differences were not shared among the different soybean Event DAS-68416-4 treatments. Based on these results, soybean Event DAS-68416-4 was agronomically equivalent to the near-isogenic non-transgenic control.

TABLE 12

Analysis of agronomic characteristics from Experiment 1.

| Analyte | Overall Treatment Effect (Pr > F)[a] | Control | Unsprayed (P-value,[b] Adj. P)[c] | Sprayed Glufosinate (P-value, Adj. P) | Sprayed 2,4-D (P-value, Adj. P) | Sprayed Both P-value, Adj. P) |
|---|---|---|---|---|---|---|
| Stand Count (no. of plants) | 0.774 | 170 | 172 (0.709, 0.824) | 175 (0.311, 0.575) | 173 (0.476, 0.672) | 175 (0.269, 0.575) |
| Early Population (% emergence)[d] | 0.714 | 76.7 | 77.4 (0.738, 0.824) | 79.1 (0.301, 0.575) | 79.0 (0.327, 0.575) | 79.4 (0.256, 0.575) |
| Seedling Vigor[e] | 0.547 | 9.72 | 9.39 (0.146, 0.575) | 9.50 (0.326, 0.575) | 9.44 (0.222, 0.575) | 9.39 (0.146, 0.575) |
| Vigor/Injury App. 2[e] | 0.511 | 10.0 | 9.86 (0.461, 0.671) | 9.89 (0.555, 0.718) | 9.83 (0.378, 0.611) | 9.67 (0.087, 0.575) |
| Vigor/Injury App. 3[e] | 0.462 | 10.0 | 10.0 (1.000, 1.000) | 9.89 (0.320, 0.575) | 9.83 (0.141, 0.575) | 9.89 (0.320, 0.575) |
| Vigor/Injury App. 5[e] | 0.431 | 9.94 | 9.89 (0.721, 0.824) | 9.78 (0.289, 0.575) | 9.67 (0.085, 0.575) | 9.78 (0.289, 0.575) |
| Height (cm) | 0.144 | 101 | 98.1 (0.145, 0.575) | 99.2 (0.390, 0.611) | 96.1 (0.020, 0.575) | 97.2 (0.062, 0.575) |
| Lodging (%) | 0.948 | 17.2 | 18.2 (0.885, 0.904) | 21.3 (0.551, 0.718) | 20.7 (0.606, 0.746) | 21.7 (0.511, 0.700) |
| Final Stand Count (no. of plants) | 0.268 | 156 | 154 (0.770, 0.840) | 161 (0.335, 0.575) | 155 (0.817, 0.853) | 163 (0.127, 0.575) |
| Flowering Days[f] | 0.452 | 49.0 | 49.5 (0.261, 0.575) | 49.4 (0.395, 0.611) | 48.7 (0.568, 0.718) | 49.2 (0.668, 0.801) |

[a]Overall treatment effect estimated using an F-test.
[b]Comparison of the sprayed and unsprayed treatments to the control using a t-test.
[c]P-values adjusted using a False Discovery Rate (FDR) procedure.
[d]0-100% scale; (Stand count divided by the no. of seeds planted) * 100.
[e]Visual estimate on 1-10 scale; 10 = growth equivalent to non-transformed plants.
[f]Visual estimate on 0-100% scale; 0% = no damage.
[f]The number of days from the time of planting until flowering.
Bolded P-values are significant (<0.05).

Example 7.2

Generation of 2009 Agronomic Data

An agronomic study with soybean Event DAS-68416-4 and a non-transgenic control (var. Maverick) was conducted in 2009 at 8 sites located in Arkansas, Iowa, Illinois, Indiana, Missouri, and Nebraska. Agronomic determinants, including stand/population count, seedling/plant vigor, plant height, disease incidence, insect damage, and days to flowering were evaluated to investigate the equivalency of the soybean Event DAS-68416-4 soybeans (with and without herbicide treatments) to the control (Table 13).

TABLE 13

Data collected in agronomic and yield trials, 2009.

| Characteristic | Evaluation Timing | Description | Units reported | Test* |
|---|---|---|---|---|
| Emergence | VC-V2 | Stand count in 1 meter section of row divided by number of seeds planted per meter | % | B |
| Seedling vigor | V1-V3 | General seedling vigor | 1 (low) to 10 (high) | B |
| Visual injury | Post V3 application | Visual injury 1 day post herbicide application at V3 stage | % | S |

TABLE 13-continued

Data collected in agronomic and yield trials, 2009.

| Characteristic | Evaluation Timing | Description | Units reported | Test* |
|---|---|---|---|---|
| Visual injury | Post V3 application | Visual injury 7 days post herbicide application at V3 stage | % | S |
| Visual injury | Post V3 application | Visual injury 14 days post herbicide application at V3 stage | % | S |
| Days to Flower | | Number of days from planting to when 50% of plants are at R1 | days | B |
| Stand count | R2 | Number of plants in one meter section of row | | B |
| Visual injury | Post R2 application | Visual injury 1 day post herbicide application at R2 stage | % | S |
| Visual injury | Post R2 application | Visual injury 7 days post herbicide application at R2 stage | % | S |
| Visual injury | Post R2 application | Visual injury 14 days post herbicide application at R2 stage | % | S |
| Disease incidence | ~R6 | Opportunistic note on any disease that occurred at a location | % | B |
| Insect damage | ~R6 | Opportunistic note on any insect damage that occurred at a location | % | B |
| Plant Height | R8 | Final height of plot at R8 | cm | B |
| Maturity | R8 | Number of days from planting to when 95% of plants in plot have reached their mature color | days | B |
| Lodging | R8 | Degree of lodging in a plot | 1 (none)-5 (flat) | B |
| Yield | R8 | Weight of seed produced by the plot | bu/acre | B |
| 100 seed weight | R8 | Weight of 100 random seeds from the harvested plot | g | B |

*B—Sprayed and Unsprayed tests, S—Sprayed tests only

A randomized-complete-block design was used for trials. Entries were soybean Event DAS-68416-4, a Maverick control line, and commercially available non-transgenic soybean lines. The test, control and reference soybean seed were planted at a seeding rate of approximately 112 seeds per row with row spacing of approximately 30 inches (75 cm). At each site, 4 replicate plots of each treatment were established, with each plot consisting of 2-25 ft rows. Each soybean plot was bordered by 2 rows of a non-transgenic soybean (Maverick). The entire trial site was surrounded by a minimum of 4 rows (or 10 ft) of non-transgenic soybean (Maverick). Appropriate insect, weed, and disease control practices were applied to produce an agronomically acceptable crop.

Herbicide treatments were applied to replicate maximum label rate commercial practices. Treatments consisted of a non-sprayed control and herbicide applications of 2,4-D, glufosinate, 2,4-D/glufosinate applied at the specified growth stages. For the 2,4-D applications, the herbicide was applied at a rate of 1.0 lb ae/A (1,120 g ae/ha) at the V4 and R2 growth stages. For the glufosinate treatments, applications were made to plants at the V4 and V6-R2 growth stages. For both applications, glufosinate was applied at a rate of 0.33 lb ai/A (374 g ai/ha) and 0.41 lb ai/A (454 g ai/ha) for the V4 and V6-R2 applications, respectively. Entries for both herbicide applications were soybean Event DAS-68416-4 and the controls including non-transgenic Maverick. Maverick plots were expected to die after herbicide application.

Analysis of variance was conducted across the field sites for the agronomic data using a mixed model (SAS Version 8; SAS Institute 1999). Entry was considered a fixed effect, and location, block within location, location-by-entry, and entry-by-block within location were designated as random effects. Analysis at individual locations was done in an analogous manner with entry as a fixed effect, and block and entry-by-block as random effects. Data were not rounded for statistical analysis. Significant differences were declared at the 95% confidence level, and the significance of an overall treatment effect was estimated using an F-test. Paired contrasts were made between unsprayed AAD-12 (unsprayed), AAD-12 sprayed with glufosinate (AAD-12+glufosinate), AAD-12 sprayed with 2,4-D (AAD-12+2,4-D) and AAD-12 sprayed with both glufosinate and 2,4-D (AAD-12+2,4-D+glufosinate) transgenic entries and the control entry using T-tests.

Due to the large number of contrasts made in this study, multiplicity was an issue. Multiplicity is an issue when a large number of comparisons are made in a single study to look for unexpected effects. Under these conditions, the probability of falsely declaring differences based on comparison-wise p-values is very high ($1-0.95^{number\ of\ comparisons}$). In this study there were four comparisons per analyte (16 analyzed observation types for agronomics), resulting in 64 comparisons for agronomics. Therefore, the probability of declaring one or more false differences based on unadjusted p-values was 99% for agronomics ($1-0.95^{64}$.)

An analysis of the agronomic data collected from the control, AAD-12 unsprayed, AAD-12+glufosinate, AAD-12+2,4-D, and AAD-12+2,4-D+glufosinate entries was conducted. For the across-site analysis (Table 14), no statistically significant differences were observed for seedling vigor, final population, plant vigor/injury (V4, R1), lodging, disease incidence, insect damage, days to flowering, days to maturity, number of pods, number of seeds, yield, and plant height. For stand count and early population, a significant paired t-test was observed between the control and the AAD-12+glufosinate entry, but was not accompanied by a significant overall treatment effect or FDR adjusted p-value. For plant vigor/injury (R2), significant paired t-tests and a significant overall treatment effect were observed between the control and both the AAD-12+glufosinate and AAD-12+2,4-D+glufosinate entries, but were not accompanied by a significant FDR adjusted p-value. The mean results for all of these variables were also within the range found for the reference lines tested in this study.

TABLE 14

Summary of 2009 Agronomic Characteristics Results Across Locations

| Agronomic Measurement (Units) | Overall Trt Effect (Pr > F)[a] | Isoline Mean ± S.E. [Min-Max] | AAD-12 unsprayed Mean ± S.E. [Min-Max] (P-value, Adj. P)[b] | AAD-12 + Glufosinate Mean ± S.E. [Min-Max] (P-value, Adj. P)[b] | AAD-12 + 2,4-D Mean ± S.E. [Min-Max] (P-value, Adj. P)[b] | AAD-12 + 2,4-D + Glufosinate Mean ± S.E. [Min-Max] (P-value, Adj. P)[b] | Reference Range [Min-Max] |
|---|---|---|---|---|---|---|---|
| Stand Count - VC-V2 (number of plants emerged) | 0.099 | 187 ± 6 [141-215] | 181 ± 6 [149-213] (0.130, 0.559) | 177 ± 6 [134-208] (0.009, 0.322) | 182 ± 6 [123-216] (0.226, 0.683) | 184 ± 6 [148-220] (0.474, 0.905) | [102-211] |
| Early Population - VC-V2 (% of plants emerged) | 0.107 | 82.3 ± 2.3 [63-93.3] | 79.7 ± 2.3 [66.7-92.4] (0.127, 0.559) | 77.7 ± 2.3 [59.8-93] (0.010, 0.322) | 80.2 ± 2.3 [55-94.6] (0.221, 0.683) | 81.1 ± 2.3 [66-94.6] (0.463, 0.905) | [46-94.2] |
| Seedling Vigor - VC-V2 (Visual estimate of vigor; 1-10 scale, 10 = equivalent to non-transformed) | 0.931 | 10 ± 0.3 [7-10] | 9 ± 0.3 [8-10] (0.623, 0.905) | 10 ± 0.3 [8-10] (0.806, 0.919) | 10 ± 0.3 [7-10] (1.000, 1.000) | 9 ± 0.3 [7-10] (0.462, 0.905) | [8-10] |
| Final Population - R8 (number of plants remaining in plot) | 0.250 | 152 ± 19 [15-198] | 150 ± 19 [9-196] (0.659, 0.905) | 145 ± 19 [8-201] (0.070, 0.559) | 149 ± 19 [14-198] (0.432, 0.905) | 153 ± 19 [0-201] (0.778, 0.905) | [5-203] |
| Plant Vigor/Injury - V4 (Visual estimate of vigor; 1-10 scale, 10 = equivalent to non-transformed) | 0.255 | 10 ± 0.2 [9-10] | 10 ± 0.2 [8-10] (1.000, 1.000) | 9 ± 0.2 [7-10] (0.148, 0.559) | 10 ± 0.2 [8-10] (0.952, 1.000) | 9 ± 0.2 [7-10] (0.148, 0.559) | [8-10] |
| Plant Vigor/Injury - R1 (Visual estimate of vigor; 1-10 scale, 10 = equivalent to non-transformed) | 0.201 | 10 ± 0.2 [8-10] | 10 ± 0.2 [9-10] (0.725, 0.905) | 10 ± 0.2 [8-10] (0.124, 0.559) | 10 ± 0.2 [9-10] (0.725, 0.905) | 10 ± 0.2 [8-10] (0.276, 0.769) | [8-10] |
| Plant Vigor/Injury - R2 (Visual estimate of vigor; 1-10 scale, 10 = equivalent to non-transformed) | 0.036 | 10 ± 0.1 [8-10] | 10 ± 0.1 [9-10] (0.762, 0.905) | 10 ± 0.1 [9-10] (0.042, 0.559) | 10 ± 0.1 [8-10] (0.763, 0.905) | 10 ± 0.1 [8-10] (0.036, 0.559) | [8-10] |
| Lodging - R8 (0-100% scale, visual estimate based upon number of plants lodged) | 0.514 | 6 ± 5 [0-50] | 5 ± 5 [0-50] (0.605, 0.905) | 7 ± 5 [0-50] (0.354, 0.853) | 7 ± 5 [0-60] (0.522, 0.905) | 7 ± 5 [0-60] (0.348, 0.853) | [0-20] |
| Disease Incidence- R6 (0-100% scale - visual estimate of disease) | 0.078 | 9 ± 4 [0-40] | 8 ± 4 [0-40] (0.673, 0.905) | 9 ± 4 [0-40] (0.833, 0.919) | 10 ± 4 [0-40] (0.295, 0.787) | 7 ± 4 [0-30] (0.061, 0.559) | [0-25] |
| Insect Damage - R6 (0-100% scale - visual estimate of insect damage) | 0.762 | 5 ± 3 [0-30] | 5 ± 3 [0-20] (0.718, 0.905) | 6 ± 3 [0-30] (0.425, 0.905) | 6 ± 3 [0-30] (0.360, 0.853) | 6 ± 3 [0-30] (0.235, 0.683) | [0-30] |
| Plant Height (Plant height in cm of 10 plants in plot) | 0.518 | 90 ± 9 [27-140] | 89 ± 9 [30-142] (0.620, 0.905) | 88 ± 9 [21-142] (0.214, 0.683) | 89 ± 9 [46-140] (0.767, 0.905) | 90 ± 9 [48-155] (0.645, 0.905) | [32-140] |
| Days to Flowering (Heat units when 50% of plants reach flowering) | 0.441 | 958.8 ± 30.9 [835.1-1056] | 946.3 ± 30.9 [835.1-1056] (0.203, 0.683) | 962.9 ± 30.9 [859.7-1074] (0.672, 0.905) | 958.7 ± 30.9 [835.1-1056] (0.987, 1.000) | 962 ± 30.9 [835.1-1056] (0.744, 0.905) | [835.1-1074] |
| Days to Maturity (Heat units when 50% of plants reach physiological maturity) | 0.124 | 2063.3 ± 69.1 [1696-2272.4] | 2063.9 ± 69.1 [1696-2272.4] (0.869, 0.943) | 2070.3 ± 69.1 [1696-2272.4] (0.052, 0.559) | 2063.5 ± 69.1 [1696-2272.4] (0.969, 1.000) | 2069.2 ± 69.1 [1696-2272.4] (0.098, 0.559) | [1696-2290.8] |
| Number of Pods (number of pods in 5 plants) | 0.356 | 254 ± 41 [137-460] | 249 ± 41 [159-460] (0.691, 0.905) | 273 ± 41 [155-490] (0.123, 0.559) | 261 ± 41 [144-461] (0.527, 0.905) | 258 ± 41 [154-440] (0.747, 0.905) | [107-562] |
| Number of Seeds (number of seeds in 5 plants) | 0.324 | 642 ± 92 [254-1289] | 698 ± 92 [406-1256] (0.102, 0.559) | 704 ± 92 [420-1330] (0.072, 0.559) | 693 ± 92 [472-1114] (0.136, 0.559) | 667 ± 92 [443-1109] (0.443, 0.905) | [321-1221] |

TABLE 14-continued

Summary of 2009 Agronomic Characteristics Results Across Locations

| Agronomic Measurement (Units) | Overall Trt Effect (Pr > F)[a] | Isoline Mean ± S.E. [Min-Max] | AAD-12 unsprayed Mean ± S.E. [Min-Max] (P-value, Adj. P)[b] | AAD-12 + Glufosinate Mean ± S.E. [Min-Max] (P-value, Adj. P)[b] | AAD-12 + 2,4-D Mean ± S.E. [Min-Max] (P-value, Adj. P)[b] | AAD-12 + 2,4-D + Glufosinate Mean ± S.E. [Min-Max] (P-value, Adj. P)[b] | Reference Range [Min-Max] |
|---|---|---|---|---|---|---|---|
| Yield (grams of harvested seed from entire plot) | 0.742 | 2730 ± 310 [1900-4500] | 2800 ± 310 [1700-4400] (0.503, 0.905) | 2680 ± 310 [1860-4300] (0.696, 0.905) | 2700 ± 310 [1750-4700] (0.829, 0.919) | 2800 ± 310 [1950-4800] (0.527, 0.905) | [1360-4600] |

[a]Unit of measure was not converted prior to analysis.
[b]Overall treatment effect estimated using an F-test.
[c]Comparison to the control using t-tests (P-value); P-values adjusted (Adj. P) using a False Discovery Rate (FDR) procedure; P-values <0.05 were considered significant.

Example 7.3

Ecological Evaluations

The soybean Event DAS-68416-4 field trials were monitored and observed by personnel familiar with soybean cultivation practices (breeders, field station managers, field agronomists, field associates). The personnel conducting the field tests visually monitored the incidence of plant disease and pests on soybean Event DAS-68416-4 plants compared to the conventional soybean varieties in the same trials. As part of Experiment 1 described in Example 7.1 disease and insect damage was rated on a numerical scale of 0-100%, with 0% representing on damage due to disease incidence or insect resistance. Table 15 shows results across the 6 sites described in Experiment 1.

Event DAS-68416-4+both herbicides. However no significant overall treatment effect was observed, the difference between the soybean Event DAS-68416-4 treatment and the control was small, and differences were not shared among the different soybean Event DAS-68416-4 treatments.

Ecological observations were also made from all USDA APHIS notified field trials conducted in 2006-2008. Incidence of disease and insect presence in trials of soybean Event DAS-68416-4 plants were recorded and differences in incidence or response of soybean Event DAS-68416-4 plants compared to the conventional control were examined. In all cases, no differences were seen in any of the trials of soybean Event DAS-68416-4 plants compared to the conventional controls. The disease and insect stressors observed in trials of soybean Event DAS-68416-4 and conventional soybeans are described in Table 16. These observations

TABLE 15

Analysis of disease incidence and insect damage from Experiment1 (Example 7.1).

| Analyte | Overall Treatment Effect (Pr > F)[a] | Control | Unsprayed (P-value,[b] Adj. P)[c] | Sprayed Glufosinate (P-value, Adj. P) | Sprayed 2,4-D (P-value Adj. P) | Sprayed Both (P-value, Adj. P) |
|---|---|---|---|---|---|---|
| Disease Incidence (%)[e] | 0.422 | 13.1 | 12.6 (0.803, 0.853) | 11.8 (0.456, 0.671) | 11.1 (0.251, 0.575) | 10.1 (0.091, 0.575) |
| Insect Damage[e] | 0.332 | 24.1 | 21.8 (0.140, 0.575) | 22.1 (0.204, 0.575) | 22.3 (0.236, 0.575) | 20.9 (0.044, 0.575) |

[a]Overall treatment effect estimated using an F-test.
[b]Comparison of the sprayed and unsprayed treatments to the control using a t-test.
[c]P-values adjusted using a False Discovery Rate (FDR) procedure.
[e]Visual estimate on 0-100% scale; 0% = no damage.

No statistically significant differences were observed for disease incidence. For insect damage, a significant paired t-test was observed between the control and the soybean support the conclusion that the response of soybean Event DAS-68416-4 to ecological stressors does not differ from that of conventional soybean.

TABLE 16

Disease and insect stressors observed in trials of DAS-68416-4 and conventional soybean.

| Year | USDA Notification Number | State(s) | County | Diseases | Insects |
|---|---|---|---|---|---|
| 2007 | 06-292-105n | IN | Benton | | aphids bean leaf beetles corn rootworm beetles Japanese beetles lady bugs leaf hoppers |

TABLE 16-continued

Disease and insect stressors observed in trials of DAS-68416-4 and conventional soybean.

| Year | USDA Notification Number | State(s) | County | Diseases | Insects |
|---|---|---|---|---|---|
| 2007-2008 | 07-242-107n | PR | Santa Isabel | Carla virus | spider mites whiteflies |
| 2008 | 08-071-107n | CA | Tulare | brown spot | aphids |
| | | IL | Clinton | Cercospora leaf blight | bean leaf beetles |
| | | IN | Benton | rust | grasshoppers |
| | | IN | Parke | Septoria leaf spot | Japanese beetles |
| | | IA | Jefferson | | lady bugs |
| | | IA | Story | | stink bugs |
| | | MN | Dakota | | thrips |
| | | MS | Washington | | yellow-striped |
| | | NE | York | | armyworms |

Example 7.4

Germancy and Dormancy Evaluations

Changes in seed dormancy characteristics were evaluated by looking at the germination of soybean Event DAS-68416-4 seed compared with the near isogenic comparator under warm and cold conditions.

For the warm germination test, soybean Event DAS-68416-4 and control soybean seeds were placed 25/plate into petri dishes containing germination pads saturated with water and excess water drained. The plates were placed at 25° C. and held under these conditions for 5 days. Sixteen plates (400 seeds) were prepared per line. After five days, the number of non-germinated seeds was recorded.

For the cold germination test, seeds were planted at 100 seeds per half-flat filled with potting soil. Flats were sub-watered and held at 10° C. for 7 days followed by exposure to 25° C. for 5 days, after which the number of non-germinated seed was recorded.

Data from each test was analyzed by ANalysis of VAriance (ANOVA) using a completely randomized design with four replicates of 100 seeds per replicate. Data were transformed using the arcsine of the square root of the number of germinated seeds divided by 100 for statistical analysis. Percent germination is summarized in Tale 17.

TABLE 17

Germination of soybean Event DAS-68416-4 seeds under warm and cold conditions.

| | | Replicate | | | | |
|---|---|---|---|---|---|---|
| Test | Line | 1 | 2 | 3 | 4 | Mean |
| Warm | DAS-68416-4 | 97 | 100 | 99 | 100 | 99.0 |
| Warm | Control | 100 | 100 | 99 | 97 | 99.0 |
| Cold | DAS-68416-4 | 92 | 92 | 92 | 89 | 91.3 |
| Cold | Control | 98 | 88 | 98 | 96 | 95.0 |

There were no significant differences in germination between soybean Event DAS-68416-4 and control soybean seed in either the warm or cold germination experiments (Pr>F=1.0 and 0.13, respectively). These results indicate that the seed dormancy characteristics have not been changed in soybean Event DAS-68416-4.

Example 7.5

Summary of Agronomic, Disease, Pest, and Germancy Characteristics

Agronomic data evaluating plant growth characteristics throughout the growing season demonstrate the equivalence of soybean Event DAS-68416-4 with conventional non-transgenic soybean. Plant growth and phenotypic characteristics, response to ecological stressors as indicated by susceptibility to disease and insect pressure, and germination and dormancy characteristics were unchanged between soybean Event DAS-68416-4 plants and conventional soybeans across diverse environments. Therefore, these data support the conclusion that agronomic, disease, and pest characteristics of soybean Event DAS-68416-4 are not significantly different from that of conventional soybeans, and there is no indication that soybean Event DAS-68416-4 soybeans will post an increased plant pest risk.

Benjamini, Y., Hochberg, Y. (1995) Controlling the false discovery rate: A practical and powerful approach to multiple testing. J. Royal Statistical Soc. B, 57:289-300.

Example 8

Grain and Forage Composition

Compositional analysis was performed on soybean forage and grain to investigate the equivalency between soybean Event DAS-68416-4 (sprayed with 2,4-D, glufosinate, 2,4-D+glufosinate, or not sprayed with 2,4-D or glufosinate) and conventional soybean. Trials were conducted at six test sites located within the major soybean-producing regions of the U.S. and Canada using seed lines with and without soybean Event DAS-68416-4. The test sites represent regions of diverse agronomic practices and environmental conditions and were the same sites used for protein expression analysis and agronomic Experiment 1 described in Example 7.1. The trials were located in Iowa, Illinois, Indiana, Nebraska, and Ontario, Canada (2 sites).

Samples of soybean forage and grain were analyzed for nutrient content with a variety of tests. The analyses performed for forage included protein, fat, ash, moisture, carbohydrate, acid detergent fiber (ADF), neutral detergent fiber (NDF), calcium and phosphorus. The analyses performed for grain included proximates (ash, total fat, moisture, protein, cholesterol, carbohydrate), fiber, minerals, amino acids, fatty acid, vitamins, anti-nutrients.

The results of the nutritional analysis for soybean forage and grain were compared with values reported in literature. Analysis of variance was also conducted across the field sites using a mixed model. Entry was considered a fixed effect, and location, block within location, and location-by-entry were designated as random effects. The significance of an overall treatment effect was estimated using an F-test. Paired contrasts were made between soybean Event DAS-68416-4 (unsprayed AAD-12; not sprayed with 2,4-D or glufosinate), soybean Event DAS-68416-4 sprayed with glufosinate (soybean Event DAS-68416-4+glufosinate), soybean Event DAS-68416-4 sprayed with 2,4-D (soybean Event DAS-68416-4+2,4-D), and soybean Event DAS-68416-4 sprayed with both glufosinate and 2,4-D transgenic entries (soybean Event DAS-68416-4+both), and the control entry using t-tests.

Due to the large number of contrasts made in this study, multiplicity was an issue. Multiplicity is an issue when a large number of comparisons are made in a single study to look for unexpected effects. Under these conditions, the probability of falsely declaring differences based on comparison-wise p-values is very high ($1-0.95^{number\ of\ comparisons}$). In this study there were four comparisons per analyte (75 quantitated analytes), resulting in 300 comparisons made in the across-site composition analysis. Therefore, the probability of declaring one or more false differences based on unadjusted p-values was >99.99%.

One method to account for multiplicity is to adjust p-values to control the experiment-wise error rate (probability that all declared differences are significant), but when many comparisons are made in a study, the power for detecting specific effects can be reduced significantly. An alternative with much greater power is to adjust p-values to control the probability that each declared difference is significant. This can be accomplished using False Discovery Rate (FDR) procedures (Benjamini and Hochberg, 1995). Therefore the p-values were adjusted using FDR to improve discrimination of true differences among treatments from random effects (false positives).

Example 8.1

Compositional Analysis of Soybean Forage

An analysis of the protein, fat, ash, moisture, carbohydrate, acid detergent fiber (ADF), neutral detergent fiber (NDF), calcium and phosphorus in soybean forage samples from the control, unsprayed soybean Event DAS-68416-4, soybean Event DAS-68416-4+glufosinate, soybean Event DAS-68416-4+2,4-D and soybean Event DAS-68416-4+both herbicides was performed. A summary of the results across all locations is shown in Table 18.

No statistical differences were observed in the across-site analysis between the control and transgenic entries for protein, fat, ash, moisture, carbohydrates, ADF, NDF, calcium or phosphorus. Mean ash values across sites for soybean Event DAS-68416-4+glufosinate and soybean Event DAS-68416-4+both herbicides was outside of the literature range as was the NDF value for soybean Event DAS-68416-4+glufosinate and soybean Event DAS-68416-4+2,4-D. ADF values for all treatments including the non-transgenic control were also outside of the literature values. Mean values were not significantly different between the non-transgenic control and any transgenic entry for any proximate, fiber type, or mineral in forage. Based on these compositional constituents, the forage from soybean Event DAS-68416-4 soybean was substantially equivalent to that of the near-isogenic non-transgenic control.

TABLE 18

Summary of the proximate, fiber and mineral analysis of soybean forage (% dry weight).

| Analyte | Literature Values[a] | Overall Treatment Effect $(Pr > F)$[b] | Control | Unsprayed (P-value,[c] Adj. P)[d] | Sprayed Glufosinate (P-value, Adj. P) | Sprayed 2,4-D (P-value, Adj. P) | Sprayed Both (P-value, Adj. P) |
|---|---|---|---|---|---|---|---|
| Proximate | | | | | | | |
| Protein | 11.2-24.7 | 0.805 | 19.1 | 19.0 (0.881, 0.930) | 19.4 (0.666, 0.819) | 18.9 (0.744, 0.860) | 18.6 (0.441, 0.634) |
| Fat | 1.30-5.1 | 0.046 | 4.11 | 4.46 (0.216, 0.403) | 3.66 (0.107, 0.254) | 4.17 (0.844, 0.908) | 3.74 (0.186, 0.360) |
| Ash | 6.72-10.8 | 0.092 | 10.6 | 10.1 (0.567, 0.767) | 11.1 (0.546, 0.741) | 10.2 (0.672, 0.819) | 12.3 (0.051, 0.151) |
| Moisture (% fresh weight) | 73.5-81.6 | 0.569 | 77.8 | 78.5 (0.255, 0.444) | 78.4 (0.330, 0.539) | 77.8 (0.960, 0.970) | 77.8 (0.976, 0.979) |
| Carbohydrates | 59.8-74.7 | 0.675 | 66.2 | 66.5 (0.830, 0.902) | 65.9 (0.739, 0.860) | 66.7 (0.641, 0.808) | 65.3 (0.366, 0.564) |
| Fiber | | | | | | | |
| Acid Detergent Fiber (ADF) | 32.0-38.0 | 0.967 | 30.2 | 30.4 (0.904, 0.936) | 30.6 (0.797, 0.875) | 29.7 (0.746, 0.860) | 30.7 (0.740, 0.860) |
| Neutral Detergent Fiber (NDF) | 34.0-40.0 | 0.375 | 34.4 | 34.7 (0.877, 0.930) | 33.1 (0.397, 0.596) | 32.0 (0.135, 0.297) | 34.5 (0.948, 0.962) |
| Minerals | | | | | | | |
| Calcium | NR | 0.246 | 1.39 | 1.36 (0.361, 0.560) | 1.40 (0.664, 0.819) | 1.38 (0.842, 0.908) | 1.43 (0.178, 0.352) |
| Phosphorus | NR | 0.957 | 0.263 | 0.266 (0.671, 0.819) | 0.269 (0.442, 0.634) | 0.266 (0.696, 0.831) | 0.265 (0.754, 0.860) |

[a]Combined range.
[b]Overall treatment effect estimated using an F-test.
[c]Comparison of the transgenic treatments to the control using t-tests.
[d]P-values adjusted using a False Discovery Rate (FDR) procedure.
NR = not reported
Bolded mean values are outside of the reported literature range.
Bolded P-values are significant (<0.05).

Example 8.2

Compositional Analysis of Soybean Grain

Example 8.2.1

Proximates and Fiber

An analysis of the protein, fat, ash, moisture, cholesterol, carbohydrate, ADF, NDF and total dietary fiber in soybean grain samples from the control, unsprayed soybean Event DAS-68416-4, soybean Event DAS-68416-4+glufosinate, soybean Event DAS-68416-4+2,4-D and soybean Event DAS-68416-4+both herbicides was performed. A summary of the results across all locations is shown in Table 19.

No statistical differences were observed in the across-site analysis between the control and transgenic entries for the fat, ADF or total dietary fiber. However, ADF was slightly higher than the literature range for the soybean Event DAS-68416-4+2,4-D entry.

Protein levels were significantly different in the across-site analysis based on the unadjusted p-value for the unsprayed, soybean Event DAS-68416-4+2,4-D, and soybean Event DAS-68416-4+both herbicides compared with the control. However, after FDR adjustment, only the p-value for the soybean Event DAS-68416-4+2,4-D was significant, and overall mean protein values for all treatments were within the reported literature values, indicating that the differences were not biologically meaningful.

A significant unadjusted p-value was observed in the across site analysis of ash between the control and the 2,4-D sprayed soybean Event DAS-68416-4 treatment, but no overall treatment effect or adjusted p-value was observed. Ash values were also within the reported literature values, indicating that the differences were not biologically meaningful.

Moisture levels were significantly different in the across-site analysis based on the unadjusted p-value for the unsprayed, soybean Event DAS-68416-4+2,4-D, and soybean Event DAS-68416-4+both herbicides compared with the control. However, the overall treatment effect was not significant for moisture, only the soybean Event DAS-68416-4+2,4-D treatment had a significant FDR-adjusted p-value, and the mean moisture levels for all treatments were within the literature ranges. This indicated that the differences were not biologically meaningful.

Cholesterol values were all less than Limit of Quantitation (<LOQ) and no literature values were reported.

Carbohydrate levels were significantly different in the across-site analysis based on the unadjusted p-value for the unsprayed, soybean Event DAS-68416-4+glufosinate, and soybean Event DAS-68416-4+2,4-D compared with the control. However, only the soybean Event DAS-68416-4+2,4-D treatment was significantly different from the control based on the FDR adjusted p-value and all treatment means were within the reported literature values, indicating equivalence to non-transgenic soybean.

NDF levels were significantly different in the across-site analysis based on the unadjusted p-value for soybean Event DAS-68416-4+glufosinate compared with the control, but this was not accompanied by a significant adjusted p-value or an overall treatment effect. NDF across-site values were slightly higher than the reported literature values for the soybean Event DAS-68416-4+glufosinate and soybean Event DAS-68416-4+2,4-D entries, but the differences were <9% compared with the non-transgenic near-isogenic control.

Based on these compositional constituents, the grain from soybean Event DAS-68416-4 was substantially equivalent to that of non-transgenic soybean.

TABLE 19

Summary of the proximate and fiber analysis of soybean grain (% dry weight).

| Analyte | Literature Values[a] | Overall Treatment Effect (Pr > F)[b] | Control | Unsprayed (P-value,[c] Adj. P)[d] | Sprayed Glufosinate (P-value, Adj. P) | Sprayed 2,4-D (P-value, Adj. P) | Sprayed Both (P-value, Adj. P) |
|---|---|---|---|---|---|---|---|
| Proximate | | | | | | | |
| Protein | 32.0-45.5 | 0.004 | 39.2 | 38.3 (0.009, 0.051) | 38.8 (0.186, 0.360) | 37.8 (0.0003, 0.009) | 38.5 (0.035, 0.122) |
| Fat | 8.10-24.7 | 0.105 | 17.1 | 17.1 (0.877, 0.930) | 16.6 (0.059, 0.169) | 16.7 (0.142, 0.305) | 17.2 (0.674, 0.819) |
| Ash | 3.89-6.99 | 0.315 | 4.92 | 5.04 (0.176, 0.351) | 5.04 (0.175, 0.351) | 5.10 (0.048, 0.145) | 5.07 (0.099, 0.240) |
| Moisture % fresh weight | 4.70-34.4 | 0.066 | 14.9 | 14.1 (0.047, 0.143) | 14.3 (0.122, 0.276) | 13.7 (0.006, 0.043) | 14.0 (0.037, 0.124) |
| Cholesterol | NR | NA | <LOQ | <LOQ | <LOQ | <LOQ | <LOQ |
| Carbohydrate | 29.6-50.2 | 0.010 | 38.8 | 39.6 (0.046, 0.143) | 39.6 (0.044, 0.138) | 40.3 (0.001, 0.011) | 39.3 (0.241, 0.432) |
| Fiber | | | | | | | |
| Acid Detergent Fiber (ADF) | 7.81-18.6 | 0.561 | 17.8 | 17.6 (0.772, 0.868) | 18.0 (0.772, 0.868) | 18.8 (0.190, 0.362) | 18.1 (0.685, 0.825) |
| Neutral Detergent Fiber (NDF) | 8.53-21.3 | 0.184 | 20.1 | 20.8 (0.386, 0.585) | 21.9 (0.042, 0.134) | 21.6 (0.090, 0.225) | 20.3 (0.754, 0.860) |
| Total Dietary Fiber | NR | 0.770 | 31.6 | 31.7 (0.899, 0.936) | 31.7 (0.897, 0.936) | 32.1 (0.466, 0.653) | 32.5 (0.286, 0.482) |

[a]Combined range.
[b]Overall treatment effect estimated using an F-test.
[c]Comparison of the transgenic treatments to the control using t-tests.
[d]P-values adjusted using a False Discovery Rate (FDR) procedure.
NA = statistical analysis was not performed since a majority of the data was <LOQ.
NR = not reported.
Bolded mean values are outside of the reported literature range.
Bolded P-values are significant ($<0.05$).

Example 8.2.2

Minerals

The analysis of the calcium, chromium, copper, iodine, iron, magnesium, manganese, molybdenum, phosphorus, potassium, selenium, sodium and zinc in soybean grain samples from the control, unsprayed soybean Event DAS-68416-4, soybean Event DAS-68416-4+glufosinate, soybean Event DAS-68416-4+2,4-D and soybean Event DAS-68416-4+both herbicides was performed. A summary of the results across all locations is shown in Table 20.

No statistical differences were observed in the across-site analysis between the control and transgenic entries based on the unadjusted p-value for the chromium, copper, iodine, iron, manganese, molybdenum, phosphorus, selenium and sodium (not detected).

Calcium had a significant difference in the across-site analysis based on the unadjusted p-value for the soybean Event DAS-68416-4+2,4-D but this was not associated with a significant FDR adjusted p-value or overall treatment effect, and all treatment means fell within the literature range, indicating that the difference was not biologically meaningful.

Magnesium levels were significantly different in the across-site analysis for the soybean Event DAS-68416-4+both herbicides and soybean Event DAS-68416-4+glufosinate compared with the control based on the unadjusted and adjusted p-values, respectively, but the overall treatment effect was not significant. Magnesium across site mean values were slightly lower than the reported literature values, but the differences were small (<3%) in comparison to the control and all soybean Event DAS-68416-4 entries were closer to literature values compared with the control.

All soybean Event DAS-68416-4 entries had significantly higher potassium values compared with the control in the across-site analysis. However, differences were small (<5%) in comparison to the control, and the all soybean Event DAS-68416-4 entries were closer to the literature range compared with the control.

A difference in zinc levels was significant in the across-site analysis based on the unadjusted p-value for soybean Event DAS-68416-4+both herbicides, however this was not accompanied by a significant FDR-adjusted p-value or overall treatment effect, and the difference was small (<4%).

Based on these compositional constituents, the grain from soybean Event DAS-68416-4 was substantially equivalent to that of non-transgenic soybean.

TABLE 20

Summary of the mineral analysis of soybean grain (mg/100 g dry weight).

| Analyte | Literature Values[a] | Overall Treatment Effect (Pr > F)[b] | Control | Unsprayed (P-value,[c] Adj. P)[d] | Sprayed Glufosinate (P-value, Adj. P) | Sprayed 2,4-D (P-value, Adj. P) | Sprayed Both P-value, Adj. P) |
|---|---|---|---|---|---|---|---|
| Calcium | 117-307 | 0.102 | 256 | 265 (0.174, 0.351) | 264 (0.237, 0.432) | 274 (0.010, 0.057) | 269 (0.050, 0.148) |
| Chromium (ppb) | NR | 0.775 | 145 | 149 (0.912, 0.941) | 175 (0.468, 0.653) | 126 (0.613, 0.796) | 137 (0.855, 0.916) |
| Copper | NR | 0.887 | 1.31 | 1.28 (0.534, 0.728) | 1.30 (0.788, 0.873) | 1.27 (0.367, 0.564) | 1.28 (0.461, 0.649) |
| Iodine | NR | 0.285 | 0.027 | 0.023 (0.430, 0.632) | 0.021 (0.182, 0.358) | 0.032 (0.348, 0.551) | 0.023 (0.348, 0.551) |
| Iron | 5.54-11.0 | 0.917 | 8.15 | 8.46 (0.719, 0.853) | 8.95 (0.353, 0.552) | 8.53 (0.656, 0.819) | 8.59 (0.608, 0.796) |
| Magnesium | 219-313 | 0.082 | 210 | 212 (0.437, 0.634) | 215 (0.020, 0.087) | 213 (0.143, 0.305) | 215 (0.021, 0.088) |
| Manganese | NR | 0.984 | 2.56 | 2.60 (0.608, 0.796) | 2.60 (0.618, 0.799) | 2.58 (0.781, 0.873) | 2.59 (0.698, 0.831) |
| Molybdnum (ppb) | NR | 0.845 | 2165 | 2557 (0.353, 0.552) | 2462 (0.479, 0.665) | 2563 (0.346, 0.551) | 2284 (0.722, 0.853) |
| Phosphorus | 507-935 | 0.675 | 583 | 589 (0.630, 0.804) | 599 (0.191, 0.363) | 596 (0.272, 0.469) | 594 (0.349, 0.551) |
| Potassium | 1868-2316 | 0.0005 | 1801 | 1876 (0.0003, 0.009) | 1882 (0.0001, 0.006) | 1883 (0.0001, 0.006) | 1864 (0.001, 0.019) |
| Selenium (ppb) | NR | 0.490 | 490 | 523 (0.626, 0.802) | 520) (0.659, 0.819) | 511 (0.758, 0.861) | 418 (0.280, 0.475) |
| Sodium | NR | NA | 20.9 | <LOQ | 17.3 | 19.7 | 14.1 |
| Zinc | NR | 0.096 | 5.06 | 5.07 (0.868, 0.926) | 5.19 (0.117, 0.268) | 5.21 (0.074, 0.197) | 5.25 (0.027, 0.105) |

[a]Combined range.
[b]Overall treatment effect estimated using an F-test.
[c]Comparison of the transgenic treatments to the control using t-tests.
[d]P-values adjusted using a False Discovery Rate (FDR) procedure.
NR = not reported.
NA = statistical analysis was not performed since a majority of the data was <LOQ.
Bolded mean values are outside of the reported literature range.
Bolded P-values are significant (<0.05).

Example 8.2.3

Amino Acids

An analysis of the following amino acids: alanine, arginine, aspartic acid, cystine, glutamic acid glycine, histidine, isoleucine, leucine, lysine, methionine, phenylalanine, proline, serine, threonine, tryptophan, tyrosine, and valine; in soybean grain samples from the control, unsprayed soybean Event DAS-68416-4, soybean Event DAS-68416-4+glufosinate, soybean Event DAS-68416-4+2,4-D and soybean Event DAS-68416-4+both herbicides was performed. A summary of the results across all locations is shown in Table 21.

No statistical differences were observed between the control and transgenic entries for cysteine, methionine, proline, tyrosine or tryptophan. The isoleucine level for soybean Event DAS-68416-4+2,4-D was significantly different from the control based on the unadjusted p-value, but this was not accompanied by a significant FDR-adjusted p-value or a significant overall treatment effect. The levels of the remaining 12 amino acids were slightly lower (<7%) for two or more of the soybean Event DAS-68416-4 entries compared with the control, but all fell within the literature range for non-transgenic soybean. All amino acids for all entries were within the literature ranges, indicating that the differences were not biologically meaningful. Based on these compositional constituents, the grain from soybean Event DAS-68416-4 was substantially equivalent to that of non-transgenic soybean.

Example 8.2.4

Fatty Acids

An analysis of 22 fatty acids in soybean grain samples from the control, unsprayed soybean Event DAS-68416-4, soybean Event DAS-68416-4+glufosinate, soybean Event DAS-68416-4+2,4-D and soybean Event DAS-68416-4+ both herbicides was performed. A summary of the results across all locations is shown in Table 22.

The fatty acids 10:0 capric, 15:0 pentadecanoic, 15:1 pentadecenoic, 20:3 eicosatrienoic, 20:4 arachidonic, 8:0 caprylic, 12:0 lauric, 14:0 myristic, 14:1 myristoleic, 17:1 heptadecenoic, 18:3 gamma linolenic, and 20:2 eicosadienoic acids were analyzed and the results were <LOQ. The fatty acids 16:0 palmitic, 17:0 heptadecanoic, and 20:1 eicosenoic were not significantly different between the control and the AAD-12 entries, although 20:1 eicosenoic values were lower than the reported literature values for AAD-12+glufosinate and AAD-12+both herbicides. However, the differences were small (<5%) in comparison to the control.

The level of 16:1 palmitoleic was significantly different between the control and the unsprayed soybean Event DAS-

TABLE 21

Summary of the amino acid analysis of soybean grain (% dry weight).

| Analyte | Literature Values[a] | Overall Treatment Effect (Pr > F)[b] | Control | Unsprayed (P-value,[c] Adj. P)[d] | Sprayed Glufosinate (P-value, Adj. P) | Sprayed 2,4-D (P-value, Adj. P) | Sprayed Both (P-value, Adj. P) |
|---|---|---|---|---|---|---|---|
| Alanine | 1.51-2.10 | 0.003 | 1.74 | 1.70 (0.001, 0.017) | 1.70 (0.004, 0.033) | 1.69 (0.0003, 0.009) | 1.71 (0.014, 0.067) |
| Arginine | 2.29-3.40 | 0.007 | 3.15 | 2.97 (0.004, 0.033) | 3.00 (0.012, 0.066) | 2.94 (0.001, 0.015) | 2.96 (0.003, 0.026) |
| Aspartic Acid | 3.81-5.12 | 0.007 | 4.52 | 4.41 (0.004, 0.033) | 4.44 (0.037, 0.124) | 4.38 (0.0005, 0.010) | 4.43 (0.014, 0.067) |
| Cystine | 0.37-0.81 | 0.254 | 0.60 | 0.60 (0.637, 0.808) | 0.60 (0.787, 0.873) | 0.61 (0.900, 0.936) | 0.61 (0.110, 0.260) |
| Glutamic Acid | 5.84-8.20 | 0.002 | 6.98 | 6.76 (0.001, 0.015) | 6.83 (0.019, 0.086) | 6.70 (0.0001, 0.006) | 6.80 (0.006, 0.043) |
| Glycine | 1.46-2.00 | 0.001 | 1.74 | 1.69 (0.0004, 0.009) | 1.70 (0.002, 0.023) | 1.69 (0.0001, 0.006) | 1.70 (0.001, 0.017) |
| Histidine | 0.88-1.22 | 0.003 | 1.09 | 1.06 (0.002, 0.023) | 1.07 (0.014, 0.067) | 1.05 (0.0002, 0.007) | 1.07 (0.013, 0.067) |
| Isoleucine | 1.54-2.08 | 0.232 | 1.87 | 1.83 (0.100, 0.241) | 1.85 (0.450, 0.642) | 1.82 (0.042, 0.134) | 1.85 (0.514, 0.708) |
| Leucine | 2.20-4.00 | 0.010 | 3.06 | 3.00 (0.007, 0.046) | 3.02 (0.068, 0.186) | 2.98 (0.001, 0.011) | 3.01 (0.037, 0.124) |
| Lysine | 2.29-2.84 | 0.005 | 2.56 | 2.51 (0.004, 0.034) | 2.52 (0.028, 0.105) | 2.49 (0.0003, 0.009) | 2.52 (0.022, 0.093) |
| Methionine | 0.43-0.68 | 0.433 | 0.56 | 0.55 (0.377, 0.575) | 0.55 (0.245, 0.438) | 0.55 (0.089, 0.225) | 0.55 (0.742, 0.860) |
| Phenylalanine | 1.60-2.35 | 0.008 | 2.02 | 1.97 (0.014, 0.067) | 1.98 (0.044, 0.138) | 1.94 (0.0004, 0.009) | 1.97 (0.027, 0.105) |
| Proline | 1.69-2.28 | 0.374 | 1.91 | 1.85 (0.059, 0.169) | 1.88 (0.400, 0.597) | 1.87 (0.155, 0.324) | 1.87 (0.240, 0.432) |
| Serine | 1.11-2.48 | 0.063 | 1.99 | 1.95 (0.082, 0.210) | 1.95 (0.115, 0.268) | 1.91 (0.006, 0.043) | 1.93 (0.021, 0.088) |
| Threonine | 1.14-1.89 | 0.001 | 1.62 | 1.57 (0.002, 0.020) | 1.58 (0.008, 0.048) | 1.55 (<0.0001, 0.006) | 1.57 (0.002, 0.022) |
| Tryptophan | 0.36-0.67 | 0.330 | 0.43 | 0.43 (0.593, 0.787) | 0.43 (0.981, 0.981) | 0.43 (0.904, 0.936) | 0.42 (0.095, 0.235) |
| Tyrosine | 1.02-1.61 | 0.449 | 1.36 | 1.34 (0.275, 0.471) | 1.35 (0.517, 0.708) | 1.33 (0.096, 0.235) | 1.33 (0.153, 0.321) |
| Valine | 1.50-2.44 | 0.159 | 1.97 | 1.92 (0.032, 0.116) | 1.94 (0.279, 0.475) | 1.92 (0.038, 0.124) | 1.95 (0.346, 0.551) |

[a]Combined range.
[b]Overall treatment effect estimated using an F-test.
[c]Comparison of the transgenic treatments to the control using t-tests.
[d]P-values adjusted using a False Discovery Rate (FDR) procedure.
Bolded mean values are outside of the reported literature range.
Bolded P-values are significant (<0.05).

68416-4, soybean Event DAS-68416-4+glufosinate, soybean Event DAS-68416-4+2,4-D, and soybean Event DAS-68416-4+both herbicides based on unadjusted p-values. However, only the unsprayed soybean Event DAS-68416-4 entry had a FDR-adjusted p-value that was significant for 16:1 palmitoleic. The 16:1 palmitoleic across-site value was lower for this treatment compared with the reported literature values, but the difference was small (<13%) in comparison to the near-isogenic control.

The level of 18:0 stearic was significantly different between the control and the unsprayed and soybean Event DAS-68416-4+glufosinate, based on unadjusted p-values. However, no significant differences were observed based on the adjusted p-values or the overall treatment effect, and all entries were within the reported literature values, indicating equivalence to non-transgenic soybean.

The level of 18:1 oleic was significantly different between the control and the unsprayed soybean Event DAS-68416-4, soybean Event DAS-68416-4+glufosinate, soybean Event DAS-68416-4+2,4-D, and soybean Event DAS-68416-4+ both herbicides. However, 18:1 oleic levels were within the reported literature values for all treatments, indicating equivalence to non-transgenic soybean.

The level of 18:2 linoleic was significantly different between the control and the unsprayed and soybean Event DAS-68416-4+2,4-D, based on unadjusted p-values. However, no significant differences were observed in the adjusted p-values or the overall treatment effect, and 18:2 linoleic levels were within the reported literature values for all treatments, indicating equivalence to non-transgenic soybean.

Levels of 18:3 linolenic were significantly different between each of the soybean Event DAS-68416-4 entries and the control based on unadjusted p-values, and the adjusted p-values were also significant between the unsprayed soybean Event DAS-68416-4 and soybean Event DAS-68416-4+both herbicide treatment compared with the control. No literature values are available for 18:3 linolenic, however, differences between the soybean Event DAS-68416-4 and control treatment were small (<6%).

The level of 20:0 arachidic was significantly different between the control and the unsprayed soybean Event DAS-68416-4, soybean Event DAS-68416-4+glufosinate, soybean Event DAS-68416-4+2,4-D, and soybean Event DAS-68416-4+both herbicides based on unadjusted p-values, and 20:0 arachidic also had significant differences in the across-site analysis in the adjusted p-value for the unsprayed and soybean Event DAS-68416-4+glufosinate treatments. However, 20:0 arachidic levels were within the reported literature values for all treatments, indicating equivalence to non-transgenic soybean.

The level of 22:0 behenic was significantly different between the control and the unsprayed, soybean Event DAS-68416-4+glufosinate, soybean Event DAS-68416-4+ 2,4-D, and soybean Event DAS-68416-4+both herbicides based on unadjusted p-values, and the level of 22:0 behenic also had a significant difference in the across-site analysis in the adjusted p-value for the soybean Event DAS-68416-4+ glufosinate. However, there were no significant overall treatment effect, and 22:0 behenic levels were within the reported literature values for all treatments, indicating equivalence to non-transgenic soybean.

Of the 22 fatty acids investigated, all four soybean Event DAS-68416-4 entries were either statistically indistinguishable from the control or within literature values for 21 of the fatty acids. In one case (unsprayed soybean Event DAS-68416-4; 16:1 palmitoleic), the value was slightly under the minimum literature values and statistically different from the control (<13% lower), however, all three sprayed treatments were within the literature range. Based on these compositional constituents, the grain from soybean Event DAS-68416-4 was substantially equivalent to that of non-transgenic soybean.

TABLE 22

Summary of the fatty acid analysis of soybean grain (% total fatty acids).

| Analyte | Literature Values[a] | Overall Treatment Effect $(Pr > F)$[b] | Control | Unsprayed (P-value,[c] Adj. P)[d] | Sprayed Glufosinate (P-value, Adj. P) | Sprayed 2,4-D (P-value, Adj. P) | Sprayed Both (P-value, Adj. P) |
|---|---|---|---|---|---|---|---|
| 8:0 Caprylic | 0.15 | NA | <LOQ | <LOQ | <LOQ | <LOQ | <LOQ |
| 10:0 Capric | NR | NA | <LOQ | <LOQ | <LOQ | <LOQ | <LOQ |
| 12:0 Lauric | 0.08-0.13 | NA | <LOQ | <LOQ | <LOQ | <LOQ | <LOQ |
| 14:0 Myristic | 0.07-0.24 | NA | <LOQ | <LOQ | <LOQ | <LOQ | <LOQ |
| 14:1 Myristoleic | 0.12-0.13 | NA | <LOQ | <LOQ | <LOQ | <LOQ | <LOQ |
| 15:0 Pentadecanoic | NR | NA | <LOQ | <LOQ | <LOQ | <LOQ | <LOQ |
| 15:1 Pentadecenoic | NR | NA | <LOQ | <LOQ | <LOQ | <LOQ | <LOQ |
| 16:0 Palmitic | 9.55-15.77 | 0.607 | 10.1 | 10.0 (0.625, 0.802) | 9.78 (0.148, 0.313) | 9.94 (0.455, 0.644) | 9.85 (0.249, 0.441) |
| 16:1 Palmitoleic | 0.09-0.19 | 0.029 | 0.097 | 0.085 (0.003, 0.028) | 0.088 (0.038, 0.124) | 0.087 (0.027, 0.105) | 0.089 (0.029, 0.109) |
| 17:0 Heptadecanoic | 0.09-0.15 | 0.640 | 0.111 | 0.114 (0.162, 0.336) | 0.113 (0.331, 0.539) | 0.114 (0.239, 0.432) | 0.113 (0.296, 0.493) |
| 17:1 Heptadecenoic | 0.07-0.09 | NA | <LOQ | <LOQ | <LOQ | <LOQ | <LOQ |
| 18:0 Stearic | 2.70-5.88 | 0.136 | 4.28 | 4.03 (0.048, 0.145) | 3.98 (0.018, 0.081) | 4.05 (0.060, 0.169) | 4.06 (0.073, 0.196) |
| 18:1 Oleic | 14.3-32.2 | 0.010 | 21.8 | 19.8 (0.004, 0.033) | 19.5 (0.001, 0.017) | 19.9 (0.006, 0.043) | 19.9 (0.006, 0.043) |
| 18:2 Linoleic | 42.3-58.8 | 0.145 | 50.3 | 52.5 (0.030, 0.109) | 51.9 (0 116, 0.268) | 52.6 (0.024, 0.095) | 52.0 (0.087, 0.222) |
| 18:3 γ-Linolenic | 3.00-12.52 | NA | <LOQ | <LOQ | <LOQ | <LOQ | <LOQ |
| 18:3 Linolenic | NR | 0.022 | 7.83 | 8.23 (0.003, 0.031) | 8.15 (0.016, 0.073) | 8.10 (0.034, 0.119) | 8.21 (0.004, 0.034) |
| 20:0 Arachidic | 0.16-0.48 | 0.023 | 0.307 | 0.284 (0.007, 0.045) | 0.282 (0.004, 0.033) | 0.285 (0.009, 0.052) | 0.287 (0.014, 0.067) |

TABLE 22-continued

Summary of the fatty acid analysis of soybean grain (% total fatty acids).

| Analyte | Literature Values[a] | Overall Treatment Effect (Pr > F)[b] | Control | Unsprayed (P-value,[c] Adj. P)[d] | Sprayed Glufosinate (P-value, Adj. P) | Sprayed 2,4-D (P-value, Adj. P) | Sprayed Both (P-value, Adj. P) |
|---|---|---|---|---|---|---|---|
| 20:1 Eicosenoic | 0.14-0.35 | 0.683 | 0.143 | 0.140 (0.582, 0.779) | 0.136 (0.201, 0.380) | 0.141 (0.794, 0.875) | 0.138 (0.327, 0.538) |
| 20:2 Eicosadienoic | 0.08-0.25 | NA | <LOQ | <LOQ | <LOQ | <LOQ | <LOQ |
| 20:3 Eicosatrienoic | NR | NA | <LOQ | <LOQ | <LOQ | <LOQ | <LOQ |
| 20:4 Arachidonic | NR | NA | <LOQ | <LOQ | <LOQ | <LOQ | <LOQ |
| 22:0 Behenic | 0.28-0.60 | 0.053 | 0.305 | 0.288 (0.023, 0.095) | 0.285 (0.008, 0.048) | 0.288 (0.020, 0.087) | 0.288 (0.020, 0.087) |

[a]Combined range.
[b]Overall treatment effect estimated using an F-test.
[c]Comparison of the transgenic treatments to the control using t-tests.
[d]P-values adjusted using a False Discovery Rate (FDR) procedure.
NA = statistical analysis was not performed since a majority of the data was <LOQ.
NR = not reported.
Bolded mean values are outside of the reported literature range.
Bolded P-values are significant (<0.05).

Example 8.2.5

Vitamins

An analysis of vitamins in soybean grain samples from the control, unsprayed soybean Event DAS-68416-4, soybean Event DAS-68416-4+glufosinate, soybean Event DAS-68416-4+2,4-D and soybean Event DAS-68416-4+ both herbicides was performed. A summary of the results across all locations is shown in Table 23.

No literature values were found for beta-tocopherol, delta-tocopherol, gamma-tocopherol, Vitamin A, Vitamin B5, Vitamin B6, Vitamin B12, Vitamin C, Vitamin D and niacin in soybean grain. Beta tocopherol, Vitamin A, Vitamin B12 and Vitamin D were all <LOQ. No differences were observed between the control, unsprayed AAD-12 and the treated AAD-12 for Vitamin B1, Vitamin B2, Vitamin B6, Vitamin C, Vitamin E or niacin. Of those vitamins with available literature ranges, all treatments fell within these ranges with the exception of vitamin B2 where values exceeded the range for all treatments including the near-isogenic control.

Delta-tocopherol levels were significantly different between the control and the soybean Event DAS-68416-4+ glufosinate and soybean Event DAS-68416-4+2,4-D entries based on unadjusted p-values. However this was not accompanied by a significant adjusted p-value or overall treatment effect. Gamma-tocopherol was significantly different between the control and the unsprayed and soybean Event DAS-68416-4+2,4-D entries based on unadjusted and adjusted p-values. However, gamma tocopherol was <11% higher for the soybean Event DAS-68416-4 treatments compared with the near-isogenic control.

Vitamin B5 levels were significantly different between the control and the soybean Event DAS-68416-4+glufosinate entry based on the adjusted p-value. However this was not accompanied by a significant overall treatment effect.

Folic acid was significantly different between the control and the unsprayed, soybean Event DAS-68416-4+2,4-D and soybean Event DAS-68416-4+both herbicides based on unadjusted p-values. Folic acid also had significant differences in the adjusted p-values for two of the soybean Event DAS-68416-4 entries compared with the control. However, folic acid levels were within the reported literature values for all treatments and the soybean Event DAS-68416-4 entries differed from the near-isogenic control by <9%, indicating equivalence to non-transgenic soybean.

Based on these compositional constituents, the grain from soybean Event DAS-68416-4 was substantially equivalent to that of non-transgenic soybean.

TABLE 23

Summary of vitamin analysis of soybean grain (mg/kg dry weight).

| Analyte | Literature Values[a] | Overall Treatment Effect (Pr > F)[b] | Control | Unsprayed (P-value,[c] Adj. P)[d] | Sprayed Glufosinate (P-value, Adj. P) | Sprayed 2,4-D (P-value, Adj. P) | Sprayed Both (P-value, Adj. P) |
|---|---|---|---|---|---|---|---|
| Beta Carotene (Vitamin A) | NR | NA | <LOQ | <LOQ | <LOQ | <LOQ | <LOQ |
| Vitamin B1 (Thiamin) | 1.01-2.54 | 0.560 | 2.10 | 2.14 (0.809, 0.886) | 1.94 (0 312, 0.517) | 1.97 (0 414, 0.615) | 2.14 (0.787, 0.873) |
| Vitamin B2 (Riboflavin) | 1.90-3.21 | 0.994 | 4.49 | 4.52 (0.933, 0.952) | 4.60 (0.677, 0.819) | 4.52 (0.922, 0.948) | 4.55 (0.817, 0.891) |
| Vitamin B3 (Niacin) | NR | 0.211 | 27.4 | 25.3 (0.060, 0.169) | 25.4 (0.076, 0.201) | 26.9 (0.698, 0.831) | 26.7 (0.513, 0.708) |
| Vitamin B5 (Panthotenic acid) | NR | 0.183 | 15.1 | 14.9 (0.601, 0.794) | 14.2 (0.041, 0.134) | 14.5 (0.170, 0.350) | 14.3 (0.065, 0.178) |
| Vitamin B6 (Pyridoxine) | NR | 0.788 | 5.50 | 5.51 (0.929, 0.951) | 5.40 (0.439, 0.634) | 5.40 (0.451, 0.642) | 5.39 (0.420, 0.620) |
| Vitamin B12 | NR | NA | <LOQ | <LOQ | <LOQ | <LOQ | <LOQ |

TABLE 23-continued

Summary of vitamin analysis of soybean grain (mg/kg dry weight).

| Analyte | Literature Values[a] | Overall Treatment Effect (Pr > F)[b] | Control | Unsprayed (P-value,[c] Adj. P)[d] | Sprayed Glufosinate (P-value, Adj. P) | Sprayed 2,4-D (P-value, Adj. P) | Sprayed Both (P-value, Adj. P) |
|---|---|---|---|---|---|---|---|
| Vitamin C | NR | 0.338 | 84.1 | 79.6 (0.126, 0.281) | 85.4 (0.639, 0.808) | 82.5 (0.580, 0.779) | 83.5 (0.838, 0.907) |
| Vitamin D | NR | NA | <LOQ | <LOQ | <LOQ | <LOQ | <LOQ |
| Vitamin E (alpha-Tocopherol) | 1.90-61.7 | 0.182 | 14.8 | 15.1 (0.762, 0.863) | 14.5 (0.611, 0.796) | 15.9) (0.137, 0.301) | 14.3) (0.439, 0.634) |
| Beta-Tocopherol | NR | NA | <LOQ | <LOQ | <LOQ | <LOQ | <LOQ |
| Delta-Tocopherol | NR | 0.095 | 92.6 | 95.1 (0.142, 0.305) | 96.5 (0.030, 0.109) | 97.1 (0.013, 0.067) | 94.5 (0.257, 0.446) |
| Gamma-Tocopherol | NR | 0.0004 | 153 | 164 (0.002, 0.021) | 158 (0.117, 0.268) | 169 (0.0005, 0.006) | 157 (0.174, 0.351) |
| Folic Acid | 2.39-4.71 | 0.006 | 3.70 | 3.49 (0.011, 0.060) | 3.56 (0.078, 0.203) | 3.38 (0.0004, 0.009) | 3.48 (0.008, 0.048) |

[a]Combined range.
[b]Overall treatment effect estimated using an F-test.
[c]Comparison of the transgenic treatments to the control using t-tests.
[d]P-values adjusted using a False Discovery Rate (FDR) procedure.
NR = not reported.
NA = statistical analysis was not performed since a majority of the data was <LOQ.
Bolded mean values are outside of the reported literature range.
Bolded P-values are significant (<0.05).

Example 8.2.5

Iso Flavones

The analysis of isoflavones in soybean grain samples from the control, unsprayed soybean Event DAS-68416-4, soybean Event DAS-68416-4+glufosinate, soybean Event DAS-68416-4+2,4-D and soybean Event DAS-68416-4+both herbicides was performed. A summary of the results across all locations is shown in Table 24.

The genistein and glycitein results were below the LOQ for the treated samples. Diadzin levels were significantly different between the control and the soybean Event DAS-68416-4+both herbicides entries based on unadjusted and adjusted p-values. However, the overall treatment effect was not significant. Although there are no reported literature values, the soybean Event DAS-68416-4+both herbicides treatment was <9% different from the near-isogenic control. Genistin levels were significantly different between the control and the soybean Event DAS-68416-4+both herbicides entries based on unadjusted and adjusted p-values. However, the overall treatment effect was not significant. Genistin values for all treatments were higher than the reported literature values, but the soybean Event DAS-68416-4 treatments were <9% different compared with the near-isogenic control. Glycitin values were significantly different between the control and the soybean Event DAS-68416-4+both herbicides based on unadjusted and adjusted p-values. While there were no reported literature values for glycitin, all soybean Event DAS-68416-4 entries were <13% different compared with the near-isogenic entry.

Based on these compositional constituents, the grain from soybean Event DAS-68416-4 soybean was substantially equivalent to that of non-transgenic soybean.

TABLE 24

Summary of isoflavone analysis of soybean grain (µg/g).

| Analyte | Literature Values[a] | Overall Treatment Effect (Pr > F)[b] | Control | Unsprayed (P-value,[c] Adj. P)[d] | Sprayed Glufosinate (P-value, Adj. P) | Sprayed 2,4-D (P-value, Adj. P) | Sprayed Both (P-value, Adj. P) |
|---|---|---|---|---|---|---|---|
| Daidzein | 60.0-2454 | NA | 19.2 | 31.2 | 14.8 | 13.0 | <LOQ |
| Daidzin | NR | 0.068 | 1085 | 1103 (0.584, 0.779) | 1112 (0.391, 0.589) | 1128 (0.187, 0.360) | 1179 (0.007, 0.045) |
| Genistein | 144-2837 | NA | 22.9 | <LOQ | <LOQ | <LOQ | <LOQ |
| Genistin | NR | 0.069 | 1282 | 1321 (0.292, 0.490) | 1327 (0.220, 0.408) | 1357 (0.052, 0.152) | 1389 (0.007, 0.044) |
| Glycitein | 15.3-1070 | NA | <LOQ | <LOQ | <LOQ | <LOQ | <LOQ |
| Glycitin | NR | 0.032 | 253 | 267 (0.142, 0.305) | 270 (0.076, 0.201) | 268 (0.121, 0.274) | 285 (0.002, 0.021) |

[a]Combined range.
[b]Overall treatment effect estimated using an F-test.
[c]Comparison of the transgenic treatments to the control using t-tests.
[d]P-values adjusted using a False Discovery Rate (FDR) procedure.
NA = statistical analysis was not performed since a majority of the data was <LOQ.
NR = not reported.
Bolded mean values are outside of the reported literature range.
Bolded P-values are significant (<0.05).

Example 8.2.5

Antinutrients

An analysis of anti-nutrients in soybean grain samples from the control, unsprayed soybean Event DAS-68416-4, soybean Event DAS-68416-4+glufosinate, soybean Event DAS-68416-4+2,4-D and soybean Event DAS-68416-4+ both herbicides was performed. A summary of the results across all locations is shown in Table 25.

No statistical differences were observed between the control and transgenic entries for lectin, phytic acid, or trypsin inhibitor. These three anti-nutrients were also all within the literature ranges, indicating equivalence to non-transgenic soybean.

Raffinose was significantly lower (<10%) for the soybean Event DAS-68416-4+glufosinate treatment compared with the control based on unadjusted p-values. Raffinose was not significantly different in the across-site analysis based on the adjusted p-value or the overall treatment effect. Raffinose levels were also within the reported literature values for all treatments, indicating equivalence to non-transgenic soybean.

Stachyose was significantly different between the control and the soybean Event DAS-68416-4+glufosinate entry based on the unadjusted p-value. Stachyose levels were not significant different in the across-site analysis based on the adjusted p-value or the overall treatment effect. Stachyose levels were also within the reported literature values for all treatments, indicating equivalence to non-transgenic soybean.

Anti-nutrient analysis for lectin, phytic acid, raffinose, stachyose and trypsin inhibitor were all within the reported literature values, and the two significant differences based on unadjusted p-values had lower levels of anti-nutrients for the soybean Event DAS-68416-4 treatments compared with the control.

Based on these compositional constituents, the grain from soybean Event DAS-68416-4 soybean was substantially equivalent to that of non-transgenic soybean.

Example 8.3

Summary of Grain and Forage Composition

The composition of soybean Event DAS-68416-4 was either statistically indistinguishable from the near-isogenic line, <13% different from the near-isogenic line, or within the literature range for non-transgenic soybean. Thus, soybean Event DAS-68416-4 was found to be substantially equivalent to non-transgenic soybean. Plots of the composition results do not indicate any biologically meaningful treatment-related compositional differences among unsprayed soybean Event DAS-68416-4, soybean Event DAS-68416-4+glufosinate, soybean Event DAS-68416-4+ 2,4-D and soybean Event DAS-68416-4+both soybean and the control soybean line. In conclusion, unsprayed soybean Event DAS-68416-4, soybean Event DAS-68416-4+glufosinate, soybean Event DAS-68416-4+2,4-D and soybean Event DAS-68416-4+both composition results confirm the equivalence of soybean Event DAS-68416-4 and conventional soybean.

Example 9

Pre-Plant Burndown Applications and Pre-Emergence Trials

This Example describes new methods of planting soybean crops and using herbicides, which are made possible by the subject invention.

Preplant burndown herbicide applications are intended to kill weeds that have emerged over winter or early spring prior to planting a given crop. Typically these applications are applied in no-till or reduced tillage management systems where physical removal of weeds is not completed prior to planting. A herbicide program, used in conjunction with no-till or reduced-till soybeans, therefore, must control a very wide spectrum of broadleaf and grass weeds present prior to the time of planting.

Glyphosate, gramoxone, and glufosinate are examples of non-selective, non-residual herbicides widely used for pre-plant burndown herbicide applications. Some weeds, however, are difficult to control with such herbicides due to one or more of the following factors: inherent insensitivity of the

TABLE 25

Summary of anti-nutrient analysis of soybean grain (% dry weight).

| Analyte | Literature Values[a] | Overall Treatment Effect (Pr > F)[b] | Control | Unsprayed (P-value,[c] Adj. P)[d] | Sprayed Glufosinate (P-value, Adj. P) | Sprayed 2,4-D (P-value, Adj. P) | Sprayed Both (P-value, Adj. P) |
|---|---|---|---|---|---|---|---|
| Lectin (H.U./mg) | 0.11-9.04 | 0.552 | 2.18 | 2.74 (0.333, 0.540) | 2.84 (0.254, 0.444) | 2.98 (0.176, 0.351) | 3.09 (0.124, 0.277) |
| Phytic Acid | 0.63-1.96 | 0.725 | 1.20 | 1.20 (0.949, 0.962) | 1.22 (0.673, 0.819) | 1.21 (0.896, 0.936) | 1.25 (0.253, 0.444) |
| Raffinose | 0.1-0.9 | 0.111 | 0.344 | 0.339 (0.753, 0.860) | 0.310 (0.033, 0.118) | 0.317 (0.082, 0.210) | 0.315 (0.062, 0.173) |
| Stachyose | 1.2-4.1 | 0.217 | 2.42 | 2.34 (0.378, 0.575) | 2.23 (0.027, 0.105) | 2.28 (0.105, 0.253) | 2.32 (0.231, 0.425) |
| Trypsin Inhibitor (TIU/mg) | 19.6-184 | 0.435 | 25.3 | 27.2 (0.204, 0.383) | 24.7 (0.657, 0.819) | 24.9 (0.748, 0.860) | 25.3 (0.973, 0.979) |

[a]Combined range.
[b]Overall treatment effect estimated using an F-test.
[c]Comparison of the transgenic treatments to the control using t-tests.
[d]P-values adjusted using a False Discovery Rate (FDR) procedure.
Bolded mean values are outside of the reported literature range.
Bolded P-values are significant (<0.05).

weed species or biotype to the herbicide, relatively large size of winter annual weeds, and cool weather conditions limiting herbicide uptake and activity. Several herbicide options are available to tank mix with these herbicides to increase spectrum and activity on weeds where the non-selective herbicides are inadequate. One example is the use of 2,4-D+glyphosate tank mix applications to assist in the control of *Conyza canadensis* (horseweed). Glyphosate can be used from 420 to 1680 g ae/ha, more typically 560 to 840 g ae/ha, for the preplant burndown control of most weeds present; however, 280-1120 g ae/ha of 2,4-D can be applied to aid in control of many broadleaf weed species (e.g., horseweed).

2,4-D is a preplant herbicide of choice because it is effective on a very wide range of broadleaf weeds (even at relatively low temperatures), and extremely inexpensive. However, if a crop planted after a burndown application is sensitive to 2,4-D (e.g., most dicot crops), 2,4-D residues in the soil (although short-lived) can injure the crop. For use with soybeans, many 2,4-D ester herbicide labels restrict the planting of new crops until at least 15 days after a burndown application of 1lb ai/acre. In the case of 2,4-D low volatile-ester formulations, rates of up to 0.5 lb ai/acre for burndown typically require planting 7 days after application, and rates of 1.0 lb ai/acre typically require planting 30 days after application. An additional concern in the case of 2,4-D amine products, which are water soluble, is that the herbicide may leach into the seed zone. Crops which contain an aad-12 gene, however, are tolerant to 2,4-D and are not negatively impacted by 2,4-D residues in the soil. Because of this tolerance, plants containing the aad-12 gene can be planted sooner after burndown without sustaining injury than plants which do not contain the aad-12 gene. Furthermore, the increased flexibility and reduced cost of 2,4-D herbicide with tankmix (or commercial premix) partners will improve weed control options and increase the robustness of burndown applications in important no-till and reduced tillage situations.

Preemergence applications of 2,4-D amine are applied at rates of 1120, 2240, 4480 g ae/ha at 7 days, 15 days or 30 days preplanting to soybean containing the aad-12 gene (Event DAS-68416-4) and control soybean. The preemergence applications are applied using art recognized procedures to field plots which are located at geographically distinct locales. Herbicide-treated plots are paired with untreated plots to provide accurate evaluation of emergence and early season growth. After planting and 2,4-D applications at 7, 15 or 30 days preplanting; injury of the soybean containing the aad-12 gene (Event DAS-68416-4) and control soybean is measured. Results of field testing indicate that soybean containing the aad-12 gene (Event DAS-68416-4) provides robust tolerance to preemergence treatments of 2,4-D herbicide at 7, 15, or 30 days preplanting.

These examples are a few of many options that are available. Those skilled in the art of weed control will note a variety of other applications including, but not limited to gramoxone+2,4-D or glufosinate+2,4-D by utilizing products described in federal herbicide labels (CPR, 2003) and uses described in Agriliance Crop Protection Guide (2003), as examples. Those skilled in the art will also recognize that the above example can be applied to any 2,4-D-sensitive (or other phenoxy auxin herbicide) crop that would be protected by the AAD-12 gene if stably transformed.

DAS-68416-4 soybeans are tolerant to the herbicide 2,4-D. This Example reports on the characterization of the herbicide tolerance of DAS-68416-4 soybean under field conditions. DAS-68416-4 soybeans were evaluated for tolerance to the herbicide 2,4-D in field trials conducted in the United States. For DAS-68416-4 soybeans, the proposed maximum application rates for will be 1120 g ae/ha for 2,4-D. Data discussed below indicates that DAS-68416-4 soybeans provide acceptable tolerance at rates of at least four times these proposed maximum use rates.

The efficacy of DAS-68416-4 soybean for the detoxification of 2,4-D and subsequent protection from injury caused by this compound was characterized in field studies. Trials were designed to evaluate the preemergence tolerance to 2,4-D. The preemergence trials were conducted as a randomized complete block design. Experimental units consisted of two-row plots for preemergence trials, approximately 3 m in length and all trials contained three replications. All herbicide applications were made with gas-pressurized small-plot spray equipment delivering approximately 140-190 l/ha of spray volume. The formulation of 2,4-D used was a 456 g ae/liter dimethylammonium salt. Visual injury ratings were taken approximately 7 days after crop emergence. Ratings were taken on a 0 to 100 scale which reflects a visual composite of all injury symptoms observed across all plants in a plot, with 0=no injury as compared to untreated plots and 100=death of all plants.

Preemergence trials consisted of 1120, 2240, and 4480 g ae/ha applied after planting but before crop emergence. Information regarding the preemergence trials is presented in Table 26.

TABLE 26

Site and treatment information for 2,4-D preemergence tolerance trials.

| DAS Trial No. | City | State | Soil Type | pH | % OM | Planting Date | App. Date | 1st Precip (d after app.) | Amt. (cm) |
|---|---|---|---|---|---|---|---|---|---|
| DCR0823 | Rosemount | MN | LOAM | 6.9 | 4.3 | May 20, 2008 | May 23, 2008 | 5.0 | 0.3 |
| DMS0828 | Fowler | IN | SANDY C.L. | 5.8 | 1.4 | May 29, 2008 | May 29, 2008 | 1.0 | 5.6 |
| JSR0803 | Greenville | MS | SILT LOAM | 7.8 | 2.0 | May 09, 2008 | May 09, 2008 | 1.0 | 0.6 |

In summary, field evaluations of 2,4-D tolerance were conducted. Studies examining the response of DAS-68416-4 soybeans and untransformed Maverick soybeans to applications of 2,4-D amine preemergence were conducted at locations in Mississippi, Indiana, and Minnesota. Averaged across the three locations, preemergence application of 2,4-D amine to DAS-68416-4 resulted in ≤2% injury regardless of application rate (Table 27). The same treatments caused 34 to 60% injury untransformed Maverick. Injury from preemergence applications of 2,4-D consisted of stand loss and reduction in growth.

TABLE 27

DAS-68416-4 Soybean Tolerance to Preemergence Applications of 2,4-D.

| Herbicide | Rate* | Application Stage[b] | Percent Plant Injury[c] | |
|---|---|---|---|---|
| | | | DAS-68416-4 | Maverick |
| 2,4-D amine | 1120 g ae/ha | preemergence | 2 ns | 34 b |
| 2,4-D amine | 2240 g ae/ha | preemergence | 2 ns | 58 a |
| 2,4-D amine | 4480 g ae/ha | preemergence | 0 ns | 63 a |

[a]ae/ha = acid equivalent/hectare
[b]Application stage in terms of soybean plant growth development.
[c]Means within each column followed by the same letter are not significantly different as determined by restricted maximum likelihood methods for mixed models and Tukey, or for unbalanced data, Tukey-Kramer HSD test (0.05). ns indicates no significant differences.

Example 10

Methods of Controlling Glyphosate-Resistant Weeds Using a Glyphosate Tolerance Gene+Soybean Event DAS-68416-4 in Combination Glyphosate is used extensively because it controls a very wide spectrum of broadleaf and grass weed species. However, repeated use of glyphosate in GTCs and in non-crop applications has, and will continue to, select for weed shifts to naturally more tolerant species or glyphosate-resistant biotypes. Tankmix herbicide partners used at efficacious rates that offer control of the same species but having different modes of action is prescribed by most herbicide resistance management strategies as a method to delay the appearance of resistant weeds. Stacking the 416 AAD-12 event with a glyphosate tolerance trait (and/or with other herbicide-tolerance traits) could provide a mechanism to allow for the control of glyphosate resistant dicot weed species in GTCs by enabling the use of glyphosate, phenoxy auxin(s) (e.g., 2,4-D)-and pyridyloxyacetates auxin herbicides (e.g., triclopyr)-selectively in the same crop. Applications of these herbicides could be simultaneously in a tank mixture comprising two or more herbicides of different modes of action; individual applications of single herbicide composition in sequential applications as pre-plant, preemergence, or postemergence and split timing of applications ranging from approximately 2 hours to approximately 3 months; or, alternatively, any combination of any number of herbicides representing each chemical class can be applied at any timing within about 7 months of planting the crop up to harvest of the crop (or the preharvest interval for the individual herbicide, whichever is shortest).

It is important to have flexibility in controlling a broad spectrum of grass and broadleaf weeds in terms of timing of application, rate of individual herbicides, and the ability to control difficult or resistant weeds. Glyphosate applications in a crop with a glyphosate resistance gene/AAD-12 416 Event stack could range from about 250-2500 g ae/ha; phenoxy auxin herbicide(s) (one or more) could be applied from about 25-4000 g ae/ha; and pyridyloxyacetates auxin herbicide(s) (one or more) could be applied from 25-2000 g ae/ha. The optimal combination(s) and timing of these application(s) will depend on the particular situation, species, and environment, and will be best determined by a person skilled in the art of weed control and having the benefit of the subject disclosure.

The vast majority of cotton, canola, corn, and soybean acres planted in North America contain a glyphosate tolerance (GT) trait, and adoption of GT corn is on the rise. Additional GT crops (e.g., wheat, rice, sugar beet, and turf) have been under development but have not been commercially released to date. Many other glyphosate resistant species are in experimental to development stage (e.g., alfalfa, sugar cane, sunflower, beets, peas, carrot, cucumber, lettuce, onion, strawberry, tomato, and tobacco; forestry species like poplar and sweetgum; and horticultural species like marigold, petunia, and begonias; isb.vt.edu/cfdocs/fieldtests1.cfm, 2005 on the World Wide Web). GTC's are valuable tools for the sheer breadth of weeds controlled and convenience and cost effectiveness provided by this system. However, glyphosate's utility as a now-standard base treatment is selecting for glyphosate resistant weeds. Furthermore, weeds that glyphosate is inherently less efficacious on are shifting to the predominant species in fields where glyphosate-only chemical programs are being practiced. By stacking AAD-12 Event 416 with a GT trait, either through conventional breeding or jointly as a novel transformation event, weed control efficacy, flexibility, and ability to manage weed shifts and herbicide resistance development could be improved. By transforming crops with AAD-12 Event 416, monocot crops will have a higher margin of phenoxy or pyridyloxy auxin safety, and phenoxy auxins can be selectively applied in dicot crops. Several scenarios for improved weed control options can be envisioned where AAD-12 Event 416 and a GT trait are stacked in any monocot or dicot crop species:

a) Glyphosate can be applied at a standard postemergent application rate (420 to 2160 g ae/ha, preferably 560 to 840 g ae/ha) for the control of most grass and broadleaf weed species. For the control of glyphosate resistant broadleaf weeds like *Conyza canadensis* or weeds inherently difficult to control with glyphosate (e.g., *Commelina* spp, *Ipomoea* spp, etc), 280-2240 g ae/ha (preferably 560-1120 g ae/ha) 2,4-D can be applied sequentially, tank mixed, or as a premix with glyphosate to provide effective control. For triclopyr, application rates would typically range from 70-1120 g ae/ha, more typically 140-420 g ae/ha. For fluroxypyr, application rates would typically range from 35-560 g ae/ha, more typically 70-280 ae/ha.

b) Currently, glyphosate rates applied in GTC's generally range from 560 to 2240 g ae/ha per application timing. Glyphosate is far more efficacious on grass species than broadleaf weed species. AAD-12 Event 416+GT stacked traits would allow grass-effective rates of glyphosate (105-840 g ae/ha, more preferably 210-420 g ae/ha). 2,4-D (at 280-2240 g ae/ha, more preferably 560-1120 g ae/ha) could then be applied sequentially, tank mixed, or as a premix with grass-effective rates of glyphosate to provide necessary broadleaf weed control. Triclopyr and fluroxypyr at rates mentioned above would be acceptable components in the treatment regimin. The low rate of glyphosate would also provide some benefit to the broadleaf weed control; however, primary control would be from the 2,4-D, triclopyr, or fluroxypyr.

One skilled in the art of weed control will recognize that use of one or more commercial aryloxy auxin herbicides alone or in combination (sequentially or independently) is enabled by AAD-12 Event 416 transformation into crops. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by AAD-12 Event 416, whether used alone, tank mixed, or sequentially, is considered within the scope of this invention.

REFERENCES

Severson, David W (Genomic Mapping Techniques, chapter 26$^{th}$, RFLP analysis of insect genomes)

Stam M., Mol. J. N. M. and Kooter J. M., (1997) The Silence of Genes in Transgenic Plants *Annals of Botany* 79: 3±12, 1997

Hood, E. E.; Helmer, G. L.; Fraley, R. T.; Chilton, M.-D. The Hypervirulence of *Agrobacterium tumefaciens* A281 Is Encoded in a Region of pTiBo542 Outside of T-DNA, *Journal of Bacteriology*, 1986 168(3):1291-1301.

Zeng, P.; Vadnais, D. A.; Zhang, Z.; Polacco, J. C. Refined glufosinate selection in *Agrobacterium*-mediated transformation of soybean [*Glycine max* (L.) Merrill], *Plant Cell Reports* 2004 22:478-482

The invention claimed is:

1. A transgenic soybean plant comprising a single copy of residues 2731 to 9121 of SEQ ID NO:1, inserted into the genome of said soybean plant between a host sequence of residues 1 to 2730 of SEQ ID NO:1 and a host sequence of residues 9122 to 10,212 of SEQ ID NO:1.

2. A soybean seed comprising a genome comprising AAD-12 event pDAB4468-0416 as present in representative seed deposited with American Type Culture Collection (ATCC) under Accession No. PTA-10442.

3. A soybean seed from the plant of claim 1, said seed comprising SEQ ID NO:1.

4. A soybean plant produced by growing the seed of claim 2, said plant comprising SEQ ID NO:1.

5. A progeny plant of the soybean plant of claim 4, said progeny plant comprising SEQ ID NO:1.

6. A herbicide-tolerant progeny plant of the soybean plant of claim 1, said progeny plant comprising SEQ ID NO:1.

7. A part of the plant of claim 4 wherein said part is selected from the group consisting of pollen, ovule, flowers, shoots, roots, and leaves, said part comprising SEQ ID NO:1.

8. An isolated polynucleotide molecule wherein said molecule comprises at least 15 nucleotides and hybridizes under stringent wash conditions with a nucleotide sequence selected from the group consisting of residues 2720 to 2740 of SEQ ID NO:1, residues 9112 to 9132 of SEQ ID NO:1, and complements thereof.

9. A method of breeding a soybean plant, said method comprising crossing the soybean plant of claim 1 with a second soybean plant to produce a third soybean plant comprising a genome, and assaying said third soybean plant for presence of SEQ ID NO:1 in said genome.

10. A method of introgressing a herbicide tolerance trait into a soybean plant, said method comprising crossing the soybean plant of claim 1 with a second soybean plant to produce a third soybean plant comprising a genome, and assaying said third soybean plant for presence of SEQ ID NO:1 in said genome.

11. A method of controlling weeds, said method comprising applying an aryloxy alkanoate herbicide to a field, said field comprising a plant of claim 1.

12. The method of claim 11, wherein said herbicide is selected from the group consisting of 2,4-D; 2,4-DB; MCPA; and MCPB.

13. The method of claim 11, wherein said method comprises applying a second herbicide to said field.

14. The method of claim 13, wherein said second herbicide is selected from the group consisting of glyphosate and dicamba.

15. A method of controlling weeds, said method comprising applying an aryloxy alkanoate herbicide to a field, and planting a seed of claim 3 in said field within 14 days of applying the herbicide.

16. A method of detecting a soybean event in a sample comprising soybean DNA wherein said method comprises contacting said sample with at least one polynucleotide that is diagnostic for the AAD-12 event as present in the seed of claim 2.

17. The method of claim 16 wherein said method comprises contacting said sample with
a. a first primer that binds to a flanking sequence selected from the group consisting of residues 1-2730 of SEQ ID NO:1, residues 9122-10,212 of SEQ ID NO:1, and complements thereof; and
b. a second primer that binds to an insert sequence comprising residues 2731-9121 of SEQ ID NO:1 or the complement thereof;
subjecting said sample to polymerase chain reaction; and assaying for an amplicon generated between said primers.

18. The method of claim 16 wherein said at least one polynucleotide comprises at least 30 nucleotides and hybridizes under stringent conditions with a sequence selected from the group consisting of residues 2720 to 2740 of SEQ ID NO:1, residues 9112 to 9132 of SEQ ID NO:1, and complements thereof; wherein said method further comprises subjecting said sample and said polynucleotide to stringent hybridization conditions; and assaying said sample for hybridization of said polynucleotide to said DNA.

19. The method of claim 11 wherein said method is used to treat or prevent herbicide-resistant weeds.

20. The method of claim 11 wherein said herbicide is applied prior to planting said plant.

21. A method of controlling glyphosate-resistant weeds in an area comprising at least one plant of claim 1, wherein said plant further comprises a glyphosate tolerance trait, and said method comprises applying an aryloxyalkanoate herbicide to at least a portion of said area.

22. The method of claim 21 wherein said herbicide is a phenoxy auxin.

23. The method of claim 21 wherein said herbicide is applied from a tank mix with glyphosate.

24. The method of claim 11 wherein at least one of said weeds is a glyphosate-resistant volunteer of a different species than said plant.

* * * * *